US006828423B1

(12) United States Patent
Chadwick et al.

(10) Patent No.: US 6,828,423 B1
(45) Date of Patent: Dec. 7, 2004

(54) METHODS AND COMPOSITIONS RELATING TO CD39-LIKE POLYPEPTIDES AND NUCLEIC ACIDS

(75) Inventors: Brian Paul Chadwick, Allston, MA (US); Anna-Maria Frischauf, London (GB)

(73) Assignee: Nuvelo, Inc., Sunnyvale, CA (US)

( * ) Notice: Subject to any disclaimer, the term of this patent is extended or adjusted under 35 U.S.C. 154(b) by 0 days.

(21) Appl. No.: 09/905,743

(22) Filed: Jul. 13, 2001

Related U.S. Application Data

(63) Continuation of application No. 09/240,639, filed on Jan. 29, 1999, now Pat. No. 6,350,447.

(51) Int. Cl.[7] .......................... C07K 16/40; C12N 1/00

(52) U.S. Cl. ............................ 530/387.1; 350/388.26; 350/389.1; 350/391.3; 350/350; 435/326; 435/810

(58) Field of Search ........................ 530/387.1, 388.26, 530/391.1, 391.3, 350; 435/326, 810

(56) References Cited

U.S. PATENT DOCUMENTS

| | | | |
|---|---|---|---|
| 4,235,871 A | | 11/1980 | Papahadjopoulos et al. |
| 4,501,728 A | | 2/1985 | Geho et al. |
| 4,683,195 A | | 7/1987 | Mullis et al. |
| 4,737,323 A | | 4/1988 | Martin et al. |
| 4,837,028 A | | 6/1989 | Allen |
| 4,946,778 A | | 8/1990 | Ladner et al. |
| 4,959,314 A | | 9/1990 | Mark et al. |
| 4,965,188 A | | 10/1990 | Mullis et al. |
| 5,202,231 A | | 4/1993 | Drmanac et al. |
| 5,525,464 A | | 6/1996 | Drmanac et al. |
| 5,858,682 A | * | 1/1999 | Gruenwald |

FOREIGN PATENT DOCUMENTS

| | | |
|---|---|---|
| CA | 2148851 | 10/1996 |
| WO | WO 90/03382 | 4/1990 |
| WO | WO 90/14148 | 11/1990 |
| WO | WO 91/09955 | 7/1991 |
| WO | WO 92/20808 | 11/1992 |
| WO | WO 94/12650 | 6/1994 |
| WO | WO 95/09248 | 4/1995 |
| WO | WO 96/30532 | 10/1996 |
| WO | WO 96/32471 | 10/1996 |
| WO | WO 00/04041 | 1/2000 |

OTHER PUBLICATIONS

Harlow et al (in Antibodies a Laboratory Manual, 1988, Cold Spring harbor laboratory publication, Cold Spring Harbor, NY, pp. 92–94, pp. 116–117, pp. 626–629.*

Campbell et al (in Monoclonal Antibody Technology, 1984, Elsevier Science Publisher, New York, NY, pp. 1–32.*

U.S. Appl. No. 09/122,449, Ford, filed Jul. 24, 1998.

U.S. Appl. No. 09/118,205, Ford, filed Jul. 16, 1998.

U.S. Appl. No. 09/240,639, Chadwick et al., filed Jan. 29, 1999.

Hicks–Berger, C.A. et al., "Expression and Characterization of Soluble and Membrane–bound Human Nucleoside Triphosphate Diphosphohydrolase 6 (CD39L2)," *J. Biol. Chem.*, 275(44):3401–34045 (2000).

Chadwick, B.P. et al., "Cloning and Mapping of a Human and Mouse Gene with Homology to Ecto–ATPase Genes," *Mammalian Genome*, 8:668–672(1997).

(List continued on next page.)

*Primary Examiner*—Christina Chan
*Assistant Examiner*—Phuong N. Hyunh
(74) *Attorney, Agent, or Firm*—Renee S. Polizotto

(57) ABSTRACT

The present invention provides polynucleotides and proteins encoded by such polynucleotides, along with therapeutic, diagnostic and research utilities for these polynucleotides and proteins. In particular, the polypeptides and polynucleotides of the invention comprise amino acid and nucleic acid sequences of novel CD39-like gene and gene products.

10 Claims, 46 Drawing Sheets

Figure 5A:
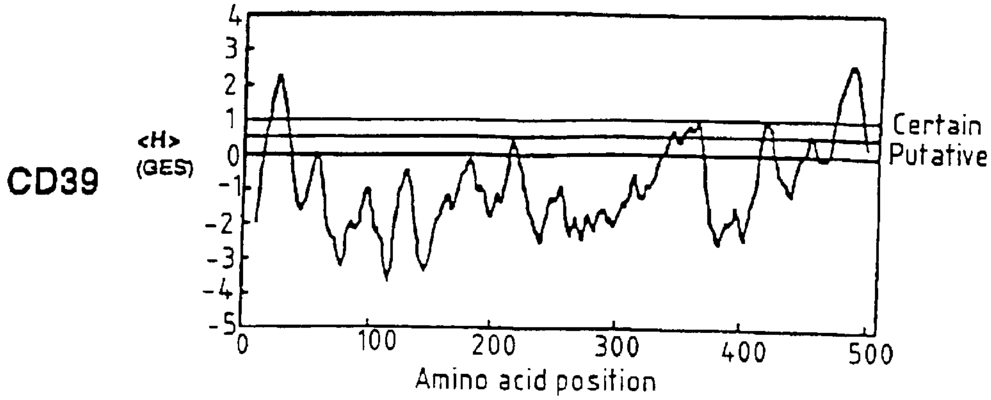
Figure 5B:
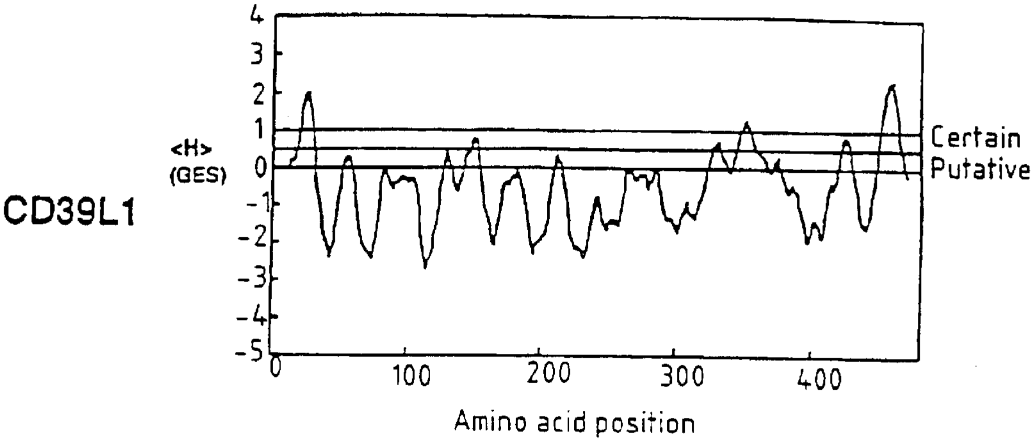

```
ACGTTGACAC AGGAATGAAG AGTGTATTGG CTGAATCTTC AAGCAGAGGC GATATTGACC 60

ATGTGCTTTT TAAATTGGCC TGCGTGACCC GCCCACTTGG TGTAAAAGAA GAACCGGCCA 120

AAGGGAGGGC CTGAAGGACC TCCACAGGAG TGTGAGCAGC ACTGCTTCAG CAACAAAGCC 180

TCAGGTCCAC ATCTTGGGAA GAAT ATG GCC ACT TCC TGG GGG GCT GTC TTC    231
                           Met Ala Thr Ser Trp Gly Ala Val Phe
                            1               5

ATG CTG ATC ATA GCC TGC GTT GGC AGC ACT GTC TTC TAC AGA GAA CAG   279
Met Leu Ile Ile Ala Cys Val Gly Ser Thr Val Phe Tyr Arg Glu Gln
 10                  15                  20                  25

CAG ACC TGG TTT GAA GGT GTC TTC TTG TCT TCC ATG TGC CCC ATT AAT   327
Gln Thr Trp Phe Glu Gly Val Phe Leu Ser Ser Met Cys Pro Ile Asn
                 30                  35                  40

GTC AGT GCC GGC ACC TTT TAT GGA ATT ATG TTT GAT GCG GGC AGC ACT   375
Val Ser Ala Gly Thr Phe Tyr Gly Ile Met Phe Asp Ala Gly Ser Thr
             45                  50                  55

GGA GCT CGG ATT CAT GTT TAC ACT TTT GTG CAG AAA ACA GCA GGA CAG   423
Gly Ala Arg Ile His Val Tyr Thr Phe Val Gln Lys Thr Ala Gly Gln
         60                  65                  70
```

OTHER PUBLICATIONS

Chadwick, B.P. et al. "cDNA Cloning and Chromosomal Mapping of a Mouse Gene with Homology to NTPases," *Mammalian Genome*, 9:162–164 (1998).
Chadwick B.P. et al., "The CD39–like Gene Family: Identification of Three New Human Members (CD36L2, CD39L3, and CD39L4), Their Murine Homologues, and a Member of the Gene Family from *Drosophila melanogaster,*" *Genomics*, 50:357–367(1998).
Smith, T.M.. et al., "Cloning, Sequencing, and Expression of a Human Brain Ecto–Apyrase Related to Both the Ecto–ATPases and CD39 Ecto–Apyrases," *Biochim. Biophys Acta*, 1386:65–78 (1998).
Adelman, J. P. et al., "In Vitro Deletional Mutagenesis for Bacterial Production of the 20,000–Dalton Form of Human Pituitary Growth Hormones," *DNA*, 2(3):183–193 (1983).
Mulero, J.J. et al., "CD39–L4 Is a Secreted Human Apyrase, Specific for Hydrolysis of Nucleoside Disphosphates," *J. Biol. Chem.*, 274(29): 20064–20067(1999).
Altschul, S.F. et al., "Basic Local Alignment Search Tool," *J. Mol. Biol.*, 215:403–410 (1990).
Altschul, S.F., "A Protein Alignment Scoring System Sensitive at All Evolutionary Distances," *J. Mol. Evol.*, 36:290–300 (1993).
Anderson, W.F., "Human Gene Therapy," *Nature* (*Supp.*), 392:25–30 (1998).
Asseline, U. et al., "Nucleic Acid–Binding Molecules with High Affinity and Base Sequence Specificity: Intercalating Agents Covalently Linked to Oligodeoxynucleotides," *Proc. Natl. Acad. Sci., USA*, 81: 3297–3301 (1984).
Bayer, E.A. et al., "The Avidin–Biotin Complex in Affinity Cytochemistry," *Meth. Enzym.*, 62:308–315 (1979).
Beal, P.A. et al., "Second Structural Motif for Recognition of DNA by Oligonucleotide–Directed Triple–Helix Formation," *Science*, 251:1360–1363 (1991).
Bonaldo, M. et al., "Normalization and Subtraction: Two Approaches to Facilitate Gene Discovery," *Genome Res.*, 6:791–806 (1986).
Boorstein et al., "Primer Extension Analysis of RNA," *Methods Enzymol.*, 180:347–369 (1989).
Breslauer, K.J. et al., "Predicting DNA Duplex Stability from the Base Sequence," *Proc. Natl. Acad. Sci. USA*, 83: 3746–3750 (1986).
Broude, N.E. et al., "Enhanced DNA Sequencing by Hybridization," *Proc. Natl. Acad. Sci., USA*, 91: 9072–3076 (1994).
Brumbaugh, J.A. et al, "Continuous, On–line DNA Sequencing Using Oligonucleotide Primers with Multiple Fluorophores," *Proc. Natl. Acad. Sci., USA*, 85:5610–5614 (1988).
Burnstock, G., "The Past, Present and Future of Purine Nucleotides as Signalling Molecules," *Neuropharmacology*, 36:1127–1139 (1997).
Cate, R.L. et al. "Genomic Southern Analysis with Alkaline–Phosphatase– Conjugated Oligonucleotide Probes and the Chemiluminescent AMPPD," *Genet. Anal. Tech. Appl.*, 8(3):102–106 (1991).
Cole, S.P.C. et al., "The EBV–Hybridoma Technique and It's Application to Human Lung Cancer," *Monoclonal Antibodies and Cancer Therapy*, Alan R. Liss, Inc., pp. 77–96 (1985).
Communi, D. et al., "Cloning, Functional Expression and Tissue Distribution of the Human $P2Y_6$ Receptor," *Biochem. Biophys. Res. Com.*, 222:.303–308 (1996).
Cooney, M. et al., "Site–Specific Oligonucleotide Binding Represses Transcription of the Human *c–myc* Gene in Vitro," *Science, 15241*:456–459 (1988).
Craig, M.E. et al., "Relaxation Kinetics of Dimer Formation by Self Comnplementary Oligonulceotides," *J. Mol. Biol.*, 62:383–401 (1971).
Dahlén et al., "Sensitive Detection of Genes by Sandwich Hybridization and Time–Resolved Fluorometry," *Mol. Cell. Probes* (*England*), 1:159–168 (1987).
Daly, J. et al., Direct Method for Determining Inorganic Phosphate in Serum with the "CentrifiChem", *Clin. Chem.*, 18:263–265 (1972).
Dolinnaya, N.G. et al., "Site–directed Modification of DNA Duplexes by Chemical Ligation," *Nucleic Acids Research*, (*England*), 16(9):3721–3738 (1988).
Dolinnaya, N.G. et al., "The use of BrCN for assembling modified DNA duplexes and DNA–RNA bybrids; comparison with water–soluble carbodiimide," *Nucleic Acids Res.* (*ENGLAND*), 19(11):3067–72 (1991).
Drmanac, R. et al., "A calculation of fragment lengths from human DNA with 78 restriction enzymes: an aid for cloning and mapping," *Nucleic Acids Research*, 14(11): 4691–4692 (1986).
Drmanac, R et al., Sequencing of Megabase Plus DNA by Hybridization: Theory of the Method, *Genomics*, 4:114–128 (1989).
Drmanac, R. et al., "Reliable Hybridization of Oligonucleotides as Short as Six Nucleotides," *DNA Cell Biol.*, 9:527–534 (1990).
Drmanac, R. et al., "An Algorithm for the DNA Sequence Generation from k–Tuple Word Contents of the Minimal Number of Random Fragments," *J. Biomol. Struct. Syn.*, 8(5):1085–1102 (1991).
Drmanac, R. et al., "Sequencing By Oligonucleotide Hybridization: A Promising Framework in Decoding of the Genome Program?" *Proceedings of the First International Conference Electrophoresis Supercomputing Human Genome*, Cantor et al., (Eds.), World Scientific Publishing Co., Singapore, pp. 47–59 (1991).
Drmanac, R. et al., "W (A or T) Sequences as Probes and Primers Suitable for Genomic Mapping and Fingerprinting," *Nucleic Acids Research*, 19(21):5839–5842 (1991).
Drmanac, R. et al., "DNA Sequence Determination by Hybridization: A Strategy for Efficient Large–Sacle Sequencing," *Science*, 260(5114):1649–1652 (1993).
Drmanac, S. et al., "Processing of cDNA and Genomic Kilobase–Size Clones for Massive Screening, Mapping and Sequencing by Hybridization," *Biotechniques*, 17:328–329, 332–336 (1994).
Dubyak, G. R. et al., "Signal Transuction via $P_2$–Purinergic Receptors for Extrecellular ATP and Other Nucleotides," *Am. J. Physiol. 34*:C577–C606 (1993).
Duncan, C.H. et al., "Affinity Chromatography of a Sequence–Specific DNA Binding Protein using Teflonlinked Oligonucleotides," *Anal. Biochem.*, 169:104–108 (1988).
Engval, E. et al., Enzyme–Linked Immunosorbent Assay, ELISA III. Quantitation of Specific Antibodies by Enzyme-Labeled Anti–Immunoglobulin in Antigen–Coated Tubes, *Immunol.*, 109:129–135 (1972).
Fischer Y. et al., "Purinergic Inhibition of Glucose Transport in Cardiomyocytes," *J. Biol. Chem.*, 274:755–761 (1999).
Friedmann, T., "Progress Toward Human Gene Therapy," *Science, 244*: 1275–1281 (1989).

Gayle III, R.B. et al., "Inhibition of Platelet Function by Recombinant Soluble Ecto–ADPase/CD39," *J. Clinical Investigation, 101(9)*:1851–1859 (1998).

Gluzman, Y., "SV40–Transformed Simian Cells Support the Replication of Early SV40 Mutants," *Cell*, 23:175–182 (1981).

Goding, J.W., "Conjugation of Antibodies with Fluorochromes: Modifications to the Standard Methods," *J. Immunol. Meth.*, 13: 215–226 (1976).

Gouttefangeas, C. et al., "The CD39 Molecule Defines Distinct Cytotoxic Subsets within Alloactivated Human CD8–Positive Cells," *Eur. J. Immunol., 22*:2681–2685 (1992).

Hillenkamp, F. et al., "Matrix Assisted UV–Laser Desorption/Ionization: A New Approach to Mass Spectrometry of Large Biomolecules," *in: Biologival Mass Spectrometry*, Burlingame et al., (eds.), Elsvier Science Pub., Amsterdam, p. 49–60 (1990).

Hoheisel et al., "Quantitative Measurements on the Duplex Stability of 2,6–Diaminopurine and 5–Chloro–Uracil Nucleotides using Enzymatically Synthesized Oligomers," *FEBS Lett*, 274:103–106 (1990).

Hurby et al., "Application of Synthetic Peptides: Antisense Peptides," *In Synthetic Peptides, A User's Guide*, W.H. Freeman, NY, pp. 289–307 (1992).

Huth–Fehre, T. et al., "Matrix Assisted Laser Desorption Mass Spectrometry of Oligodeoxythymidylic Acids," *Rapid Comm. Mass Spect., 6*:209–213 (1992).

Ikuta, S. et al., "Dissociation Kinetics of 19 Base Paired Oligonucleotide–DNA Duplexes Containing Different Single Mismatched Base Pairs," *Nucleic Acids Research*, 15:797–811 (1987).

Inouye, S. et al., "Microplate Hybridization of Amplified Viral DNA Segment," *J. Clin. Microbiol.*, 28:1469–1472 (1990).

Kaczmarek, E. et al., "Identification and Characterization of CD39/Vascular ATP Diphospohydrolase," *J. Biol. Chem.*, 271:33116–33122 (1996).

Kansas, G.S. et al., "Expression, Distribution, and Biochemistry of Human CD39 Role in Activation–Associated Homotypic Adhesion of Lymphocytes," *J. Immunol.*, 146:2235–2244 (1991).

Kasprzak, A. et al., "Location of a Contact Site between Actin and Myosin in the Three–Dimensional Structure of the Acto–S1 Complex," *Biochemistry*, 28:9230–9238 (1989).

Kirley, T.L., "Complementary DNA Cloning and Sequencing of the Chicken Muscle Ecto–ATPase," *J. Biol. Chem.*, 272:1076–1081 (1997).

Kohler, G. et al., "Continuous Cultures of Fused Cells Secreting Antibody of Predefined Specificity," *Nature*, 256:495–497 (1975).

Kozbor, D. et al., "The Production of Monoclonal Antibodies from Human Lymphocytes," *Immunology Today*, 4:72–79 (1983).

Lamture, J., "Direct Detection of Nucleic Acid Hybridization on the Surface of a Charge Coupled Device," *Nucleic Acids Research, 22*:2121–2125 (1994).

Landegren, U. et al., "A Ligase–Mediated Gene Detection Technique," *Science*, 241:1077–1080 (1988).

Lee, J.S. et al., "Complexes formed by (pyrimidine)$_n$ (purine)$_n$ DNAs on lowering the pH are three–stranded," *Nucl. Acids Res.,* 6:3073–3091 (1979).

Lehrach et al., "Hybridization Fingerprinting in Genome Mapping and Sequencing," in: *Genome Analysis Volume 1: Genetic and Physical Mapping*, Cold Spring Habor Laboratory Press, pp. 39–81 (1990).

Lutz, Y. et al., "The Distribution of Two hnRNP–Associated Proteins Defined by a Monoclonal Antibody Is Altered in Heat–Shocked HeLa Cells," *Exp. Cell Research.*, 175:109–124 (1988).

Makita, K. et al., "Placental ecto–ATP diphosphohydrolase: its structural feature distinct from CD39, localization and inhibition on shear–induced platelet aggregation," *International J. Hematology*, 68:297–310 (1998).

Maliszewski, C. R. et al., "The CD39 Lymphoid Cell Activation Antigen," *J. Immunology*, 153:3574–3583 (1994).

Marcus, A.J. et al., "The Endothelial Cell Ecto–ADPase Responsible for Inhibition of Platelet Function is CD39," *J. Clinical Investigation, 99*(6): 1351–1360 (1997).

Miller, A.D., "Human Gene Therapy Comes of Age," *Nature, 357*: 455–460 (1992).

Morrisey, D. et al., "Nucleic Acid Hybridization Assays Employing dA–Tailed Capture Probes. I. Single Capture Methods," *Mol. Cell. Probes*, 2:189–207 (1989).

Murakami, A. et al., "Fluorescent–Labeled Oligonucleotide Probes : Detection of Hybrid Formation in Solution by Fluorescence Polarization Spectroscopy," *Nucleic Acids Res.*, (*ENGLAND*), 19:4097–102 (1991).

Nagata, Y. et al., "Quantification of Picogram Levels of Specific DNA Immobilized in Microtiter Wells," *FEBS Lett* (*NETHERLANDS*), 183: 379–382 (1985).

Neumann, P.E. et al., "Mapping of Two Genes that Influence Susceptibility to Audiogenic Seizures in Crosses of C57BL/6J and DBA/2J Mice," *Behavior Genetics*, 20:307–323 (1990).

Nichols, R. et al. "A Universal Nucleoside for Use at Ambiguous Sites in DNA Primers," *Nature*, 369:492–493 (1994).

Nizetic, D. et al., "An Improved Bacterial Colony Lysis Procedure Enables Direct DNA Hybridisation Using Short (10, 11 bases) Oligonucleotides to Cosmids," *Nucleic Acids Research*, 19:182 (1991).

Okano, H. et al., "Myelin Basic Protein Gene and the Function of Antisense RNA in Its Repression in MyelinDeficient Mutant Mouse," *J. Neurochem.*, 56:560–567 (1991).

Ottman, R. et al., "Localization of a Gene for Partial Epilepsy to Chromosome 10q," *Nature Genet.*, 10:56–60 (1995).

Paterson, B.M. et al., "Structural Gene Identification and Mapping by DNA–mRNA Hybrid–Arrested Cell–Free Translation," *Proc. Natl. Acad. Sci., 74*:4370–4374 (1977).

Paunesku, T. et al., "Origin of Rat β–Globin Haplotypes Containing Three and Five Genes," *Mol. Biol. Evol.*, 7:407–422 (1990).

Pease, A.C. et al., "Light–generated Oligonucleotide Arrays for Rapid DNA Sequence Analysis," *Proc. Natl. Acad. Sci., USA*, 91:5022–5026 (1994).

Pevzner, P.A., "1–Tuple DNA Sequencing: Computer Analysis," *J. Biomol. Sruct. & Dyn., 7*(1):63–73 (1989).

Pontius, B.W. et al., "Rapid Renaturation of Complementary DNA Strands Mediated by Cationic Detergents: A Role for High–Probability Binding Domains in Enhancing the Kinetics of Molecular Assembly Processes,"*Proc. Natl. Acad. Sci., USA*, 88:8237–8241 (1991).

Pörshke, D. et al., "Co–operative Non–enzymic Base Recognition," *J. Mol. Biol.,* 62:361–381 (1971).
Rasmussen, S.R. et al., "Covalent Immobilization of DNA onto Polystyrene Microwells: The Molecules Are Only Bound at the 5' End," *Anal. Biochem.*, 198:138–142 (1991).
Rowe, M. et al., "Monoclonal Antibodies to Epstein–Barr Virus–Induced, Transformation–Associated Cell Surface Antigens: Binding Patterns and Effect Upon Virus–Specific T–Cell Cytotoxicity," *Int. J. Cancer*, 29:373–381 (1982).
Sambrook, J. et al., *In: Molecular Cloning A Laboratory Manual*, 2nd Ed., Cold Springs Harbor Press, pp. 9.14–9.28 (1989).
Schoenborn, M.A. et al., "Gene Structure and Chromosome Location of Mouse *Cd39* Coding for an Ecto–Apyrase," *Cytogenetics & Cell Genetics*, 81:287–289 (1998).
Schriefer, L.A. et al., "Low Pressure DNA Shearing: A Method for Random DNA Sequence Analysis," *Nucleic Acids Res.* (*ENGLAND*), 18 (24):7455–6 (1990).
Schubert, F. et al., "One–step Labelling of Oligonucleotides with Fluoresceine During Automated Synthesis," *Nucleic Acids Res.* (*ENGLAND*), 18:3427 (1990).
Schlman E. S. et al., "ATP Modulates Anti–IgE–Induced Release of Histamine from Human Lung Mast Cells," *Am. J. Respir. Cell Mol. Biol.*, 20:530–537 (1999).
Seyfried, T.N. et al., "Genetic Linkage Between the *AH* Locus and a Major Gene that Inhibits Susceptibility to Audiogenic Seizures in Mice," *Genetics*, 99:117–126 (1981).
Skobel, E. et al., "Relation Between Enzyme Release and Irreversible Cell Injury of the Heart under the Influence of Cytoskeleton Modulating Agents," *Biochim. Biophys. Acta*, 1362:128–134 (1997).
Smith, R.D. et al., "New Developments in Biochemical Mass Spectrometry: Electrospray Ionization," *Anal. Chem.,* 62:882–899 (1990).
Somers, G.R. et al., "Expression of the P2Y6 Purinergic Receptor in Human T Cells Infiltrating Inflammatory Bowel Disease," *Lab. Invest.,* 78:1375–1383 (1998).
Sternberger, L.A. et al., "The Unlabeled Antibody Enzyme Method of immunohistochemistry—Preparation and Properties of Soluble Antigen–Antibody Complex (Horseradish Peroxidase–Antihoreseradish Peroxidase) and Its Use in Identification of Spriochetes," *J. Histochem. Cytochem.,* 18: 315–333 (1970).
Stevanović, M. et al., Variant chromosomal arrangement of adult β–globin genes in rat *Gene*, 79:139–150 (1989).
Strezoska, Z. et al., "DNA Sequencing by Hybridization: 100 Bases Read by a Non–Gel–Based Method," *Proc. Natl. Acad. Sci., USA*, 88:10089–10093 (1991).
Van Ness, J. et al., "A Versatile Solid Support System for Oligodeoxynucleotide Probe–Based Hybridization Assays," *Nucleic Acids Res.*, (*ENGLAND*) 19:3345–3350 (1991).
Verma, I.M., "Gene Therapy—Treatment of Disease by Introducing Healthy Genes into the Body is Becoming Feasible. But the Therapy will not Reach its Full Potential until the Genes Can Be Coaxed to Work throughout Life," *Scientific American*, pp. 68–72, 81–84 (1990).
Vollrath, D. et al., "The Human Y Chromosome: A 43–Interval Map Based on Naturally Occuring Deletions," *Science, 258*:52–59 (1992).
Wallace, R.B. et al., "Hybridization of Synthetic Oligodeoxyribonucleotides to Φχ 174 DNA: The Effect of Single Base Pair Mismatch," *Nucleic Acids Research*, 6:3543–3557 (1979).
Walsh P.S. et al., "Preferential PCR Amplification of Alleles: Mechanisms and Solutions," *PCR Methods Appl*, 1:241–250 (1992).
Wang, T–F. et al., "CD39 Is an Ecto–($Ca^{2+}$, $Mg^{2+}$)–apyrase," *J. Biol. Chem., 271*(*17*):9898–9901 (1996).
Wang T–F. et al., "Characterization of Brain Ecto–Apyrase: Evidence for Only One Ecto–Apyrase (CD39) Gene," *Molecular Brain Research, 47*:295–302 (1997).
Wang, T–F. et al., "Widespread Expression of Ecto–Apyrase (CD39) in the Central Nervous System," *Brain Research, 790*:318–322 (1998).
Wang T–F et al., "The Transmembrane Domains of Ectoapyrase (CD39) Affect Its Enzymatic Activity and Quarternary Structure," *J. Biol. Chem.,* 273:24814–24821 (1998).
Wells, J.A. et al., "Cassette Mutagenesis: An Efficient Method for Generation of Multiple Mutations at Defined Sites," Gene, 34:315–323 (1985).
Wolter, A. et al., "Negative Ion FAB Mass Spectrometric Analysis of Non–Charged Key Intermediates in Oligonucleotide Synthesis: Rapid Identification of Partially Protected Dinucleoside Monophates," *Biomedical Environ. Mass Spec., 14*:111–116 (1987).
Xu, L. et al., "Ketone Electrophores and an Olefin–Release Group Electrophore–Labeled DNA Oligomer Detection via Electron Capture," *Chromatography*, 764:95–102 (1997).
Yamashita, M. et al., "Electrospray Ion Source. Another Variation on the Free–Jet Theme," *J. Phys. Chem., 88*:4451–4459 (1984).
Zoller, M.J. et al., Oligonucleotide–Directed Mutagenesis Using M13–Derived Vectors: An Efficient and General Procedure for the Production of Point Mutations in any Fragment of DNA, *Nucleic Acids Res.,* 10:6487–6500 (1982).
Fingl et al., "General Principles," In: *The Pharmacological Basis of Therapeutics*, Chapter 1, pp. 1–46 (1975).
Geiger et al., "Ligand specificity and ticlopidine effects distinguish three human platelet ADP receptors," *European Journal Pharmacology*, 351:235–246 (1998).
Hechler et al., "ATP Derivatives Are Antagonists of the P2Y1 Receptor: Similarities to the Platelet ADP Receptor," *American Pharmacology*, 53:727–733 (1998).
Ingall et al., "Antagonists of the Platelet $P_{2T}$ Receptor: A Novel Approach to Antithrombotic Therapy," *J. Med. Chem.,* 42:213–220 (1999).
Jantzen et al., "Evidence for Two Distinct G–proteincoupled ADP Receptors Mediating Platelet Activation," *Thromb. Haemost.,* 81:111–117 (1999).
Myers et al., "Automated Double–Label: In Situ Hybridization and Immunohistochemistry," *J. Surg. Path.,* 1:191–203 (1995).
Vigne et al., "Benzoyl ATP Is an Antagonist of Rat and Human P2Y1 Receptors and of Platelet Aggregation," *Biochem. Biophys. Res. Commun.,* 256:94–97 (1999).
Boukerche, H. et al., "Human melanoma cell lines differ in their capactiy to release ADP and aggregate platelets," *Br. J. Haematol.*, 87(4):763–72 (1994).
Dzhaudzhugazyan, K.N. et al., "Ecto–ATP diphosphohydrolase/CD39 is overexpressed in differentiated human melanomas," *FEBS Lett.,* 430(3):227–30 (1998).
Clifford, E.E. et al., "Stage–specific expression of P2Y receptors ecto–apyrase, and ecto–5'–nucteotidase in myeloid leukocytes," *Am. J. Physiol.*, 273(3 Pt. 1):C973–87 (1997).
Katzur, A.C., et al., Expression and responsiveness of P2Y2 receptors in human endometrial cancer cell lines, *J. Clin. Endocrinol. Metab.*, 84(11):4085–91 (1999).

Correale, P., et al., Extracellular adenosine 5' triphosphate involvement in the death of LAK–engaged human tumor cells via P2X–receptor activation, *Immunol. Lett.,* 55(2): 69–78 (1997).

Barnard. E.A., et al., "Nucleotide receptors in the nervous system. An abundant component using diverse transduction mechanisms," *Mol. Neurobiol.* 15(2):103–29 (1997).

Abbracchio, M.P. and Burnstock G., "Purinoreceptors: Are there families of P2X and P2Y Purinoreceptors?," *Pharmac. Ther.,* 64:445–75 (1994).

Illes, P. et al., "Electrophysiological effects of ATP on brain neurones," *J. Auton. Pharmacol.,* 16(6):407–11 (1996).

Bernard, E.A., et al., "The diverse series of recombinant P2Y purinoreceptors," *Ciba Found. Symp.,* 198: 166–88 (1996).

Williams, M. and Jarvis, M.F., "Purinergenic and pyrimidinergenic receptors as potential drug targets," *Biochem. Pharmacol.*, 59(10):1173–85 (2000).

King, B.F. et al., "Metabotropic receptors for ATP and UTP: exploring the correspondence between native and recombinant nucleotide receptors," *Trends Pharmacol. Sci.*, 19(12):506–14 (1998).

Nicholas, R.A., et al., "Pharmacological and second messenger signaling selectives of cloned P2Y receptors," *J. Auton. Pharmacol.*, 16(6):319–23 (1996).

Moore, D., et al. "Regional and cellular distribution of the P2Y(1) purinergenic receptor in the human brain: striking neuronal localisation," *J. Comp. Neurol.,* 421(3):374–84 (2000).

Sneddon. D., et al., "Modulation of purinergenic neurotransmission." *Prog. Brain. Res.*, 120:11–20 (1999).

Enjyoji, et al., "Targeted disruption of *cd39* (ATP diphosphohydrolase results in disordered homeostasis and thromboregulation," *Nature Medicine* 5(9): 1010–1017 (1999).

* cited by examiner

```
ACGTTGACAC AGGAATGAAG AGTGTATTGG CTGAATCTTC AAGCAGAGGC GATATTGACC 60

ATGTGCTTTT TAAATTGGCC TGCGTGACCC GCCCACTTGG TGTAAAAGAA GAACCGGCCA 120

AAGGGAGGGC CTGAAGGACC TCCACAGGAG TGTGAGCAGC ACTGCTTCAG CAACAAAGCC 180

TCAGGTCCAC ATCTTGGGAA GAAT ATG GCC ACT TCC TGG GGG GCT GTC TTC     231
                           Met Ala Thr Ser Trp Gly Ala Val Phe
                            1               5

ATG CTG ATC ATA GCC TGC GTT GGC AGC ACT GTC TTC TAC AGA GAA CAG    279
Met Leu Ile Ile Ala Cys Val Gly Ser Thr Val Phe Tyr Arg Glu Gln
 10                  15                  20                  25

CAG ACC TGG TTT GAA GGT GTC TTC TTG TCT TCC ATG TGC CCC ATT AAT    327
Gln Thr Trp Phe Glu Gly Val Phe Leu Ser Ser Met Cys Pro Ile Asn
                 30                  35                  40

GTC AGT GCC GGC ACC TTT TAT GGA ATT ATG TTT GAT GCG GGC AGC ACT    375
Val Ser Ala Gly Thr Phe Tyr Gly Ile Met Phe Asp Ala Gly Ser Thr
             45                  50                  55

GGA GCT CGG ATT CAT GTT TAC ACT TTT GTG CAG AAA ACA GCA GGA CAG    423
Gly Ala Arg Ile His Val Tyr Thr Phe Val Gln Lys Thr Ala Gly Gln
        60                  65                  70
```

FIG. 1A

```
ctc ccc ttt ctg gaa ggt gaa att ttt gat tct gtg aag ccg gga ctt    471
Leu Pro Phe Leu Glu Gly Glu Ile Phe Asp Ser Val Lys Pro Gly Leu
     75                  80                  85

TCT GCT TTT GTG GAT CAG CCC AAA CAG GGT GCT GAG ACT GTC CAG GAG    519
Ser Ala Phe Val Asp Gln Pro Lys Gln Gly Ala Glu Thr Val Gln Glu
 90                  95                 100                 105

CTC TTG GAG GTG GCC AAA GAC TCG ATC CCC AGA AGC CAC TGG GAA AGG    567
Leu Leu Glu Val Ala Lys Asp Ser Ile Pro Arg Ser His Trp Glu Arg
                110                 115                 120

ACC CCG GTG GTT CTG AAA GCA ACG GCC GGA CTC CGT TTG CTG CCT GAG    615
Thr Pro Val Val Leu Lys Ala Thr Ala Gly Leu Arg Leu Leu Pro Glu
            125                 130                 135

CAG AAA GCC CAG GCT CTG CTC TTG GAG GTA GAG GAG ATC TTC AAG AAT    663
Gln Lys Ala Gln Ala Leu Leu Leu Glu Val Glu Glu Ile Phe Lys Asn
        140                 145                 150

TCA CCT TTC CTG GTC CCA GAT GGC AGC GTT AGC ATC ATG GAT GGG TCC    711
Ser Pro Phe Leu Val Pro Asp Gly Ser Val Ser Ile Met Asp Gly Ser
    155                 160                 165
```

FIG. 1B

```
TAT GAA GGC ATA CTA GCC TGG GTT ACC GTG AAC TTT CTA ACA GGT CAG    759
Tyr Glu Gly Ile Leu Ala Trp Val Thr Val Asn Phe Leu Thr Gly Gln
170                 175                 180                 185

CTG CAT GGT CGT GGC CAG GAG ACT GTG GGG ACC CTT GAC CTG GGG GGT    807
Leu His Gly Arg Gly Gln Glu Thr Val Gly Thr Leu Asp Leu Gly Gly
                190                 195                 200

GCC TCC ACC CAA ATC ACG TTT CTA CCC CAG TTT GAG AAA ACC CTG GAA    855
Ala Ser Thr Gln Ile Thr Phe Leu Pro Gln Phe Glu Lys Thr Leu Glu
            205                 210                 215

CAA ACA CCT AGG GGC TAC CTC ACT TCC TTT GAG ATG TTT AAC AGC ACT    903
Gln Thr Pro Arg Gly Tyr Leu Thr Ser Phe Glu Met Phe Asn Ser Thr
        220                 225                 230

TTT AAG CTC TAT ACA CAT AGT TAC TTG GGA TTT GGA CTG AAA GCT GCA    951
Phe Lys Leu Tyr Thr His Ser Tyr Leu Gly Phe Gly Leu Lys Ala Ala
    235                 240                 245

AGA CTG GCA ACT CTG GGA GCC CTG GAA GCA AAA GGG ACT GAT GGA CAT    999
Arg Leu Ala Thr Leu Gly Ala Leu Glu Ala Lys Gly Thr Asp Gly His
250                 255                 260                 265
```

FIG. 1C

```
ACG TTT CGA AGT GCC TGT TTA CCA AGA TGG TTG GAA GCA GAG TGG ATC    1047
Thr Phe Arg Ser Ala Cys Leu Pro Arg Trp Leu Glu Ala Glu Trp Ile
                270                 275                 280

TTT GGG GGT GTG AAA TAC CAG TAT GGT GGT AAC CAA GAA GGG GAG ATG    1095
Phe Gly Gly Val Lys Tyr Gln Tyr Gly Gly Asn Gln Glu Gly Glu Met
            285                 290                 295

GGC TTT GAA CCC TGC TAT GCG GAA GTG CTG AGG GTA GTA CAG GGG AAA    1143
Gly Phe Glu Pro Cys Tyr Ala Glu Val Leu Arg Val Val Gln Gly Lys
        300                 305                 310

CTT CAC CAG CCA GAA GAA GTC CGA GGA AGC GCC TTC TAC GCT TTC TCT    1191
Leu His Gln Pro Glu Glu Val Arg Gly Ser Ala Phe Tyr Ala Phe Ser
    315                 320                 325

TAC TAC TAC GAT CGA GCC GCT GAC ACA CAC TTG ATC GAT TAT GAA AAG    1239
Tyr Tyr Tyr Asp Arg Ala Ala Asp Thr His Leu Ile Asp Tyr Glu Lys
330                 335                 340                 345

GGC GGG GTT TTA AAA GTT GAA GAT TTT GAA AGA AAA GCC AGA GAA GTG    1287
Gly Gly Val Leu Lys Val Glu Asp Phe Glu Arg Lys Ala Arg Glu Val
                350                 355                 360
```

FIG. 1D

```
TGT GAC AAC TTG GGG AGC TTC TCC TCG GGC AGT CCT TTC CTC TGC ATG   1335
Cys Asp Asn Leu Gly Ser Phe Ser Ser Gly Ser Pro Phe Leu Cys Met
            365                 370                 375

GAC CTC ACT TAC ATC ACA GCC CTG TTG AAA GAT GGT TTG GGC TTT GCC   1383
Asp Leu Thr Tyr Ile Thr Ala Leu Leu Lys Asp Gly Leu Gly Phe Ala
        380                 385                 390

GAA CGG CAC CCT CTT ACA GCT CAC AAA GAA AGT GAA CAA CAT AGA GAC   1431
Glu Arg His Pro Leu Thr Ala His Lys Glu Ser Glu Gln His Arg Asp
    395                 400                 405

TGG TTG GGC CTT GGG GGC CAC CTT TCA CCT GCT CCA GTC TCT GGG CAT   1479
Trp Leu Gly Leu Gly Gly His Leu Ser Pro Ala Pro Val Ser Gly His
410                 415                 420                 425

CAC CAG CTG AGG CCA AGC TCC ACC TCT GAA GCC TGC ATT TCT GAA CCA   1527
His Gln Leu Arg Pro Ser Ser Thr Ser Glu Ala Cys Ile Ser Glu Pro
                430                 435                 440

GTT TTC TCA CAG GAA GGC GTG GAC TCA GAG ACA TTT TCT GAC CTC TCT   1575
Val Phe Ser Gln Glu Gly Val Asp Ser Glu Thr Phe Ser Asp Leu Ser
            445                 450                 455
```

FIG. 1E

```
GGA AAA GCC TGG CCC GAA ACC CGT TAACTGGTTT TATAAGGAGG GAGGGGTTTT  1629
Gly Lys Ala Trp Pro Glu Thr Arg
        460                 465

TAGATGAGTC TTGCTCTTGA GCCTAGTGAT TTGGGCTTCA ATGATTTGCA CATCTAATGT 1689

GAATAGCTCC TAACCACTTG GTGGGTGCAT GGCTGGCACC AGACTGTAAA TCTTTTGGGA 1749

TTCTTTGTAC AGAGTCCTGC AAAGGAAAAA AGAGAAAAGG TTTGGAACTC CATGCTAGAT 1809

TGCGAGTTCA GAGACAGGTC CCTGGGGACC AAAGAACAAT CTCGTTTCAA CCCTTGGATG 1869

CCTCATTGCT TTGAATGGAT TCATTTTTGC TTATAAGCTG ATTTACTGAA ATCCCATAAC 1929

CCATCAATGC TGTTAATTTT TTTCTTCCTA CCCTTATTAC ATTCCCTACC CTAAAAGCCT 1989

GGGGGAAATA CCTGGTTTTG CTTCCCATCT ATAATTGAGA AAGAGGGGGG AAAAGATACT 2049

GTATTAGAAT TTGTGTGATC CTGTGGCACA ATAGATCAAC CAACCCATTT AAAGCTTAAA 2109

AAAAAAAAAA                                                        2119
```

FIG. 1F

```
peaNTPase    1   ----MELLIKLITFLLFSMPAITSSQYLGNNLLTSRKIFLKQEEISSYAVVFDAGSTGSR
potapyrase   1   MLNQNSHFIFIILAIFLVLPLSLLSKNVNAQIPLRRHLLSHESE--HYAVIFDAGSTGSR
mNTPase      1   MATSWGAVFMLIIACVGSTVFYREQQTWFEGVFLSSMCPINVSAGTFYGIMFDAGSTGTR
yGDPase      1   KTPEDISILPVNDEPGYLQDSKTEQNYPELADAVKSQTSQTCSEEHKYVIMIDAGSTGSR

peaNTPase    57  IHVYHFNQNLDLLHIGKGVEYYNKITPGLSSYANNPEQAAKSLIPLLEQAEDVVPDDLQP
potapyrase   59  VHVFRFDEKLGLLPIGNNIEYFMATEPGLSSYAEDPKAAANSLEPLLDGAEGVVPQELQS
mNTPase      61  IHVYTFVQKTAGQLPFLEGEIFDSVKPGLSAFVDQPKQGAETVQELLEVAKDSIPRSHWE
yGDPase      61  VHIYKFDVCTS--PPTLLDEKFDMLEPGLSSFDTDSVGAANSLDPLLKVAMNYVPIKARS

peaNTPase    117 KTPVRLGATAGLRLLNGDASEKILQSVRDMLSNRSTF-NVQPDAVSIIDGTQEGSYLWVT
potapyrase   119 ETPLELGATAGLRMLKGDAAEKILQAVRNLVKNQSTF-HSKDQWVTILDGTQEGSYMWAA
mNTPase      121 RTPVVLKATAGLRLLPEQKAQALLLEVEEIFKN-SPF-LVPDGSVSIMDGSYEGILAWVT
yGDPase      119 CTPVAVKATAGLRLLGDAKSSKILSAVRDHLEKDYPFPVVEGDGVSIMGGDEEGVFAWIT
```

FIG. 2A

```
peaNTPase  176 VNYALGNLGKKYTK--TVGVIDLGGGSVQMAYAVSKKTAKNAPKVADGDDPYIKKVVLKG
potapyrase 178 INYLLGNLGKDYKS--TTATIDLGGGSVQMAYAISNEQFAKAPQNEDG-EPYVQQKHLMS
mNTPase    179 VNFLTGQLHGRGQE--TVGTLDLGGASTQITFLPQFEK-----TLEQTPRGYLTSFEMFN
yGDPase    179 TNYLLGNIGANGPKLPTAAVFDLGGGSTQIVFEP---TFPINEKMVDGEHKF--DLKFGD

peaNTPase  234 IPYDLYVHSYLHFGREASRAEILKL------------------TPRSPNPCLLAGFNGIY
potapyrase 235 KDYNLYVHSYLNYGQLAGRAEIFKA------------------SRNESNPCALEGCDGYY
mNTPase    232 STFKLYTHSYLGFGLKAARLATLGA------------------LEAKGT----DGHTFRS
yGDPase    234 ENYTLYQFSHLGYGLKEGRNKVNSVLVENALKDGKILKGDNTKTHQLSSPCLPPKVNATN

peaNTPase  276 TYSGEEFKATAYTSGA-----NFNKCKNTIRKALKLNYPCPYQNCTFGGIWNGGGGN---
potapyrase 277 SYGGVDYKVKAPKKGS-----SWKRCRRLTRHALKINAKCNIEECTFNGVWNGGGGD---
mNTPase    270 ACLPRWLEAEWIFGGV-----KYQYGGNQEGEMGFEPCYAEVLRVVQGKLHQPEEVR---
yGDPase    294 EKVTLESKETYTIDFIGPDEPSGAQCRFLTDEILNKDAQCQSPPCSFNGVHQPSLVRTFK
```

FIG. 2B

```
peaNTPase   328  G Q K N L F A S S S F F Y L P E D T G M V D A S T P N F I L R P V D I E T K A K E A C A L N F E D A K S T Y P F L D K K
potapyrase  329  G Q K N I H A S S F F Y D I G A Q V G I V D T K F P S A L A K P I Q Y L N A A K V A C Q T N V A D I K S I F P K T Q D R
mNTPase     322  G S A - F Y A F S Y Y Y D R A A D T H L I D Y E - K G G V L K V E D F E R K A R E V C D - N L G S F S S G S P - - - - -
yGDPase     354  E S N D I Y I F S Y F Y D R T R P L G M P L S F T L N E L N D L A R I V C K G E E T W N S V F S G I A G S - - - L D E L

peaNTPase   388  N V A S Y V C M D L I Y Q Y V L L V D G F G L D P L Q K I T S G K E I E Y Q D A I V E A A W P L G N A V E A I S A L P K
potapyrase  389  N I - P Y L C M D L I Y E Y T L L V D G F G L N P H K E I T V I H D V Q Y K N Y L V G A A W P L G C A I D L V S S T T N
mNTPase     374  - - - - F L C M D L T Y I T A L L K D G L G F A E R H P L T A H K E S E Q H R D W L G L G G H L S P A P V S G H H Q L R
yGDPase     411  E S D S H F C L D L S F Q V S L L H T G Y D I P L Q R E L R T G K K I A N K E - - - - I G W C L G A S L P L L K A D N W

peaNTPase   448  F E R L M Y F V
potapyrase  448  K I R V A S S *
mNTPase     430  P S S T S E A C I S E P V F S Q E G V D S E T F S D L S G K A W P E T R *
yGDPase     467  K C K I Q S A
```

FIG. 2C

| | | ACR I | | | |
|---|---|---|---|---|---|
| CD39 | 1 | VKYGIVL**DAGSSHTS**LYIYKW | -------- | PAEKENDTGV | ---------VHQVEECRVK-GPGIS |
| ratCD39 | 1 | VKYGIVL**DAGSSHTN**LYIYKW | -------- | PAEKENDTGV | ---------VQLLEECQVK-GPGIS |
| CD39L1 | 1 | LKYGIVL**DAGSSHTS**MFIYKW | -------- | PADKENDTGI | ---------VGQHSSCDVP-GGGIS |
| chlATPase | 1 | FKYGIVL**DAGSSHTA**VFIYKW | -------- | PADKENDTGV | ---------VSEHSMCDVE-GPGIS |
| peaNTPase | 1 | SSYAVVF**DAGSTGS**RIHVYHF | -------- | NQ-NLDLLHIGKGVEYYN | ----KITPGLS |
| potRROP1 | 1 | EHYAVIF**DAGSTGS**RVHVFRF | -------- | DE-KLGLLPIGNNIEYFM | ----ATEPGLS |
| yGDA1 | 1 | HKYVIMI**DAGSTGS**RVHIYKF | -------- | DVCTSP--PTLLD-EKFD | ----MLEPGLS |
| mNTPase | 1 | TFYGIMF**DAGSTGT**RIHVYTF | -------- | VQKTAGQLPPLEG-EIFD | ----SVKPGLS |
| hCD39L2 | 1 | | -------- | | ----FK-------ALKPGLS |
| celegans | 1 | IKYGVIC**DAGSGT**RLFVYTLKPLSGGL | --TNIDT----L | ----IHESEPVVKKVTPGLS |
| y71KD | 1 | DRFGIVI**DAGSSGS**RIHVFKWQDTESLLHATNQDSQSILQSVPHIHQEKDWTFKLNPGLS |

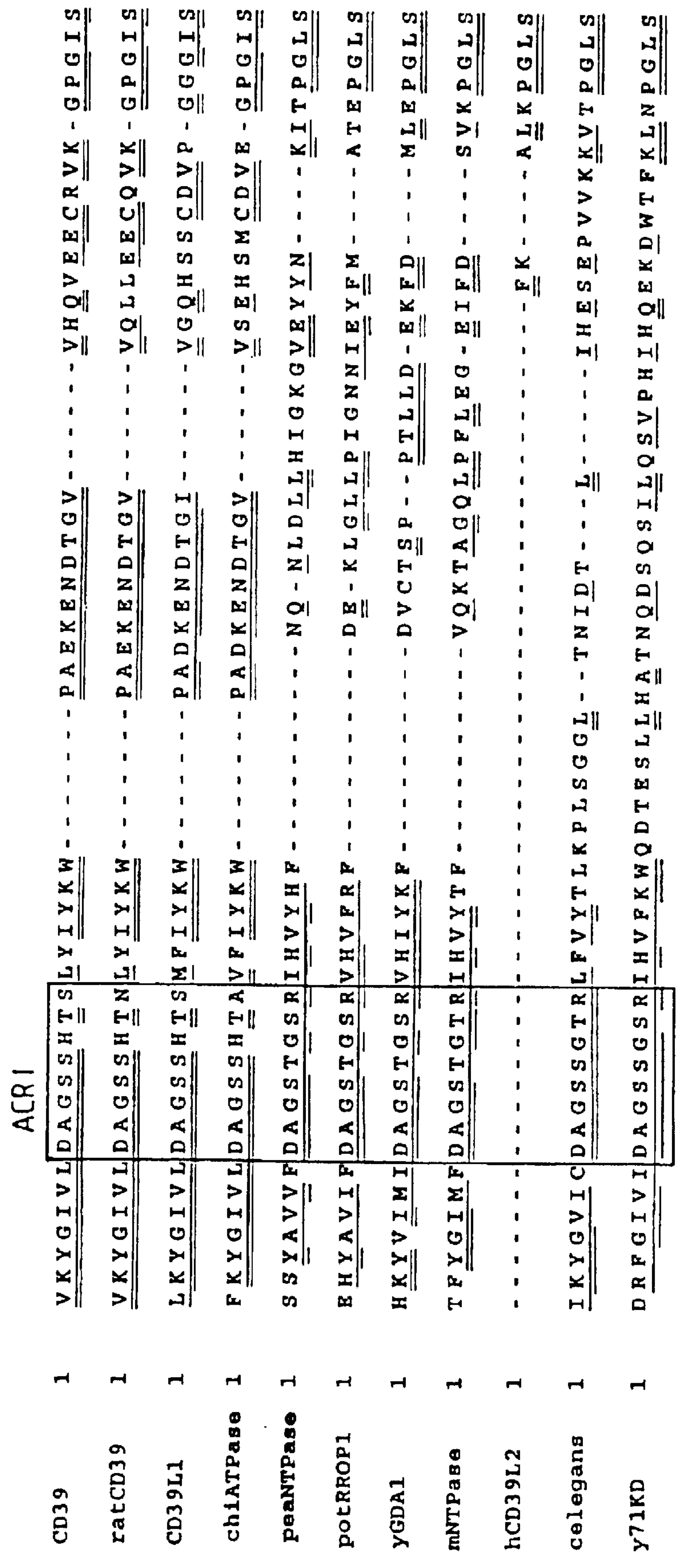

FIG. 3A

ACR II

```
CD39       47  KF-VQKVNEIGI-YLTDCMERAREVIPR---S-QHQETPVYLGATAGMRLLRMESEELAD
ratCD39    47  KY-AQKTDEIAA-YLAECMKMSTERIPA---SKQHQ-TPVYLGATAGMRLLRMESKQSAD
CD39L1     47  SY-ADNPSGASQ-SLVGCLEQALQDVPK---ER-HAGTPLYLGATAGMRLLNLTNPEAST
chiATPase  47  SY-SSKPPAAGK-SLEHCLSQAMRDVPK---EK-HADTPLYLGATAGMRLLTIADPPSQT
peaNTPase  46  SY-ANNPEQAAKS-LIPLLEQAEDVVP----DDLQPKTPVRLGATAGLRLLN--GDA-SE
potRROP1   46  SY-AEDPKAAANS-LEPLLDGAEGVVP----QELQSETPLELGATAGLRMLK--GDA-AE
yGDA1      44  SPDTDSV-GAANS-LDPLLKVAMNYVPI----KARSCTPVAVKATAGLRLL---GDAKSS
mNTPase    46  AF-VDQPKQGAET-VQELLEVAKDSIPRSHWE--R--TPVVLKATAGLRLL---PEQKAQ
hCD39L2    10  AY-ADDVEKSAQG-IRELLDVAKQDIP---FDSGRP-TPLVLKATAGLRLL---PGEKAQ
celegans   51  SFG-DKPEQVVE-YLTPLLRFAEEHIPYEQLGE----TDLLIFATAGMRLL---PEAQKD
y71KD      61  SFE-KKPQDAYKSHIKPLLDFAKNIIPESHWSS----CPVFIQATAGMRLL---PQDIQS
```

FIG. 3B

|            |     |                           |                        | ACR III               |                          |
|------------|-----|---------------------------|------------------------|-----------------------|--------------------------|
| CD39       | 101 | RVLDVVERSLSN-YPF--------  | DFQGARIIT              | GQEEGAYGWITIN         | YLLGKFSQKTRWFSIVP        |
| ratCD39    | 101 | EVLAAVSRSLKS-YPF--------  | DFQGAKIIT              | GQEEGAYGWITIN         | YLLGRFTQEQSWLNFIS        |
| CD39L1     | 101 | SVLMAVTHTLTQ-YPF--------  | DFRGARILS              | GQEEGVFGWVTA          | NYLLENFI-KYGWVG--R       |
| chiATPase  | 101 | -CLSAVMATLKS-YPF--------  | DFGGAKILS              | GEEEGVFGWITA          | NYLLENFI-KRGWLG--E       |
| peaNTPase  | 97  | KILQSVRDMLSNRSTFN-VQPD-A- | VSIIDGT                | QEGSYLWVTVN           | YALGN--------L---G       |
| potRROP1   | 97  | KILQAVRNLVKNQSTFH--SKD-   | QWTILDGT               | QEGSYMAAIN            | YLLGN--------L---G       |
| yGDA1      | 95  | KILSAVRDHLEKDYPFPVVEGD-G- | VSIMGGD                | EEGVFAWITT            | NYLLGN--------IGANG      |
| mNTPase    | 97  | ALLEVEEIF-KNSPF-LV-PD-    | GSVSIMDGS              | YEGILAWVTVN           | FLTGQ--------LHGRG       |
| hCD39L2    | 97  | KLLQKVKEYL-KHSPF-LV-GD-   | DCVSIMNGT              | DEGVSAWXTIN           | FLTGS--------LKTPG       |
| celegans   | 61  | AIIKNLQNGLKSVTALRVSD---   | SNIRIIDGA              | WEGIYSWIAVN           | YILGR--------F-D--       |
| y71KD      | 102 | SILDGLCQGLKHPAEFLVEDCS-   | AQIQVIDGR              | TEGLYGWLGLN           | YLYGH--------FNDYN       |

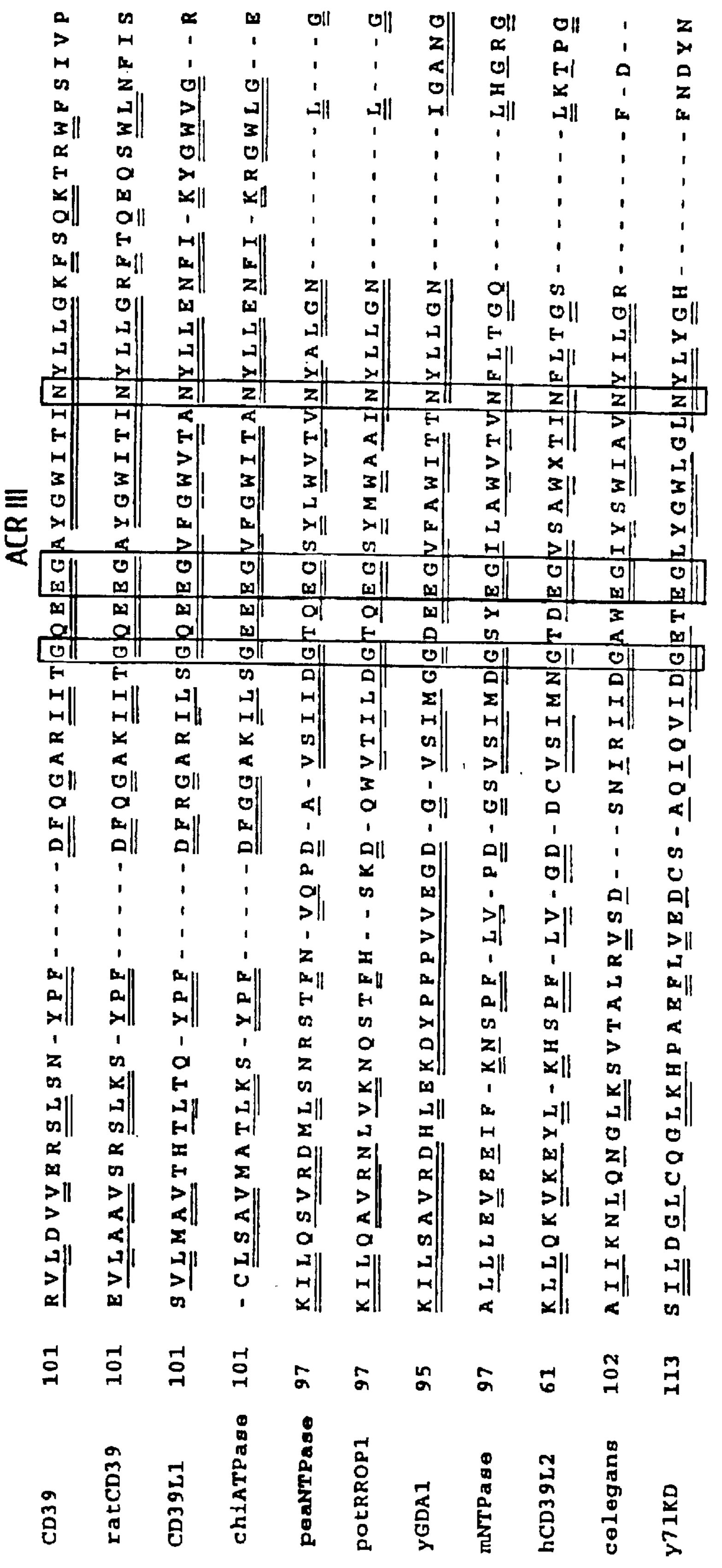

FIG. 3C

ACR IV

| | | | |
|---|---|---|---|
| CD39 | 155 | YETNNQETFGALD | LGGASTQVTFVPQNQ |
| ratCD39 | 155 | -DSQKQATFGALD | LGGSSTQVTFVPLNQ |
| CD39L1 | 152 | WFRPRKGTLGAMD | LGGASTQITFETTSP |
| chiATPase | 151 | WIQSKKKTLGAMD | FGGASTQITFETSDAI |
| peaNTPase | 144 | KKYTK---TVGVID | LGGGSVQMAYAVSKK |
| potRROP1 | 144 | KDYKS---TTATID | LGGGSVQMAYAISNE |
| yGDA1 | 146 | PKL-P---TAAVF | DLGGSTQIVFEPTFPI |
| mNTPase | 146 | QE------TVGTLD | LGGASTQITFLPQFE |
| hCD39L2 | 110 | GS------SVGMLD | LGGGSTQIAFLPRVE |
| celegans | 149 | KE-NDS-KVGMID | MGGASVQIAPEIA-NE |
| y71KD | 165 | PEVSDHPTFGPMD | MGGASTQIAF--APHDS |

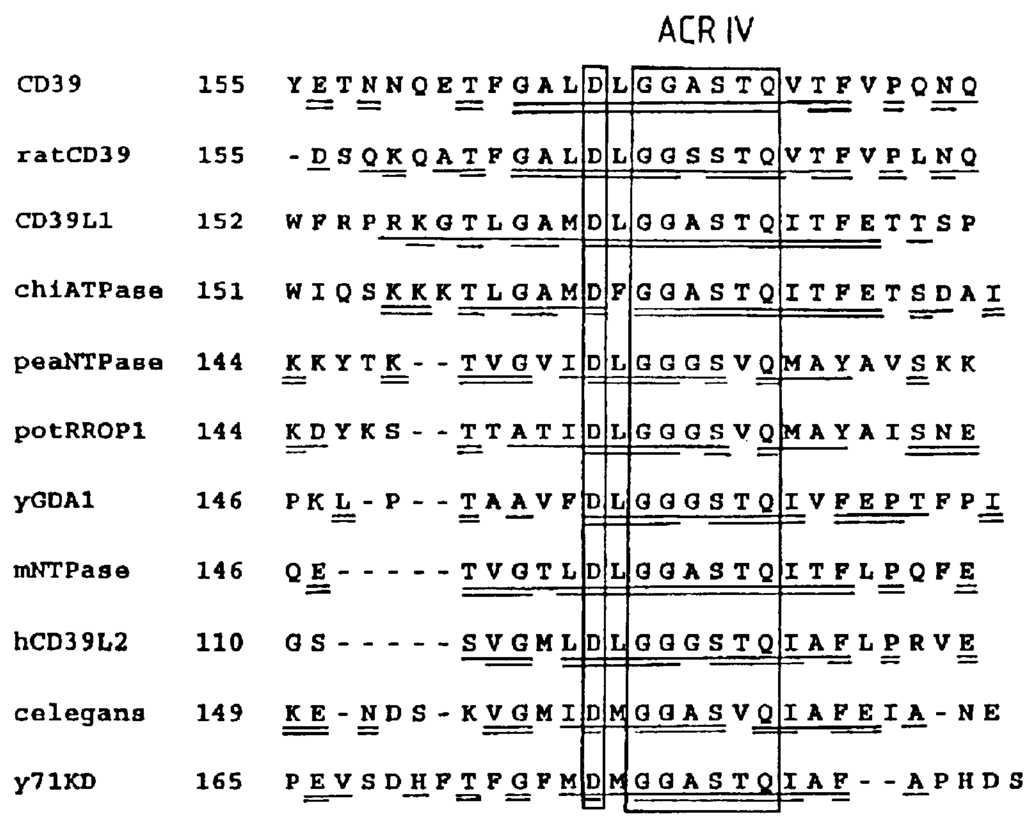

FIG. 3D

```
GTGGGGTCGT ATCCCGCGGG TGGAGGCCGG GGTGGCGCCG GCCGGGGCGG GGGAGCCCAA 60

AAGACCGGCT GCCGCCTGCT CCCCGGAAAA GGGCACTCGT CTCCGTGGGT GTGGCGGAGC 120

GCGCGGTGCA TGGAATGGGC TATGTGAATG AAAAAAGGTA TCCGTTATGA AACTTCCAGA 180

AAAACGAGCT ACATTTTTCA GCAGCCGCAG CACGGTCCTT GGCAAACAAG G ATG AGA  237
                                                        Met Arg
                                                          1

AAA ATA TCC AAC CAC GGG AGC CTG CGG GTG GCG AAG GTG GCA TAC CCC   285
Lys Ile Ser Asn His Gly Ser Leu Arg Val Ala Lys Val Ala Tyr Pro
             5                  10                  15

CTG GGG CTG TGT GTG GGC GTG TTC ATC TAT GTT GCC TAC ATC AAG TGG   333
Leu Gly Leu Cys Val Gly Val Phe Ile Tyr Val Ala Tyr Ile Lys Trp
     20                  25                  30

CAC CGG GCC ACC GCC ACC CAG GCC TTC TTC AGC ATC ACC AGG GCA GCC   381
His Arg Ala Thr Ala Thr Gln Ala Phe Phe Ser Ile Thr Arg Ala Ala
 35                  40                  45                  50
```

FIG. 4A

```
CCG GGG GCC CGG TGG GGT CAG CAG GCC CAC AGC CCC CTG GGG ACA GCT    429
Pro Gly Ala Arg Trp Gly Gln Gln Ala His Ser Pro Leu Gly Thr Ala
                 55                  60                  65

GCA GAC GGG CAC GAG GTC TTC TAC GGG ATC ATG TTT GAT GCA GGA AGC    477
Ala Asp Gly His Glu Val Phe Tyr Gly Ile Met Phe Asp Ala Gly Ser
             70                  75                  80

ACT GGC ACC CGA GTA CAC GTC TTC CAG TTC ACC CGG CCC CCC AGA GAA    525
Thr Gly Thr Arg Val His Val Phe Gln Phe Thr Arg Pro Pro Arg Glu
         85                  90                  95

ACT CCC ACG TTA ACC CAC GAA ACC TTC AAA GCA GTG AAG CCA GGT CTT    573
Thr Pro Thr Leu Thr His Glu Thr Phe Lys Ala Val Lys Pro Gly Leu
    100                 105                 110

TCT GCC TAT GCT GAT GAT GTT GAA AAG AGC GCT CAG GGA ATC CGG GAA    621
Ser Ala Tyr Ala Asp Asp Val Glu Lys Ser Ala Gln Gly Ile Arg Glu
115                 120                 125                 130
```

FIG. 4B

```
CTA CTG GAT GTT GCT AAA CAG GAC ATT CCG TTC GAC TTC TGG AAG GCC   669
Leu Leu Asp Val Ala Lys Gln Asp Ile Pro Phe Asp Phe Trp Lys Ala
                135                 140                 145

ACC CCT CTG GTC CTC AAG GCC ACA GCT GGC TTA CGC CTG TTA CCT GGA   717
Thr Pro Leu Val Leu Lys Ala Thr Ala Gly Leu Arg Leu Leu Pro Gly
            150                 155                 160

GAA AAG GCC CAG AAG TTA CTG CAG AAG GTG AAA GAA GTA TTT AAA GCA   765
Glu Lys Ala Gln Lys Leu Leu Gln Lys Val Lys Glu Val Phe Lys Ala
        165                 170                 175

TCG CCT TTC CTT GTA GGG GAT GAC TGT GTT TCC ATC ATG AAC GGA ACA   813
Ser Pro Phe Leu Val Gly Asp Asp Cys Val Ser Ile Met Asn Gly Thr
    180                 185                 190

GAT GAA GGC GTT TCG GCG TGG ATC ACC ATC AAC TTC CTG ACA GGC AGC   861
Asp Glu Gly Val Ser Ala Trp Ile Thr Ile Asn Phe Leu Thr Gly Ser
195                 200                 205                 210

TTG AAA ACT CCA GGA GGG AGC AGC GTG GGC ATG CTG GAC TTG GGC GGA   909
Leu Lys Thr Pro Gly Gly Ser Ser Val Gly Met Leu Asp Leu Gly Gly
                215                 220                 225
```

FIG. 4C

```
GGA TCC ACT CAG ATC GCC TTC CTG CCA CGC GTG GAG GGC ACC CTG CAG    957
Gly Ser Thr Gln Ile Ala Phe Leu Pro Arg Val Glu Gly Thr Leu Gln
            230                 235                 240

GCC TCC CCA CCC GGC TAC CTG ACG GCA CTG CGG ATG TTT AAC AGG ACC   1005
Ala Ser Pro Pro Gly Tyr Leu Thr Ala Leu Arg Met Phe Asn Arg Thr
        245                 250                 255

TAC AAG CTC TAT TCC TAC AGC TAC CTC GGG CTC GGG CTG ATG TCG GCA   1053
Tyr Lys Leu Tyr Ser Tyr Ser Tyr Leu Gly Leu Gly Leu Met Ser Ala
    260                 265                 270

CGC CTG GCG ATC CTG GGC GGC GTG GAG GGG CAG CCT GCT AAG GAT GGA   1101
Arg Leu Ala Ile Leu Gly Gly Val Glu Gly Gln Pro Ala Lys Asp Gly
275                 280                 285                 290

AAG GAG TTG GTC AGC CCT TGC TTG TCT CCC AGT TTC AAA GGA GAG TGG   1149
Lys Glu Leu Val Ser Pro Cys Leu Ser Pro Ser Phe Lys Gly Glu Trp
                295                 300                 305

GAA CAC GCA GAA GTC ACG TAC AGG GTT TCA GGG CAG AAA GCA GCG GCA   1197
Glu His Ala Glu Val Thr Tyr Arg Val Ser Gly Gln Lys Ala Ala Ala
            310                 315                 320
```

FIG. 4D

```
AGC CTG CAC GAG CTG TGT GCT GCC AGA GTG TCA GAG GTC CTT CAA AAC   1245
Ser Leu His Glu Leu Cys Ala Ala Arg Val Ser Glu Val Leu Gln Asn
        325                 330                 335

AGA GTG CAC AGG ACG GAG GAA GTG AAG CAT GTG GAC TTC TAT GCT TTC   1293
Arg Val His Arg Thr Glu Glu Val Lys His Val Asp Phe Tyr Ala Phe
    340                 345                 350

TCC TAC TAT TAC GAC CTT GCA GCT GGT GTG GGC CTC ATA GAT GCG GAG   1341
Ser Tyr Tyr Tyr Asp Leu Ala Ala Gly Val Gly Leu Ile Asp Ala Glu
355                 360                 365                 370

AAG GGA GGC AGC CTG GTG GTG GGG GAC TTC GAG ATC GCA GCC AAG TAC   1389
Lys Gly Gly Ser Leu Val Val Gly Asp Phe Glu Ile Ala Ala Lys Tyr
                375                 380                 385

GTG TGT CGG ACC CTG GAG ACA CAG CCG CAG AGC AGC CCC TTC TCA TGC   1437
Val Cys Arg Thr Leu Glu Thr Gln Pro Gln Ser Ser Pro Phe Ser Cys
            390                 395                 400

ATG GAC CTC ACC TAC GTC AGC CTG CTA CTC CAG GAG TTC GGC TTT CCC   1485
Met Asp Leu Thr Tyr Val Ser Leu Leu Leu Gln Glu Phe Gly Phe Pro
        405                 410                 415
```

FIG. 4E

```
AGG AGC AAA GTG CTG AAG CTC ACT CGG AAA ATT GAC AAT GTT GAG ACC   1533
Arg Ser Lys Val Leu Lys Leu Thr Arg Lys Ile Asp Asn Val Glu Thr
    420                 425                 430

AGC TGG GCT CTG GGG GCC ATT TTT CAT TAC ATC GAC TCC CTG AAC AGA   1581
Ser Trp Ala Leu Gly Ala Ile Phe His Tyr Ile Asp Ser Leu Asn Arg
435                 440                 445                 450

CAG AAG AGT CCA GCC TCA TAGTGGCCGA GCCATCCCTG TCCCCGTCAG          1629
Gln Lys Ser Pro Ala Ser
                455

CAGTGTCTGT GTGTCTGCAT AAACCCTCCT GTCCTGGACG TGACTTCATC CTGAGGAGCC 1689

ACAGCACAGG CCGTGCTGGC ACTTTCTGCA CACTGGCTCT GGGACTTGCA GAAGGCCTGG 1749

TGCTGCCCTG GCATCAGCCT CTTCCAGTCA CATCTGGCCA GAGGGCTGTC TGGACCTGGG 1809

CCCTGCTCAA TGCCACCTGT CTGCCTGGGC TCCAAGTGGG CAGGACCAGG ACAGAACCAC 1869

AGGCACACAC TGAGGGGGCA GTGTGGCTCC CTGCCTGTCC CATCCCCATG CCCCGTCCGC 1929
```

FIG. 4F

```
GGGGCTGTGG CTGCTGCTGT GCATGTCCCT GCGATGGGAG TCTTGTCTCC CAGCCTGTCA 1989
GTTTCCTCCC CAGGGCAGAG CTCCCCTTCC TGCAAGAGTC TGGGAGGCGG TGCAGGCTGT 2049
CCTGGCTGCT CTGGGGAAGC CGAGGGACAG CCATAACACC CCCGGGACAG TAGGTCTGGG 2109
CGGCACCACT GGGAACTCTG GACTTGAGTG TGTTTGCTCT TCCTTGGGTA TGAATGTGTG 2169
AGTTCACCCA GAGGCCTGCT CTCCTCACAC ATTGTGTGGT TTGGGGTTAA TGATGGAGGG 2229
AGACACCTCT TCATAGACGG CAGGTGCCCA CCTTTCAGGG AGTCTCCCAG CATGGGCGGA 2289
TGCCGGGCAT GAGCTGCTGT AAACTATTTG TGGCTGTGCT GCTTGAGTGA CGTCTCTGTC 2349
GTGTGGGTGC CAAGTGCTTG TGTAGAAACT GTGTTCTGAG CCCCCTTTTC TGGACACCAA 2409
CTGTGTCCTG TGAATGTATC GCTACTGTGA GCTGTTCCCG CCTAGCCAGG GCCATGTCTT 2469
AGGTGCAGCT GTGCCACGGG TCAGCTGAGC CACAGTCCCA GAACCAAGCT CTCGGTGTCT 2529
```

FIG. 4G

```
CGGGCCACCA TCCGCCCACC TCGGGCTGAC CCCACCTCCT CCATGGACAG TGTGAGCCCC 2589
GGGCCGTGCA TCCTGCTCAG TGTGGCGTCA GTGTCGGGGC TGAGCCCCTT GAGCTGCTTC 2649
AGTGAATGTA CAGTGCCCGG CACGAGCTGA ACCTCATGTG TTCCACTCCC AATAAAAGGT 2709
TGACAGGGGC TTCTCCTTCA AAAAAAAAAA AAAAAAAAAA AAAAAAAAAA AAA        2762
```

FIG. 4H

```
ACCCACGCGT CTGGCCGCGG GCCGCCTCTG CGGCAGCGCT AGTCGCCTTC TCCGAATCGG 60

CTCCGCACAG CTAGGAGAAA AG ATG TTC ACT GTG CTG ACC CGC CAA CCA TGT  112
                         Met Phe Thr Val Leu Thr Arg Gln Pro Cys
                          1               5                  10

GAG CAA GCA GGC CTC AAG GCC CTC TAC CGA ACT CCA ACC ATC ATT GCC   160
Glu Gln Ala Gly Leu Lys Ala Leu Tyr Arg Thr Pro Thr Ile Ile Ala
                15                  20                  25

TTG GTG GTC TTG CTT GTG AGT ATT GTG GTA CTT GTG AGT ATC ACT GTC   208
Leu Val Val Leu Leu Val Ser Ile Val Val Leu Val Ser Ile Thr Val
            30                  35                  40

ATC CAG ATC CAC AAG CAA GAG GTC CTC CCT CCA GGA CTG AAG TAT GGT   256
Ile Gln Ile His Lys Gln Glu Val Leu Pro Pro Gly Leu Lys Tyr Gly
        45                  50                  55

ATT GTG CTG GAT GCC GGG TCT TCA AGA ACC ACA GTC TAC GTG TAT CAA   304
Ile Val Leu Asp Ala Gly Ser Ser Arg Thr Thr Val Tyr Val Tyr Gln
    60                  65                  70
```

FIG. 6A

```
TGG CCA GCA GAA AAA GAG AAT AAT ACC GGA GTG GTC AGT CAA ACC TTC   352
Trp Pro Ala Glu Lys Glu Asn Asn Thr Gly Val Val Ser Gln Thr Phe
 75                 80                  85                  90

AAA TGT AGT GTG AAA GGC TCT GGA ATC TCC AGC TAT GGA AAT AAC CCC   400
Lys Cys Ser Val Lys Gly Ser Gly Ile Ser Ser Tyr Gly Asn Asn Pro
                 95                 100                 105

caa gat gtc ccc aga gcc ttt gag gag tgt atg caa aaa gtc aag ggg   448
Gln Asp Val Pro Arg Ala Phe Glu Glu Cys Met Gln Lys Val Lys Gly
            110                 115                 120

CAG GTT CCA TCC CAC CTC CAC GGA TCC ACC CCC ATT CAC CTG GGA GCC   496
Gln Val Pro Ser His Leu His Gly Ser Thr Pro Ile His Leu Gly Ala
        125                 130                 135

ACG GCT GGG ATG CGC TTG CTG AGG TTG CAA AAT GAA ACA GCA GCT AAT   544
Thr Ala Gly Met Arg Leu Leu Arg Leu Gln Asn Glu Thr Ala Ala Asn
    140                 145                 150

GAA GTC CTT GAA AGC ATC CAA AGC TAC TTC AAG TCC CAG CCC TTT GAC   592
Glu Val Leu Glu Ser Ile Gln Ser Tyr Phe Lys Ser Gln Pro Phe Asp
155                 160                 165                 170
```

FIG. 6B

```
TTT AGG GGT GCT CAA ATC ATT TCT GGG CAA GAA GAA GGG GTA TAT GGA    640
Phe Arg Gly Ala Gln Ile Ile Ser Gly Gln Glu Glu Gly Val Tyr Gly
                175                 180                 185

TGG ATT ACA GCC AAC TAT TTA ATG GGA AAT TTC CTG GAG AAG AAC CTG    688
Trp Ile Thr Ala Asn Tyr Leu Met Gly Asn Phe Leu Glu Lys Asn Leu
            190                 195                 200

TGG CAC ATG TGG GTG CAC CCG CAT GGA GTG GAA ACC ACG GGT GCC CTG    736
Trp His Met Trp Val His Pro His Gly Val Glu Thr Thr Gly Ala Leu
        205                 210                 215

GAC TTA GGT GGT GCC TCC ACC CAA ATA TCC TTC GTG GCA GGA GAG AAG    784
Asp Leu Gly Gly Ala Ser Thr Gln Ile Ser Phe Val Ala Gly Glu Lys
    220                 225                 230

ATG GAT CTG AAC ACC AGC GAC ATC ATG CAG GTG TCC CTG TAT GGC TAC    832
Met Asp Leu Asn Thr Ser Asp Ile Met Gln Val Ser Leu Tyr Gly Tyr
235                 240                 245                 250

GTA TAC ACG CTC TAC ACA CAC AGC TTC CAG TGC TAT GGC CGG AAT GAG    880
Val Tyr Thr Leu Tyr Thr His Ser Phe Gln Cys Tyr Gly Arg Asn Glu
                255                 260                 265
```

FIG. 6C

```
GCT GAG AAG AAG TTT CTG GCA ATG CTC CTG CAG AAT TCT CCT ACC AAA    928
Ala Glu Lys Lys Phe Leu Ala Met Leu Leu Gln Asn Ser Pro Thr Lys
            270                 275                 280

AAC CAT CTC ACC AAT CCC TGT TAC CCT CGG GAT TAT AGC ATC AGC TTC    976
Asn His Leu Thr Asn Pro Cys Tyr Pro Arg Asp Tyr Ser Ile Ser Phe
        285                 290                 295

ACC ATG GGC CAT GTA TTT GAT AGC CTG TGC ACT GTG GAC CAG AGG CCA   1024
Thr Met Gly His Val Phe Asp Ser Leu Cys Thr Val Asp Gln Arg Pro
    300                 305                 310

GAA AGT TAT AAC CCC AAT GAT GTC ATC ACT TTT GAA GGA ACT GGG GAC   1072
Glu Ser Tyr Asn Pro Asn Asp Val Ile Thr Phe Glu Gly Thr Gly Asp
315                 320                 325                 330

CCA TCT CTG TGT AAG GAG AAG GTG GCT TCC ATA TTT GAC TTC AAA GCT   1120
Pro Ser Leu Cys Lys Glu Lys Val Ala Ser Ile Phe Asp Phe Lys Ala
                335                 340                 345

TGC CAT GAT CAA GAA ACC TGT TCT TTT GAT GGG GTT TAT CAG CCA AAG   1168
Cys His Asp Gln Glu Thr Cys Ser Phe Asp Gly Val Tyr Gln Pro Lys
            350                 355                 360
```

FIG. 6D

```
ATT AAA GGG CCA TTT GTG GCT TTT GCA GGA TTC TAC TAC ACA GCC AGT   1216
Ile Lys Gly Pro Phe Val Ala Phe Ala Gly Phe Tyr Tyr Thr Ala Ser
        365                 370                 375

GCT TTA AAT CTT TCA GGT AGC TTT TCC CTG GAC ACC TTC AAC TCC AGC   1264
Ala Leu Asn Leu Ser Gly Ser Phe Ser Leu Asp Thr Phe Asn Ser Ser
    380                 385                 390

ACC TGG AAT TTC TGC TCA CAG AAT TGG AGT CAG CTC CCA CTG CTG CTC   1312
Thr Trp Asn Phe Cys Ser Gln Asn Trp Ser Gln Leu Pro Leu Leu Leu
395                 400                 405                 410

CCC AAA TTT GAT GAG GTA TAT GCC CGC TCT TAC TGC TTC TCA GCC AAC   1360
Pro Lys Phe Asp Glu Val Tyr Ala Arg Ser Tyr Cys Phe Ser Ala Asn
                415                 420                 425

TAC ATC TAC CAC TTG TTT GTG AAC GGT TAC AAA TTC ACA GAG GAG ACT   1408
Tyr Ile Tyr His Leu Phe Val Asn Gly Tyr Lys Phe Thr Glu Glu Thr
            430                 435                 440

TGG CCC CAA ATA CAC TTT GAA AAA GAA GTG GGG AAT AGC AGC ATA GCC   1456
Trp Pro Gln Ile His Phe Glu Lys Glu Val Gly Asn Ser Ser Ile Ala
        445                 450                 455
```

FIG. 6E

```
TGG TCT CTT GGC TAC ATG CTC AGC CTG ACC AAC CAG ATC CCA GCT GAA    1504
Trp Ser Leu Gly Tyr Met Leu Ser Leu Thr Asn Gln Ile Pro Ala Glu
    460                 465                     470

AGC CCT CTG ATC CGT CTG CCC ATA GAA CCA CCT GTC TTT GTG GGC ACC    1552
Ser Pro Leu Ile Arg Leu Pro Ile Glu Pro Pro Val Phe Val Gly Thr
475                 480                     485                 490

CTC GCT TTC TTC ACA GTG GCA GCC TTG CTG TGT CTG GCA TTT CTT GCA    1600
Leu Ala Phe Phe Thr Val Ala Ala Leu Leu Cys Leu Ala Phe Leu Ala
                495                     500                 505

TAC CTG TGT TCA GCA ACC AGA AGA AAG AGG CAC TCC GAG CAT GCC TTT    1648
Tyr Leu Cys Ser Ala Thr Arg Arg Lys Arg His Ser Glu His Ala Phe
            510                 515                     520

GAC CAT GCA GTG GAT TCT GAC TGAGCCTTCA AAGCAGCTCC TGGAGTCCAA       1699
Asp His Ala Val Asp Ser Asp
        525

TGGCTGCTTA GAGTCAGCCT GGGTGGCACC AGGCAATGCA GGTGAAGTGG CTGCCTTCAG 1759
```

FIG. 6F

GAAATACAAC TAACTAAAAT CAAACACCTA GGTCACGTGC CTCTCAAATA CTGATTTCTG 1819

CCACAGCACC TCTTGAGGCA TCCCTTGGCT ATTCTGTGCA TATTGTTCTT CAGAGACCTC 1879

ACTACCCACA TGCTGATCTA TTGGGGAACA GAGAAGAGAC AGGCCACTAA GGTCAGGCTC 1939

TTTATATTAA GTTCCCCAGA GGAAGAGTAA GTTGAGAAGG TATCAGTTTA ATGTTGAAGA 1999

ATTGACCTCA GGGCTCAGTT TCCATTTCCC TCCCTCAGTA TTCTTCCTGG CAAGATACCC 2059

ATTAAGCATT TCGCCAATCA GAATCTCATT TTATAGTTTT TCCCATTGGT CTTTAACTAA 2119

GACTTTCTTG TAGCAATCTC GTAAGCAGTG AACCCCCTCA GATCAGTAGA ATATAGTATC 2179

TGGGGGAGAA GACTTACTTC CTTCAGGGCA GCAGCCACAG CCAGGCTTCT GTCATACAGG 2239

TAGATCCCGA AGCACAGAGA CATAAAAAAG GTCTCCCAGA AAACTATAGA CCATTCTCCA 2299

AGTGGAATTC CCACTTAGGG CTCTGGTCAC TAGATTGCAA CCTGTGTGTT TGTCATCATC 2359

CTCATCTCAC CATTGTATTG CTATGCCCTC CCATAAAAAC ACATTGATCC CTAGCAAGAT 2419

FIG. 6G

```
TATTGCATTC CAGATTTTAC TGCCTTTGCT AGGCTTTTGC TTAGCAAAGG GCTGACTTTC 2479
CATTGTTATC ATGGTGTATA TATTTTTGTC ACCATTCCCA CAAGTATACT TGATGTTGTC 2539
ATAGAACGAA CATCCTACTC TATGATTTAC TAACCAATTA CTTTCCCAGA TCATAGACCT 2599
CTCTGCATAG TAGTCATAGG TCTTGACTTT GGGGAAAGAA AAGGAAGCTG CAGGAATATT 2659
TATCTCCAAA GTCGAATGAG AAAGAACTCC AGCAAATCCA ATGGCTACAA ACTAAAAATC 2719
AGCATTATTT CATATTGCTG TTTCTTAGCT GAATATGGAA TAAAGAACTA TTATTTTATT 2779
TTGAAAAAAA AAAAAAAA                                               2797
```

FIG. 6H

```
GCGCGCGCGT TTTCCTTGTT CCTGGTCAAC AAAGAAATGT GGAGTGTCTT GGCTGAATCC 60

TCATACAGAC AAGATCATTA TGGTGCTGTT AGGTAGGACT TGTATCCAGA TGTAAGGTTG 120

AAAAAGTGAT ATAATAAAGG AACCAAGGAG AAAATTCAGA AGGAAAGAAA AAATTGCCTC 180

TGCAGGTGTG CGAGCAGGAT TGCTTCTGCA ACAAAAGCCT CCACCCAGCC ACATCTTGGG 240

AAAAGA ATG GCC ACT TCT TGG GGC ACA GTC TTT TTC ATG CTG GTG GTA     288
       Met Ala Thr Ser Trp Gly Thr Val Phe Phe Met Leu Val Val
        1               5                   10

TCC TGT GTT TGC AGC GCT GTC TCC CAC AGG AAC CAG CAG ACT TGG TTT     336
Ser Cys Val Cys Ser Ala Val Ser His Arg Asn Gln Gln Thr Trp Phe
 15                  20                  25                  30

GAG GGT ATC TTC CTG TCT TCC ATG TGC CCC ATC AAT GTC AGC GCC AGC     384
Glu Gly Ile Phe Leu Ser Ser Met Cys Pro Ile Asn Val Ser Ala Ser
                35                  40                  45

ACC TTG TAT GGA ATT ATG TTT GAT GCA GGG AGC ACT GGA ACT CGA ATT     432
Thr Leu Tyr Gly Ile Met Phe Asp Ala Gly Ser Thr Gly Thr Arg Ile
            50                  55                  60
```

FIG. 7A

```
CAT GTT TAC ACC TTT GTG CAG AAA ATG CCA GGA CAG CTT CCA ATT CTA    480
His Val Tyr Thr Phe Val Gln Lys Met Pro Gly Gln Leu Pro Ile Leu
         65                  70                  75

GAA GGG GAA GTT TTT GAT TCT GTG AAG CCA GGA CTT TCT GCT TTT GTA    528
Glu Gly Glu Val Phe Asp Ser Val Lys Pro Gly Leu Ser Ala Phe Val
     80                  85                  90

GAT CAA CCT AAG CAG GGT GCT GAG ACC GTT CAA GGG CTC TTA GAG GTG    576
Asp Gln Pro Lys Gln Gly Ala Glu Thr Val Gln Gly Leu Leu Glu Val
 95                 100                 105                 110

GCC AAA GAC TCA ATC CCC CGA AGT CAC TGG AAA AAG ACC CCA GTG GTC    624
Ala Lys Asp Ser Ile Pro Arg Ser His Trp Lys Lys Thr Pro Val Val
                115                 120                 125

CTA AAG GCA ACA GCA GGA CTA CGC TTA CTG CCA GAA CAC AAA GCC AAG    672
Leu Lys Ala Thr Ala Gly Leu Arg Leu Leu Pro Glu His Lys Ala Lys
            130                 135                 140

GCT CTG CTC TTT GAG GTA AAG GAG ATC TTC AGG AAG TCA CCT TTC CTG    720
Ala Leu Leu Phe Glu Val Lys Glu Ile Phe Arg Lys Ser Pro Phe Leu
        145                 150                 155
```

FIG. 7B

```
GTA CCA AAG GGC AGT GTT AGC ATC ATG GAT GGA TCC GAC GAA GGC ATA    768
Val Pro Lys Gly Ser Val Ser Ile Met Asp Gly Ser Asp Glu Gly Ile
    160                 165                 170

TTA GCT TGG GTT ACT GTG AAT TTT CTG ACA GGT CAG CTG CAT GGC CAC    816
Leu Ala Trp Val Thr Val Asn Phe Leu Thr Gly Gln Leu His Gly His
175                 180                 185                 190

AGA CAG GAG ACT GTG GGG ACC TTG GAC CTA GGG GGA GCC TCC ACC CAA    864
Arg Gln Glu Thr Val Gly Thr Leu Asp Leu Gly Gly Ala Ser Thr Gln
                195                 200                 205

ATC ACG TTC CTG CCC CAG TTT GAG AAA ACT CTG GAA CAA ACT CCT AGG    912
Ile Thr Phe Leu Pro Gln Phe Glu Lys Thr Leu Glu Gln Thr Pro Arg
            210                 215                 220

GGC TAC CTC ACT TCC TTT GAG ATG TTT AAC AGC ACT TAT AAG CTC TAT    960
Gly Tyr Leu Thr Ser Phe Glu Met Phe Asn Ser Thr Tyr Lys Leu Tyr
        225                 230                 235

ACA CAT AGT TAC TTG GGA TTT GGA TTG AAA GCT GCA AGA CTA GCA ACC   1008
Thr His Ser Tyr Leu Gly Phe Gly Leu Lys Ala Ala Arg Leu Ala Thr
    240                 245                 250
```

FIG. 7C

CTG GGA GCC CTG GAG ACA GAA GGG ACT GAT GGG CAC ACT TTC CGG AGT 1056
Leu Gly Ala Leu Glu Thr Glu Gly Thr Asp Gly His Thr Phe Arg Ser
255 260 265 270

GCC TGT TTA CCG AGA TGG TTG GAA GCA GAG TGG ATC TTT GGG GGT GTG 1104
Ala Cys Leu Pro Arg Trp Leu Glu Ala Glu Trp Ile Phe Gly Gly Val
275 280 285

AAA TAC CAG TAT GGT GGC AAC CAA GAA GGG GAG GTG GGC TTT GAG CCC 1152
Lys Tyr Gln Tyr Gly Gly Asn Gln Glu Gly Glu Val Gly Phe Glu Pro
290 295 300

TGC TAT GCC GAA GTG CTG AGG GTG GTA CGA GGA AAA CTT CAC CAG CCA 1200
Cys Tyr Ala Glu Val Leu Arg Val Val Arg Gly Lys Leu His Gln Pro
305 310 315

GAG GAG GTC CAG AGA GGT TCC TTC TAT GCT TTC TCT TAC TAT TAT GAC 1248
Glu Glu Val Gln Arg Gly Ser Phe Tyr Ala Phe Ser Tyr Tyr Tyr Asp
320 325 330

CGA GCT GTT GAC ACA GAC ATG ATT GAT TAT GAA AAG GGG GGT ATT TTA 1296
Arg Ala Val Asp Thr Asp Met Ile Asp Tyr Glu Lys Gly Gly Ile Leu
335 340 345 350

FIG. 7D

```
AAA GTT GAA GAT TTT GAA AGA AAA GCC AGG GAA GTG TGT GAT AAC TTG   1344
Lys Val Glu Asp Phe Glu Arg Lys Ala Arg Glu Val Cys Asp Asn Leu
                355                 360                 365

GAA AAC TTC ACC TCA GGC AGT CCT TTC CTG TGC ATG GAT CTC AGC TAC   1392
Glu Asn Phe Thr Ser Gly Ser Pro Phe Leu Cys Met Asp Leu Ser Tyr
            370                 375                 380

ATC ACA GCC CTG TTA AAG GAT GGC TTT GGC TTT GCA GAC AGC ACA GTC   1440
Ile Thr Ala Leu Leu Lys Asp Gly Phe Gly Phe Ala Asp Ser Thr Val
        385                 390                 395

TTA CAG CTC ACA AAG AAA GTG AAC AAC ATA GAG ACG GGC TGG GCC TTG   1488
Leu Gln Leu Thr Lys Lys Val Asn Asn Ile Glu Thr Gly Trp Ala Leu
    400                 405                 410

GGG GCC ACC TTT CAC CTG TTG CAG TCT CTG GGC ATC TCC CAT           1530
Gly Ala Thr Phe His Leu Leu Gln Ser Leu Gly Ile Ser His
415                 420                 425

TGAGGCCACG TACTTCCTTG GAGACCTGCA TTTGCCAACA CCTTTTTAAG GGGAGGAGAG 1590
```

FIG. 7E

```
AGCACTTAGT TTCTGAACTA GTCTGGGACA TCCTGGACTT GAGCCTAGAG ATTTAGGTTT 1650
AATTAATTTT ACACATCTAA TGTGAACTGC TGCCTAACCA CTCAAGAGTA CACAGCTGGC 1710
ACCAGAGCAT CACAGAGAGC CCTGTGAGCC AAAAAGTATA GTTTTGGAAC TTAACCTTGG 1770
AGTGAGAGCC CAGGGACAGG TCCCTGGAAA CCAAAGAAAA ATCGCATTTC AACCCTTTGA 1830
GTGCCTCATT CCACTGAATA TTTAAATTTT CCTCTTAAAT GGTAAACTGA CTTATTGCAA 1890
TCCCAAGACC CATCAATATC AGTATTTTTT TCCTCCCTAT ACAGTGCCCT GCCCACCCTT 1950
ATCTGCACCC ACCTCCCCTG AAAAAGAGAG AAAAAAAAAA AAAAAAAA             1998
```

FIG. 7F

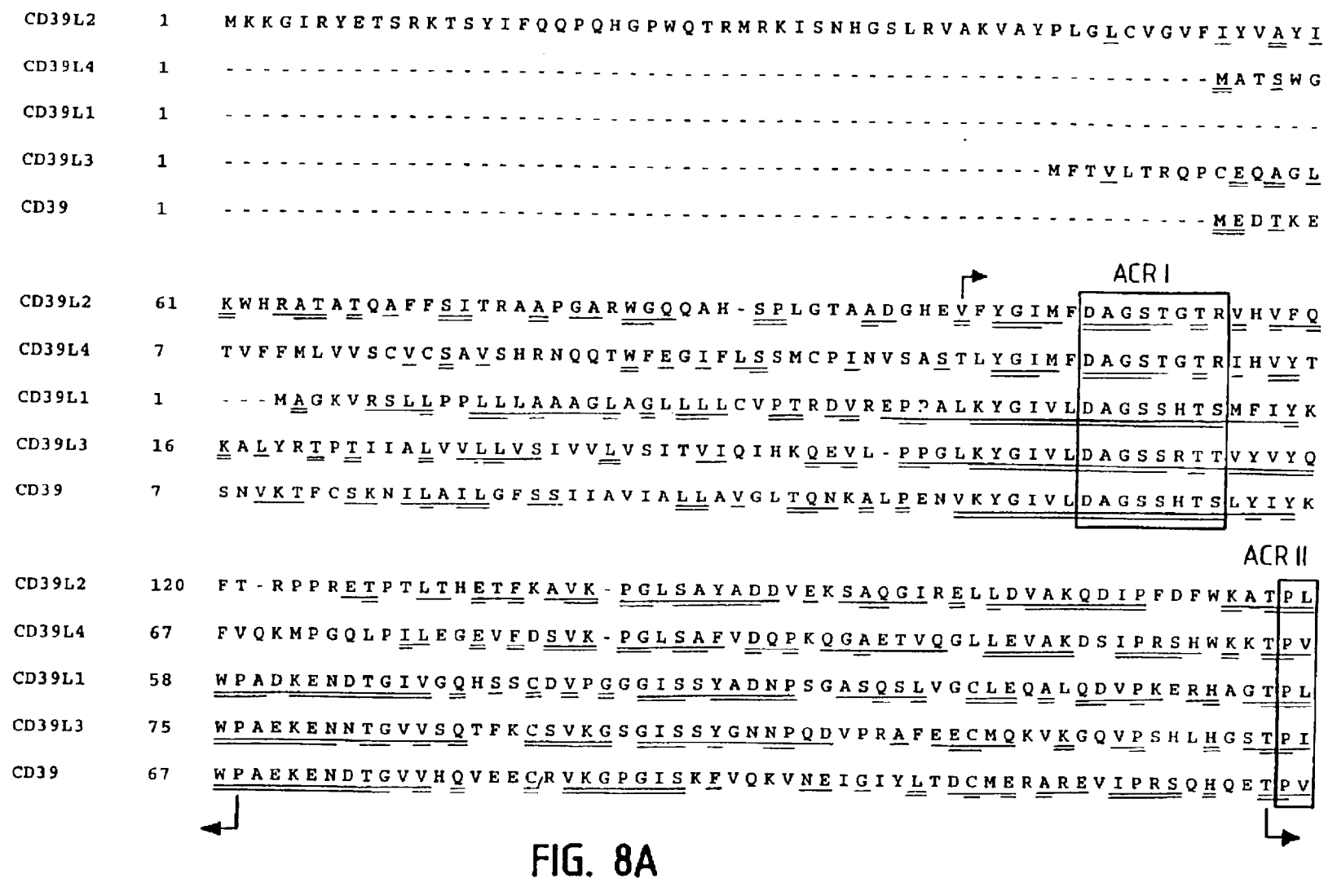

| | | |
|---|---|---|
| CD39L2 | 1 | MKKGIRYETSRKTSYIFQQPQHGPWQTRMRKISNHGSLRVAKVAYPLGLCVGVFIYVAYI |
| CD39L4 | 1 | ------------------------------------------------------MATSWG |
| CD39L1 | 1 | ------------------------------------------------------------ |
| CD39L3 | 1 | ---------------------------------------------MFTVLTRQPCEQAGL |
| CD39 | 1 | ------------------------------------------------------MEDTKE |

ACR I

| | | |
|---|---|---|
| CD39L2 | 61 | KWHRATATQAFFSITRAAPGARWGQQAH-SPLGTAADGHEVFYGIMFDAGSTGTRVHVFQ |
| CD39L4 | 7 | TVFFMLVVSCVCSAVSHRNQQTWFEGIFLSSMCPINVSASTLYGIMFDAGSTGTRIHVYT |
| CD39L1 | 1 | ---MAGKVRSLLPPLLLAAAGLAGLLLLCVPTRDVREP?ALKYGIVLDAGSSHTSMFIYK |
| CD39L3 | 16 | KALYRTPTIIALVVLLVSIVVLVSITVIQIHKQEVL-PPGLKYGIVLDAGSSRTTVYVYQ |
| CD39 | 7 | SNVKTFCSKNILAILGFSSIIAVIALLAVGLTQNKALPENVKYGIVLDAGSSHTSLYIYK |

ACR II

| | | |
|---|---|---|
| CD39L2 | 120 | FT-RPPRETPTLTHETFKAVK-PGLSAYADDVEKSAQGIRELLDVAKQDIPFDFWKATPL |
| CD39L4 | 67 | FVQKMPGQLPILEGEVFDSVK-PGLSAFVDQPKQGAETVQGLLEVAKDSIPRSHWKKTPV |
| CD39L1 | 58 | WPADKENDTGIVGQHSSCDVPGGGISSYADNPSGASQSLVGCLEQALQDVPKERHAGTPL |
| CD39L3 | 75 | WPAEKENNTGVVSQTFKCSVKGSGISSYGNNPQDVPRAFEECMQKVKGQVPSHLHGSTPI |
| CD39 | 67 | WPAEKENDTGVVHQVEECRVKGPGISKFVQKVNEIGIYLTDCMERAREVIPRSQHQETPV |

FIG. 8A

| | | |
|---|---|---|
| CD39L2 | 343 | VSGQKAAASLHELCAARVSEVLQNRVHRTEEVKHVDFYAFSYYYDLAAGVGLIDAEKGGS |
| CD39L4 | 290 | YGGNQEGEVGFEPCYAEVLRVVRGKLHQPEEVQRGSFYAFSYYYDRAVDTDMIDYEKGGI |
| CD39L1 | 283 | PCTMAQRPQNFNSSARVSLSGSSDPHLCRDLVSGLFSFSSC-PFSRCSFNGVFQPPVAGN |
| CD39L3 | 307 | LCTVDQRPESYNPNDVITFEGTGDPSLCKEKVASIFDFKACHDQETCSFDGVYQPKIKGP |
| CD39   | 300 | PCT---KRFEMTLPFQQFEIQGIGNYQQCHQSILELFNTSYC-PYSQCAFNGIFLPPLQGD |

| | | |
|---|---|---|
| CD39L2 | 403 | LVVGDFEIAAKYVCRTLETQPQSSPFSCMDLTYVSLLQE-FGFPRSKVLKLTRKIDNVE |
| CD39L4 | 350 | LKVEDFERKAREVCDNLENFTSGSPFLCMDLSYITALLKDGFGFADSTVLQLTKKVNNIE |
| CD39L1 | 342 | FV------APSAFFYTVDFLRTSMGLPVATLQQLEAAAVNVCNQTWAQ------ |
| CD39L3 | 367 | FV------AFAGFYYTASALNLSGSF---SLDTFNSSTWNFCSQNWSQLPLLLPKFDEVY |
| CD39   | 357 | FG------AFSAFYFVMKFLNLTS--EKVSQEKVTEMMKKFCAQPWEEIKTSYAGVKEKY |

| | | |
|---|---|---|
| CD39L2 | 462 | TSWALGAIFHYIDSLNRQKSPAS* |
| CD39L4 | 410 | TGWALGATFHLLQSLGISH |
| CD39L1 | 384 | --------QLLSRGYGFDERAFGGVIFQKKAADTAVGWALGYMLNTNLIPADPPG |
| CD39L3 | 418 | ARSYCFSANYIYHLFVNGYKFTEETWPQIHFEKEVGNSSIAWSLGYMLSLTNQIPAESPL |
| CD39   | 409 | LSEYCFSGTYILSLLLQGYHFTADSWEHIHFIGKIQGSDAGWTLGYMLNLTNMIPAEQP- |

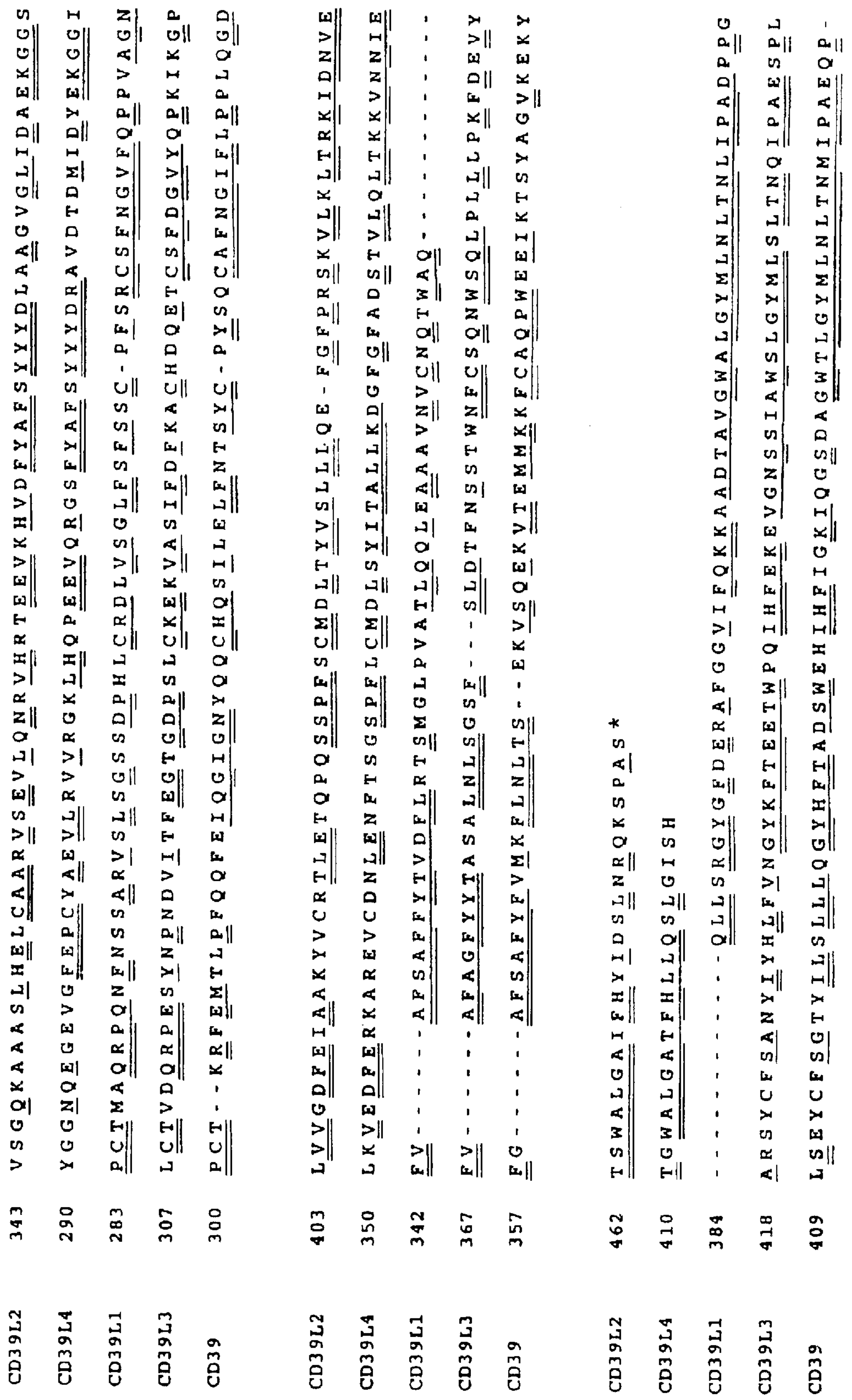

```
CD39L2   485
CD39L4   429
CD39L1   432  L R K G T D F S S W V V L L L L F A S A L L A A L V L L L R Q V H S A K L P S T I *
CD39L3   478  I R L P I E P P V F V G T L A F F T V A A L L C L A F L A Y L C S A T R R K R H S E H A F D H A V D S D *
CD39     468  L S T P L S H S T Y V F L M V L F S L V L F T V A I I G L L I F H K P S Y F W K D M V *
```

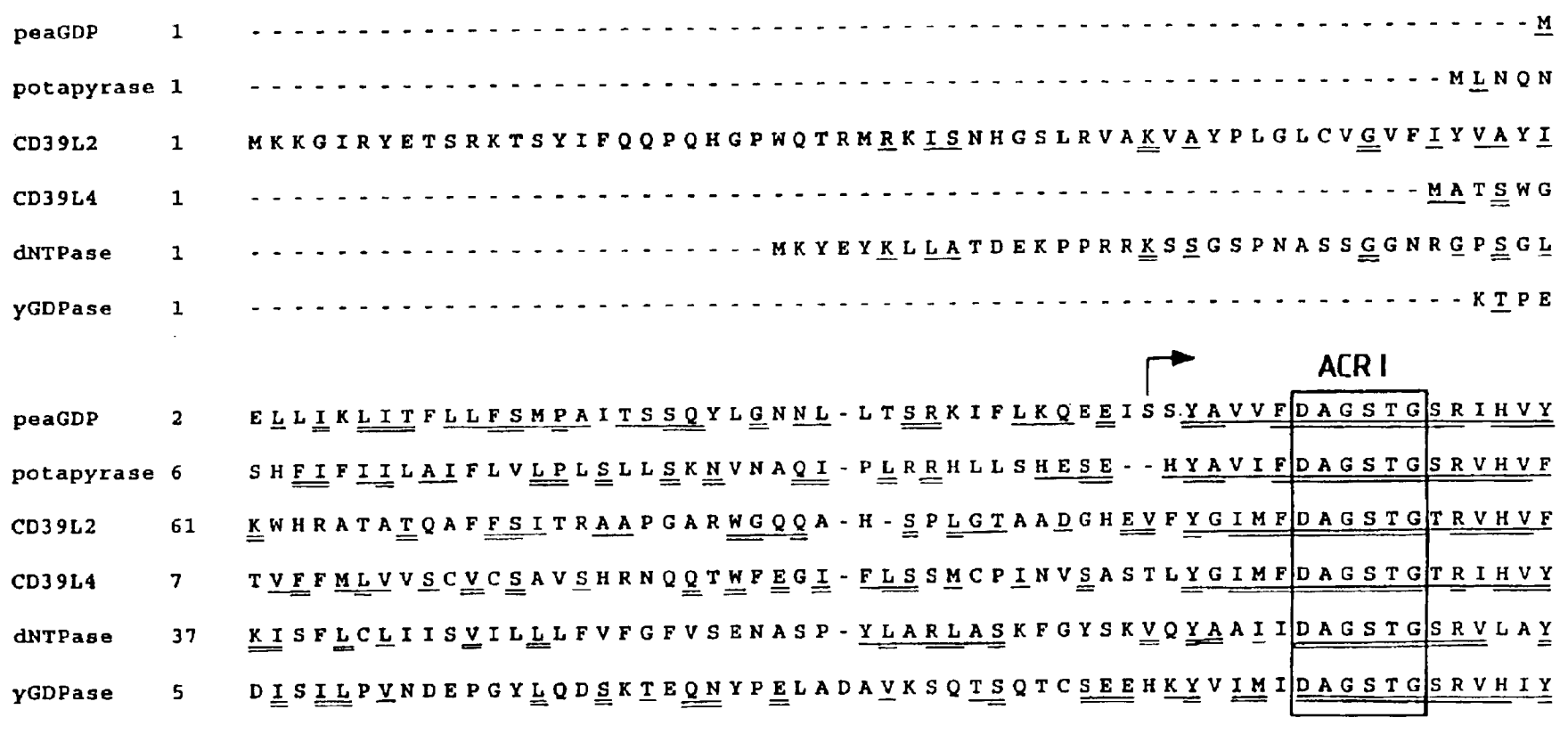

| | | |
|---|---|---|
| peaGDP | 1 | -----------------------------------------------------------M |
| potapyrase | 1 | -------------------------------------------------------MLNQN |
| CD39L2 | 1 | MKKGIRYETSRKTSYIFQQPQHGPWQTRMRKISNHGSLRVAKVAYPLGLCVGVFIYVAYI |
| CD39L4 | 1 | ------------------------------------------------------MATSWG |
| dNTPase | 1 | ------------------------MKYEYKLLATDEKPPRRKSSGSPNASSGGNRGPSGL |
| yGDPase | 1 | --------------------------------------------------------KTPE |

ACR I

| | | |
|---|---|---|
| peaGDP | 2 | ELLIKLITFLLFSMPAITSSQYLGNNL-LTSRKIFLKQEEISSYAVVFDAGSTGSRIHVY |
| potapyrase | 6 | SHFIFIILAIFLVLPLSLLSKNVNAQI-PLRRHLLSHESE--HYAVIFDAGSTGSRVHVF |
| CD39L2 | 61 | KWHRATATQAFFSITRAAPGARWGQQA-H-SPLGTAADGHEVFYGIMFDAGSTGTRVHVF |
| CD39L4 | 7 | TVFFMLVVSCVCSAVSHRNQQTWFEGI-FLSSMCPINVSASTLYGIMFDAGSTGTRIHVY |
| dNTPase | 37 | KISFLCLIISVILLLFVFGFVSENASP-YLARLASKFGYSKVQYAAIIDAGSTGSRVLAY |
| yGDPase | 5 | DISILPVNDEPGYLQDSKTEQNYPELADAVKSQTSQTCSEEHKYVIMIDAGSTGSRVHIY |

FIG. 9A

```
                    ACR IV
peaGDP      180  LGNLGKKYTK--TVGVIDLGGGSVQMAYAVSKKTAKNAPKVADGDDPYIKKVVLKGIPYD
potapyrase  182  LGNLGKDYKS--TTATIDLGGGSVQMAYAISNEQFAKAPQNEDG-EPYVQQKHLMSKDYN
CD39L2      236  TGSLKTPGGS--SVGMLDLGGGSTQIAFLPRVEG-----TLQASPPGYLTALRMFNRIYK
CD39L4      184  TGQLHGHRQE--TVGTLDLGGASTQITFLPQFEK------TLEQTPRGYLTSFEMFNSTYK
dNTPase     214  LGRLSKTNQA--AA----LDLGGGSTQVTFSPTDPD-----QVPVYDK-YMHEVVTSSKKIN
yGDPase     183  LGNIGANGPKLPTAAVFDLGGGSTQIVFEPTFPINEKMV-----DGEHKFDLKFGDENYT

peaGDP      238  LYVHSYLHFGREASRAEILKLTPRSP--------------------NPCLLAGFNG----IY
potapyrase  239  LYVHSYLNYGQLAGRAEIFKASRNES--------------------NPCALEGCDG----YY
CD39L2      289  LYSYSYLGLGLMSARLAILGGVEGQPAKDGKELV------------SPCLSPSFKG----E-W
CD39L4      237  LYTHSYLGFGLKAARLATLGALETE-GTDGHTFR------------SACLPRWLEA----E-W
dNTPase     264  VFTHSYLGLGLMAARHAVF-----THGYKKEDTVLE----------SVCVNPIIAN----RTW
yGDPase     238  LYQFSHLGYGLKEGRNKVNSVLVENALKDGKILKGDNTKTHQLSSPCLPPKVNATNEKVT
```

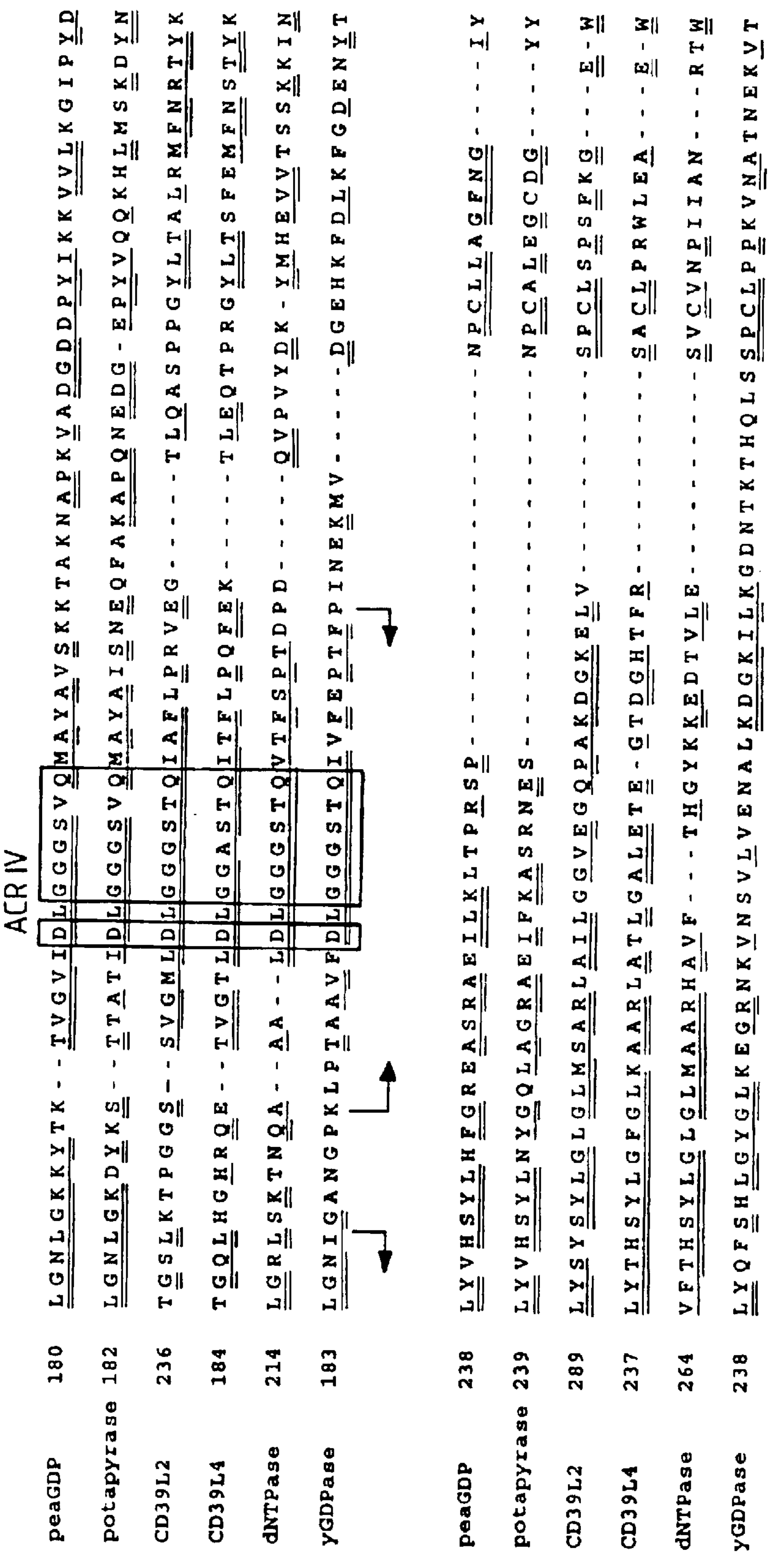

FIG. 9C

| | | |
|---|---|---|
| peaGDP | 276 | T Y S G E E F K A T A Y T S G - A N F N K C K N T I R K A L K L N Y P C P Y Q N C T F G G I W N G G - - - G G N G Q K N |
| potapyrase | 277 | S Y G G V D Y K V K A P K K G - S S W K R C R R L T R H A L K I N A K C N I E E C T F N G V W N G G - - - G G D G Q K N |
| CD39L2 | 335 | E H A E V T Y R V S G Q K A A A S L H E L C A A R - - - V S E V - - - - - L Q N R V - - - - - H R T - - - E E V K H V D |
| CD39L4 | 282 | I F G G V K Y Q Y G G N Q E G E V G F E P C Y A E - - - V L R V - - - - - V R G K L - - - - - H Q P - - - E E V Q R G S |
| dNTPase | 308 | T Y G N V Q Y K V S G K E N G K S S A E Q P I V D F D A C L E L - - - - - V K S K V M P L V K P K P - - - F T L K Q H A |
| yGDPase | 298 | L E S K E T Y T I D F I G P D E P S G A Q C R F L T D E I L N K D A Q C Q S P P C S F N G V H Q P S L V R T F K E S N D |
| peaGDP | 332 | L F A S S S F F Y L P E D T G M V D A S T P N F I L R P V D I E T K A K E A C A L N F E D A K S T Y P F L D K K N V A S |
| potapyrase | 333 | I H A S S F F Y D I G A Q V G I V D T K F P S A L A K P I Q Y L N A A K V A C Q T N V A D I K S I F P K T Q D R N I - P |
| CD39L2 | 379 | F Y A F S Y Y Y D L A A G V G L I D A E - K G G S L V V G D F E I A A K Y V C R T - - - - - - - - - - L E T Q P Q S S P |
| CD39L4 | 326 | F Y A F S Y Y Y D R A V D T D M I D Y E - K G G I L K V E D F E R K A R E V C D N - - - - - - - - - - L E N P T S G S P |
| dNTPase | 360 | V A A F S Y Y F E R A I E S G L V D P L - A G G E T T V E A Y R K K A Q E I C A I - - - - - - - - - - P N D E - - - Q P |
| yGDPase | 358 | I Y I F S Y F Y D R T R P L G M P L S F T L N E L N D L A R I V C K G E E T W N S V F S G I A G S L - - - D E L E S D S |

FIG. 9D

| | | |
|---|---|---|
| peaGDP | 392 | Y V C M D L I Y Q Y V L L V D G F G L D P L Q K I T S G K E I E Y Q D A I V E A A W P L G N A V E A I S A L P K F E R L |
| potapyrase | 392 | Y L C M D L I Y E Y T L L V D G F G L N P H K E I T V I H D V Q Y K N Y L V G A A W P L G C A I D L V S S T T N K I R V |
| CD39L2 | 428 | F S C M D L T Y V S L L L Q E - F G F P R S K V L K L T R K I D N - - - - V E T S W A L G A I F H Y I D S L N R Q K S P |
| CD39L4 | 375 | F L C M D L S Y I T A L L K D G F G F A D S T V L Q L T K K V N N - - - - I E T G W A L G A T F H L L Q S L G I S H |
| dNTPase | 406 | F M C F D L T F I S T L L R E G F G L N D G K K I K L Y K K I D G - - - - H E I S W A L G C A Y N V L T S D E K F S N S |
| yGDPase | 415 | H F C L D L S F Q V S L L H T G Y D I P L Q R E L R T G K K I A N K - - - - E I G W C L G A S L P L L K A D N W K C K I |

| | | |
|---|---|---|
| peaGDP | 452 | M Y F V |
| potapyrase | 452 | A S S * |
| CD39L2 | 483 | A S * |
| CD39L4 | 429 | |
| dNTPase | 462 | |
| yGDPase | 471 | Q S A |

FIG. 9E

SEQUENCE LISTING

```
<160> NUMBER OF SEQ ID NOS: 32

<210> SEQ ID NO 1
<211> LENGTH: 2762
<212> TYPE: DNA
<213> ORGANISM: Homo Sapiens
<220> FEATURE:
```

-continued

```
<221> NAME/KEY: CDS
<222> LOCATION: (232)..(1599)
<223> OTHER INFORMATION:

<400> SEQUENCE: 1

gtggggtcgt atcccgcggg tggaggccgg ggtggcgccg gccggggcgg gggagcccaa      60

aagaccggct gccgcctgct ccccggaaaa gggcactcgt ctccgtgggt gtggcggagc     120

gcgcggtgca tggaatgggc tatgtgaatg aaaaaaggta tccgttatga aacttccaga     180

aaaacgagct acatttttca gcagccgcag cacggtcctt ggcaaacaag g atg aga      237
                                                         Met Arg
                                                         1
aaa ata tcc aac cac ggg agc ctg cgg gtg gcg aag gtg gca tac ccc       285
Lys Ile Ser Asn His Gly Ser Leu Arg Val Ala Lys Val Ala Tyr Pro
        5                   10                  15

ctg ggg ctg tgt gtg ggc gtg ttc atc tat gtt gcc tac atc aag tgg       333
Leu Gly Leu Cys Val Gly Val Phe Ile Tyr Val Ala Tyr Ile Lys Trp
    20                  25                  30

cac cgg gcc acc gcc acc cag gcc ttc ttc agc atc acc agg gca gcc       381
His Arg Ala Thr Ala Thr Gln Ala Phe Phe Ser Ile Thr Arg Ala Ala
35                  40                  45                  50

ccg ggg gcc cgg tgg ggt cag cag gcc cac agc ccc ctg ggg aca gct       429
Pro Gly Ala Arg Trp Gly Gln Gln Ala His Ser Pro Leu Gly Thr Ala
                55                  60                  65

gca gac ggg cac gag gtc ttc tac ggg atc atg ttt gat gca gga agc       477
Ala Asp Gly His Glu Val Phe Tyr Gly Ile Met Phe Asp Ala Gly Ser
            70                  75                  80

act ggc acc cga gta cac gtc ttc cag ttc acc cgg ccc ccc aga gaa       525
Thr Gly Thr Arg Val His Val Phe Gln Phe Thr Arg Pro Pro Arg Glu
        85                  90                  95

act ccc acg tta acc cac gaa acc ttc aaa gca gtg aag cca ggt ctt       573
Thr Pro Thr Leu Thr His Glu Thr Phe Lys Ala Val Lys Pro Gly Leu
    100                 105                 110

tct gcc tat gct gat gat gtt gaa aag agc gct cag gga atc cgg gaa       621
Ser Ala Tyr Ala Asp Asp Val Glu Lys Ser Ala Gln Gly Ile Arg Glu
115                 120                 125                 130

cta ctg gat gtt gct aaa cag gac att ccg ttc gac ttc tgg aag gcc       669
Leu Leu Asp Val Ala Lys Gln Asp Ile Pro Phe Asp Phe Trp Lys Ala
                135                 140                 145

acc cct ctg gtc ctc aag gcc aca gct ggc tta cgc ctg tta cct gga       717
Thr Pro Leu Val Leu Lys Ala Thr Ala Gly Leu Arg Leu Leu Pro Gly
            150                 155                 160

gaa aag gcc cag aag tta ctg cag aag gtg aaa gaa gta ttt aaa gca       765
Glu Lys Ala Gln Lys Leu Leu Gln Lys Val Lys Glu Val Phe Lys Ala
        165                 170                 175

tcg cct ttc ctt gta ggg gat gac tgt gtt tcc atc atg aac gga aca       813
Ser Pro Phe Leu Val Gly Asp Asp Cys Val Ser Ile Met Asn Gly Thr
    180                 185                 190

gat gaa ggc gtt tcg gcg tgg atc acc atc aac ttc ctg aca ggc agc       861
Asp Glu Gly Val Ser Ala Trp Ile Thr Ile Asn Phe Leu Thr Gly Ser
195                 200                 205                 210

ttg aaa act cca gga ggg agc agc gtg ggc atg ctg gac ttg ggc gga       909
Leu Lys Thr Pro Gly Gly Ser Ser Val Gly Met Leu Asp Leu Gly Gly
                215                 220                 225

gga tcc act cag atc gcc ttc ctg cca cgc gtg gag ggc acc ctg cag       957
Gly Ser Thr Gln Ile Ala Phe Leu Pro Arg Val Glu Gly Thr Leu Gln
            230                 235                 240

gcc tcc cca ccc ggc tac ctg acg gca ctg cgg atg ttt aac agg acc      1005
Ala Ser Pro Pro Gly Tyr Leu Thr Ala Leu Arg Met Phe Asn Arg Thr
        245                 250                 255
```

-continued

```
tac aag ctc tat tcc tac agc tac ctc ggg ctc ggg ctg atg tcg gca      1053
Tyr Lys Leu Tyr Ser Tyr Ser Tyr Leu Gly Leu Gly Leu Met Ser Ala
    260                 265                 270

cgc ctg gcg atc ctg ggc ggc gtg gag ggg cag cct gct aag gat gga      1101
Arg Leu Ala Ile Leu Gly Gly Val Glu Gly Gln Pro Ala Lys Asp Gly
275                 280                 285                 290

aag gag ttg gtc agc cct tgc ttg tct ccc agt ttc aaa gga gag tgg      1149
Lys Glu Leu Val Ser Pro Cys Leu Ser Pro Ser Phe Lys Gly Glu Trp
                295                 300                 305

gaa cac gca gaa gtc acg tac agg gtt tca ggg cag aaa gca gcg gca      1197
Glu His Ala Glu Val Thr Tyr Arg Val Ser Gly Gln Lys Ala Ala Ala
            310                 315                 320

agc ctg cac gag ctg tgt gct gcc aga gtg tca gag gtc ctt caa aac      1245
Ser Leu His Glu Leu Cys Ala Ala Arg Val Ser Glu Val Leu Gln Asn
        325                 330                 335

aga gtg cac agg acg gag gaa gtg aag cat gtg gac ttc tat gct ttc      1293
Arg Val His Arg Thr Glu Glu Val Lys His Val Asp Phe Tyr Ala Phe
    340                 345                 350

tcc tac tat tac gac ctt gca gct ggt gtg ggc ctc ata gat gcg gag      1341
Ser Tyr Tyr Tyr Asp Leu Ala Ala Gly Val Gly Leu Ile Asp Ala Glu
355                 360                 365                 370

aag gga ggc agc ctg gtg gtg ggg gac ttc gag atc gca gcc aag tac      1389
Lys Gly Gly Ser Leu Val Val Gly Asp Phe Glu Ile Ala Ala Lys Tyr
                375                 380                 385

gtg tgt cgg acc ctg gag aca cag ccg cag agc agc ccc ttc tca tgc      1437
Val Cys Arg Thr Leu Glu Thr Gln Pro Gln Ser Ser Pro Phe Ser Cys
            390                 395                 400

atg gac ctc acc tac gtc agc ctg cta ctc cag gag ttc ggc ttt ccc      1485
Met Asp Leu Thr Tyr Val Ser Leu Leu Leu Gln Glu Phe Gly Phe Pro
        405                 410                 415

agg agc aaa gtg ctg aag ctc act cgg aaa att gac aat gtt gag acc      1533
Arg Ser Lys Val Leu Lys Leu Thr Arg Lys Ile Asp Asn Val Glu Thr
    420                 425                 430

agc tgg gct ctg ggg gcc att ttt cat tac atc gac tcc ctg aac aga      1581
Ser Trp Ala Leu Gly Ala Ile Phe His Tyr Ile Asp Ser Leu Asn Arg
435                 440                 445                 450

cag aag agt cca gcc tca tagtggccga gccatccctg tccccgtcag             1629
Gln Lys Ser Pro Ala Ser
                455

cagtgtctgt gtgtctgcat aaaccctcct gtcctggacg tgacttcatc ctgaggagcc    1689

acagcacagg ccgtgctggc actttctgca cactggctct gggacttgca gaaggcctgg    1749

tgctgccctg gcatcagcct cttccagtca catctggcca gagggctgtc tggacctggg    1809

ccctgctcaa tgccacctgt ctgcctgggc tccaagtggg caggaccagg acagaaccac    1869

aggcacacac tgagggggca gtgtggctcc ctgcctgtcc catccccatg ccccgtccgc    1929

ggggctgtgg ctgctgctgt gcatgtccct gcgatgggag tcttgtctcc cagcctgtca    1989

gtttcctccc cagggcagag ctccccttcc tgcaagagtc tgggaggcgg tgcaggctgt    2049

cctggctgct ctggggaagc cgagggacag ccataacacc cccgggacag taggtctggg    2109

cggcaccact gggaactctg gacttgagtg tgtttgctct tccttgggta tgaatgtgtg    2169

agttcaccca gaggcctgct ctcctcacac attgtgtggt ttggggttaa tgatggaggg    2229

agacacctct tcatagacgg caggtgccca cctttcaggg agtctcccag catgggcgga    2289

tgccgggcat gagctgctgt aaactatttg tggctgtgct gcttgagtga cgtctctgtc    2349

gtgtgggtgc caagtgcttg tgtagaaact gtgttctgag ccccctttc tggacaccaa     2409

ctgtgtcctg tgaatgtatc gctactgtga gctgttcccg cctagccagg gccatgtctt    2469
```

-continued

```
aggtgcagct gtgccacggg tcagctgagc cacagtccca gaaccaagct ctcggtgtct   2529

cgggccacca tccgcccacc tcgggctgac cccacctcct ccatggacag tgtgagcccc   2589

gggccgtgca tcctgctcag tgtggcgtca gtgtcggggc tgagcccctt gagctgcttc   2649

agtgaatgta cagtgcccgg cacgagctga acctcatgtg ttccactccc aataaaaggt   2709

tgacaggggc ttctccttca aaaaaaaaaa aaaaaaaaaa aaaaaaaaaa aaa          2762


<210> SEQ ID NO 2
<211> LENGTH: 456
<212> TYPE: PRT
<213> ORGANISM: Homo Sapiens

<400> SEQUENCE: 2

Met Arg Lys Ile Ser Asn His Gly Ser Leu Arg Val Ala Lys Val Ala
1               5                   10                  15

Tyr Pro Leu Gly Leu Cys Val Gly Val Phe Ile Tyr Val Ala Tyr Ile
            20                  25                  30

Lys Trp His Arg Ala Thr Ala Thr Gln Ala Phe Phe Ser Ile Thr Arg
        35                  40                  45

Ala Ala Pro Gly Ala Arg Trp Gly Gln Gln Ala His Ser Pro Leu Gly
    50                  55                  60

Thr Ala Ala Asp Gly His Glu Val Phe Tyr Gly Ile Met Phe Asp Ala
65                  70                  75                  80

Gly Ser Thr Gly Thr Arg Val His Val Phe Gln Phe Thr Arg Pro Pro
                85                  90                  95

Arg Glu Thr Pro Thr Leu Thr His Glu Thr Phe Lys Ala Val Lys Pro
            100                 105                 110

Gly Leu Ser Ala Tyr Ala Asp Asp Val Glu Lys Ser Ala Gln Gly Ile
        115                 120                 125

Arg Glu Leu Leu Asp Val Ala Lys Gln Asp Ile Pro Phe Asp Phe Trp
    130                 135                 140

Lys Ala Thr Pro Leu Val Leu Lys Ala Thr Ala Gly Leu Arg Leu Leu
145                 150                 155                 160

Pro Gly Glu Lys Ala Gln Lys Leu Leu Gln Lys Val Lys Glu Val Phe
                165                 170                 175

Lys Ala Ser Pro Phe Leu Val Gly Asp Asp Cys Val Ser Ile Met Asn
            180                 185                 190

Gly Thr Asp Glu Gly Val Ser Ala Trp Ile Thr Ile Asn Phe Leu Thr
        195                 200                 205

Gly Ser Leu Lys Thr Pro Gly Gly Ser Ser Val Gly Met Leu Asp Leu
    210                 215                 220

Gly Gly Gly Ser Thr Gln Ile Ala Phe Leu Pro Arg Val Glu Gly Thr
225                 230                 235                 240

Leu Gln Ala Ser Pro Pro Gly Tyr Leu Thr Ala Leu Arg Met Phe Asn
                245                 250                 255

Arg Thr Tyr Lys Leu Tyr Ser Tyr Ser Tyr Leu Gly Leu Gly Leu Met
            260                 265                 270

Ser Ala Arg Leu Ala Ile Leu Gly Gly Val Glu Gly Gln Pro Ala Lys
        275                 280                 285

Asp Gly Lys Glu Leu Val Ser Pro Cys Leu Ser Pro Ser Phe Lys Gly
    290                 295                 300

Glu Trp Glu His Ala Glu Val Thr Tyr Arg Val Ser Gly Gln Lys Ala
305                 310                 315                 320
```

-continued

Ala Ala Ser Leu His Glu Leu Cys Ala Ala Arg Val Ser Glu Val Leu
325 330 335

Gln Asn Arg Val His Arg Thr Glu Glu Val Lys His Val Asp Phe Tyr
340 345 350

Ala Phe Ser Tyr Tyr Tyr Asp Leu Ala Ala Gly Val Gly Leu Ile Asp
355 360 365

Ala Glu Lys Gly Gly Ser Leu Val Val Gly Asp Phe Glu Ile Ala Ala
370 375 380

Lys Tyr Val Cys Arg Thr Leu Glu Thr Gln Pro Gln Ser Ser Pro Phe
385 390 395 400

Ser Cys Met Asp Leu Thr Tyr Val Ser Leu Leu Leu Gln Glu Phe Gly
405 410 415

Phe Pro Arg Ser Lys Val Leu Lys Leu Thr Arg Lys Ile Asp Asn Val
420 425 430

Glu Thr Ser Trp Ala Leu Gly Ala Ile Phe His Tyr Ile Asp Ser Leu
435 440 445

Asn Arg Gln Lys Ser Pro Ala Ser
450 455

<210> SEQ ID NO 3
<211> LENGTH: 2797
<212> TYPE: DNA
<213> ORGANISM: Homo Sapiens
<220> FEATURE:
<221> NAME/KEY: CDS
<222> LOCATION: (83)..(1669)
<223> OTHER INFORMATION:

<400> SEQUENCE: 3
acccacgcgt ctggccgcgg gccgcctctg cggcagcgct agtcgccttc tccgaatcgg 60
ctccgcacag ctaggagaaa ag atg ttc act gtg ctg acc cgc caa cca tgt 112
Met Phe Thr Val Leu Thr Arg Gln Pro Cys
1 5 10 gag caa gca ggc ctc aag gcc ctc tac cga act cca acc atc att gcc 160
Glu Gln Ala Gly Leu Lys Ala Leu Tyr Arg Thr Pro Thr Ile Ile Ala
15 20 25 ttg gtg gtc ttg ctt gtg agt att gtg gta ctt gtg agt atc act gtc 208
Leu Val Val Leu Leu Val Ser Ile Val Val Leu Val Ser Ile Thr Val
30 35 40 atc cag atc cac aag caa gag gtc ctc cct cca gga ctg aag tat ggt 256
Ile Gln Ile His Lys Gln Glu Val Leu Pro Pro Gly Leu Lys Tyr Gly
45 50 55 att gtg ctg gat gcc ggg tct tca aga acc aca gtc tac gtg tat caa 304
Ile Val Leu Asp Ala Gly Ser Ser Arg Thr Thr Val Tyr Val Tyr Gln
60 65 70 tgg cca gca gaa aaa gag aat aat acc gga gtg gtc agt caa acc ttc 352
Trp Pro Ala Glu Lys Glu Asn Asn Thr Gly Val Val Ser Gln Thr Phe
75 80 85 90 aaa tgt agt gtg aaa ggc tct gga atc tcc agc tat gga aat aac ccc 400
Lys Cys Ser Val Lys Gly Ser Gly Ile Ser Ser Tyr Gly Asn Asn Pro
95 100 105 caa gat gtc ccc aga gcc ttt gag gag tgt atg caa aaa gtc aag ggg 448
Gln Asp Val Pro Arg Ala Phe Glu Glu Cys Met Gln Lys Val Lys Gly
110 115 120 cag gtt cca tcc cac ctc cac gga tcc acc ccc att cac ctg gga gcc 496
Gln Val Pro Ser His Leu His Gly Ser Thr Pro Ile His Leu Gly Ala
125 130 135 acg gct ggg atg cgc ttg ctg agg ttg caa aat gaa aca gca gct aat 544
Thr Ala Gly Met Arg Leu Leu Arg Leu Gln Asn Glu Thr Ala Ala Asn -continued

```
    140                 145                 150

gaa gtc ctt gaa agc atc caa agc tac ttc aag tcc cag ccc ttt gac      592
Glu Val Leu Glu Ser Ile Gln Ser Tyr Phe Lys Ser Gln Pro Phe Asp
155                 160                 165                 170

ttt agg ggt gct caa atc att tct ggg caa gaa gaa ggg gta tat gga      640
Phe Arg Gly Ala Gln Ile Ile Ser Gly Gln Glu Glu Gly Val Tyr Gly
                175                 180                 185

tgg att aca gcc aac tat tta atg gga aat ttc ctg gag aag aac ctg      688
Trp Ile Thr Ala Asn Tyr Leu Met Gly Asn Phe Leu Glu Lys Asn Leu
            190                 195                 200

tgg cac atg tgg gtg cac ccg cat gga gtg gaa acc acg ggt gcc ctg      736
Trp His Met Trp Val His Pro His Gly Val Glu Thr Thr Gly Ala Leu
        205                 210                 215

gac tta ggt ggt gcc tcc acc caa ata tcc ttc gtg gca gga gag aag      784
Asp Leu Gly Gly Ala Ser Thr Gln Ile Ser Phe Val Ala Gly Glu Lys
    220                 225                 230

atg gat ctg aac acc agc gac atc atg cag gtg tcc ctg tat ggc tac      832
Met Asp Leu Asn Thr Ser Asp Ile Met Gln Val Ser Leu Tyr Gly Tyr
235                 240                 245                 250

gta tac acg ctc tac aca cac agc ttc cag tgc tat ggc cgg aat gag      880
Val Tyr Thr Leu Tyr Thr His Ser Phe Gln Cys Tyr Gly Arg Asn Glu
                255                 260                 265

gct gag aag aag ttt ctg gca atg ctc ctg cag aat tct cct acc aaa      928
Ala Glu Lys Lys Phe Leu Ala Met Leu Leu Gln Asn Ser Pro Thr Lys
            270                 275                 280

aac cat ctc acc aat ccc tgt tac cct cgg gat tat agc atc agc ttc      976
Asn His Leu Thr Asn Pro Cys Tyr Pro Arg Asp Tyr Ser Ile Ser Phe
        285                 290                 295

acc atg ggc cat gta ttt gat agc ctg tgc act gtg gac cag agg cca     1024
Thr Met Gly His Val Phe Asp Ser Leu Cys Thr Val Asp Gln Arg Pro
    300                 305                 310

gaa agt tat aac ccc aat gat gtc atc act ttt gaa gga act ggg gac     1072
Glu Ser Tyr Asn Pro Asn Asp Val Ile Thr Phe Glu Gly Thr Gly Asp
315                 320                 325                 330

cca tct ctg tgt aag gag aag gtg gct tcc ata ttt gac ttc aaa gct     1120
Pro Ser Leu Cys Lys Glu Lys Val Ala Ser Ile Phe Asp Phe Lys Ala
                335                 340                 345

tgc cat gat caa gaa acc tgt tct ttt gat ggg gtt tat cag cca aag     1168
Cys His Asp Gln Glu Thr Cys Ser Phe Asp Gly Val Tyr Gln Pro Lys
            350                 355                 360

att aaa ggg cca ttt gtg gct ttt gca gga ttc tac tac aca gcc agt     1216
Ile Lys Gly Pro Phe Val Ala Phe Ala Gly Phe Tyr Tyr Thr Ala Ser
        365                 370                 375

gct tta aat ctt tca ggt agc ttt tcc ctg gac acc ttc aac tcc agc     1264
Ala Leu Asn Leu Ser Gly Ser Phe Ser Leu Asp Thr Phe Asn Ser Ser
    380                 385                 390

acc tgg aat ttc tgc tca cag aat tgg agt cag ctc cca ctg ctg ctc     1312
Thr Trp Asn Phe Cys Ser Gln Asn Trp Ser Gln Leu Pro Leu Leu Leu
395                 400                 405                 410

ccc aaa ttt gat gag gta tat gcc cgc tct tac tgc ttc tca gcc aac     1360
Pro Lys Phe Asp Glu Val Tyr Ala Arg Ser Tyr Cys Phe Ser Ala Asn
                415                 420                 425

tac atc tac cac ttg ttt gtg aac ggt tac aaa ttc aca gag gag act     1408
Tyr Ile Tyr His Leu Phe Val Asn Gly Tyr Lys Phe Thr Glu Glu Thr
            430                 435                 440

tgg ccc caa ata cac ttt gaa aaa gaa gtg ggg aat agc agc ata gcc     1456
Trp Pro Gln Ile His Phe Glu Lys Glu Val Gly Asn Ser Ser Ile Ala
        445                 450                 455

tgg tct ctt ggc tac atg ctc agc ctg acc aac cag atc cca gct gaa     1504
```

-continued

```
Trp Ser Leu Gly Tyr Met Leu Ser Leu Thr Asn Gln Ile Pro Ala Glu
    460                 465                 470

agc cct ctg atc cgt ctg ccc ata gaa cca cct gtc ttt gtg ggc acc      1552
Ser Pro Leu Ile Arg Leu Pro Ile Glu Pro Pro Val Phe Val Gly Thr
475                 480                 485                 490

ctc gct ttc ttc aca gtg gca gcc ttg ctg tgt ctg gca ttt ctt gca      1600
Leu Ala Phe Phe Thr Val Ala Ala Leu Leu Cys Leu Ala Phe Leu Ala
                495                 500                 505

tac ctg tgt tca gca acc aga aga aag agg cac tcc gag cat gcc ttt      1648
Tyr Leu Cys Ser Ala Thr Arg Arg Lys Arg His Ser Glu His Ala Phe
            510                 515                 520

gac cat gca gtg gat tct gac tgagccttca aagcagctcc tggagtccaa        1699
Asp His Ala Val Asp Ser Asp
        525

tggctgctta gagtcagcct gggtggcacc aggcaatgca ggtgaagtgg ctgccttcag   1759

gaaatacaac taactaaaat caaacaccta ggtcacgtgc ctctcaaata ctgatttctg   1819

ccacagcacc tcttgaggca tcccttggct attctgtgca tattgttctt cagagacctc   1879

actacccaca tgctgatcta ttggggaaca gagaagagac aggccactaa ggtcaggctc   1939

tttatattaa gttccccaga ggaagagtaa gttgagaagg tatcagttta atgttgaaga   1999

attgacctca gggctcagtt tccatttccc tccctcagta ttcttcctgg caagataccc   2059

attaagcatt tcgccaatca gaatctcatt ttatagtttt tcccattggt ctttaactaa   2119

gactttcttg tagcaatctc gtaagcagtg aaccccctca gatcagtaga atatagtatc   2179

tgggggagaa gacttacttc cttcagggca gcagccacag ccaggcttct gtcatacagg   2239

tagatcccga agcacagaga cataaaaaag gtctcccaga aaactataga ccattctcca   2299

agtggaattc ccacttaggg ctctggtcac tagattgcaa cctgtgtgtt tgtcatcatc   2359

ctcatctcac cattgtattg ctatgccctc ccataaaaac acattgatcc ctagcaagat   2419

tattgcattc cagattttac tgcctttgct aggcttttgc ttagcaaagg gctgactttc   2479

cattgttatc atggtgtata tatttttgtc accattccca caagtatact tgatgttgtc   2539

atagaacgaa catcctactc tatgatttac taaccaatta ctttcccaga tcatagacct   2599

ctctgcatag tagtcatagg tcttgacttt ggggaaagaa aaggaagctg caggaatatt   2659

tatctccaaa gtcgaatgag aaagaactcc agcaaatcca atggctacaa actaaaaatc   2719

agcattattt catattgctg tttcttagct gaatatggaa taaagaacta ttattttatt   2779

ttgaaaaaaa aaaaaaaa                                                 2797


<210> SEQ ID NO 4
<211> LENGTH: 529
<212> TYPE: PRT
<213> ORGANISM: Homo Sapiens

<400> SEQUENCE: 4

Met Phe Thr Val Leu Thr Arg Gln Pro Cys Glu Gln Ala Gly Leu Lys
1               5                   10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
        35                  40                  45

Glu Val Leu Pro Pro Gly Leu Lys Tyr Gly Ile Val Leu Asp Ala Gly
    50                  55                  60

Ser Ser Arg Thr Thr Val Tyr Val Tyr Gln Trp Pro Ala Glu Lys Glu
65                  70                  75                  80
```

-continued

```
Asn Asn Thr Gly Val Val Ser Gln Thr Phe Lys Cys Ser Val Lys Gly
                85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
            180                 185                 190

Leu Met Gly Asn Phe Leu Glu Lys Asn Leu Trp His Met Trp Val His
        195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
        275                 280                 285

Cys Tyr Pro Arg Asp Tyr Ser Ile Ser Phe Thr Met Gly His Val Phe
    290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
            340                 345                 350

Cys Ser Phe Asp Gly Val Tyr Gln Pro Lys Ile Lys Gly Pro Phe Val
        355                 360                 365

Ala Phe Ala Gly Phe Tyr Tyr Thr Ala Ser Ala Leu Asn Leu Ser Gly
    370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Leu Pro Lys Phe Asp Glu Val
                405                 410                 415

Tyr Ala Arg Ser Tyr Cys Phe Ser Ala Asn Tyr Ile Tyr His Leu Phe
            420                 425                 430

Val Asn Gly Tyr Lys Phe Thr Glu Glu Thr Trp Pro Gln Ile His Phe
        435                 440                 445

Glu Lys Glu Val Gly Asn Ser Ser Ile Ala Trp Ser Leu Gly Tyr Met
    450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Val
                485                 490                 495
```

-continued

```
Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
        515                 520                 525

Asp


<210> SEQ ID NO 5
<211> LENGTH: 1998
<212> TYPE: DNA
<213> ORGANISM: Homo sapiens
<220> FEATURE:
<221> NAME/KEY: CDS
<222> LOCATION: (247)..(1530)
<223> OTHER INFORMATION:

<400> SEQUENCE: 5

gcgcgcgcgt tttccttgtt cctggtcaac aaagaaatgt ggagtgtctt ggctgaatcc     60

tcatacagac aagatcatta tggtgctgtt aggtaggact tgtatccaga tgtaaggttg    120

aaaaagtgat ataataaagg aaccaaggag aaaattcaga aggaaagaaa aaattgcctc    180

tgcaggtgtg cgagcaggat tgcttctgca acaaaagcct ccacccagcc acatcttggg    240

aaaaga atg gcc act tct tgg ggc aca gtc ttt ttc atg ctg gtg gta       288
       Met Ala Thr Ser Trp Gly Thr Val Phe Phe Met Leu Val Val
       1               5                   10

tcc tgt gtt tgc agc gct gtc tcc cac agg aac cag cag act tgg ttt      336
Ser Cys Val Cys Ser Ala Val Ser His Arg Asn Gln Gln Thr Trp Phe
15                  20                  25                  30

gag ggt atc ttc ctg tct tcc atg tgc ccc atc aat gtc agc gcc agc      384
Glu Gly Ile Phe Leu Ser Ser Met Cys Pro Ile Asn Val Ser Ala Ser
                35                  40                  45

acc ttg tat gga att atg ttt gat gca ggg agc act gga act cga att      432
Thr Leu Tyr Gly Ile Met Phe Asp Ala Gly Ser Thr Gly Thr Arg Ile
            50                  55                  60

cat gtt tac acc ttt gtg cag aaa atg cca gga cag ctt cca att cta      480
His Val Tyr Thr Phe Val Gln Lys Met Pro Gly Gln Leu Pro Ile Leu
        65                  70                  75

gaa ggg gaa gtt ttt gat tct gtg aag cca gga ctt tct gct ttt gta      528
Glu Gly Glu Val Phe Asp Ser Val Lys Pro Gly Leu Ser Ala Phe Val
    80                  85                  90

gat caa cct aag cag ggt gct gag acc gtt caa ggg ctc tta gag gtg      576
Asp Gln Pro Lys Gln Gly Ala Glu Thr Val Gln Gly Leu Leu Glu Val
95                  100                 105                 110

gcc aaa gac tca atc ccc cga agt cac tgg aaa aag acc cca gtg gtc      624
Ala Lys Asp Ser Ile Pro Arg Ser His Trp Lys Lys Thr Pro Val Val
                115                 120                 125

cta aag gca aca gca gga cta cgc tta ctg cca gaa cac aaa gcc aag      672
Leu Lys Ala Thr Ala Gly Leu Arg Leu Leu Pro Glu His Lys Ala Lys
            130                 135                 140

gct ctg ctc ttt gag gta aag gag atc ttc agg aag tca cct ttc ctg      720
Ala Leu Leu Phe Glu Val Lys Glu Ile Phe Arg Lys Ser Pro Phe Leu
        145                 150                 155

gta cca aag ggc agt gtt agc atc atg gat gga tcc gac gaa ggc ata      768
Val Pro Lys Gly Ser Val Ser Ile Met Asp Gly Ser Asp Glu Gly Ile
    160                 165                 170

tta gct tgg gtt act gtg aat ttt ctg aca ggt cag ctg cat ggc cac      816
Leu Ala Trp Val Thr Val Asn Phe Leu Thr Gly Gln Leu His Gly His
175                 180                 185                 190

aga cag gag act gtg ggg acc ttg gac cta ggg gga gcc tcc acc caa      864
Arg Gln Glu Thr Val Gly Thr Leu Asp Leu Gly Gly Ala Ser Thr Gln
                195                 200                 205
```

-continued

```
atc acg ttc ctg ccc cag ttt gag aaa act ctg gaa caa act cct agg      912
Ile Thr Phe Leu Pro Gln Phe Glu Lys Thr Leu Glu Gln Thr Pro Arg
            210                 215                 220

ggc tac ctc act tcc ttt gag atg ttt aac agc act tat aag ctc tat      960
Gly Tyr Leu Thr Ser Phe Glu Met Phe Asn Ser Thr Tyr Lys Leu Tyr
        225                 230                 235

aca cat agt tac ttg gga ttt gga ttg aaa gct gca aga cta gca acc     1008
Thr His Ser Tyr Leu Gly Phe Gly Leu Lys Ala Ala Arg Leu Ala Thr
    240                 245                 250

ctg gga gcc ctg gag aca gaa ggg act gat ggg cac act ttc cgg agt     1056
Leu Gly Ala Leu Glu Thr Glu Gly Thr Asp Gly His Thr Phe Arg Ser
255                 260                 265                 270

gcc tgt tta ccg aga tgg ttg gaa gca gag tgg atc ttt ggg ggt gtg     1104
Ala Cys Leu Pro Arg Trp Leu Glu Ala Glu Trp Ile Phe Gly Gly Val
                275                 280                 285

aaa tac cag tat ggt ggc aac caa gaa ggg gag gtg ggc ttt gag ccc     1152
Lys Tyr Gln Tyr Gly Gly Asn Gln Glu Gly Glu Val Gly Phe Glu Pro
            290                 295                 300

tgc tat gcc gaa gtg ctg agg gtg gta cga gga aaa ctt cac cag cca     1200
Cys Tyr Ala Glu Val Leu Arg Val Val Arg Gly Lys Leu His Gln Pro
        305                 310                 315

gag gag gtc cag aga ggt tcc ttc tat gct ttc tct tac tat tat gac     1248
Glu Glu Val Gln Arg Gly Ser Phe Tyr Ala Phe Ser Tyr Tyr Tyr Asp
    320                 325                 330

cga gct gtt gac aca gac atg att gat tat gaa aag ggg ggt att tta     1296
Arg Ala Val Asp Thr Asp Met Ile Asp Tyr Glu Lys Gly Gly Ile Leu
335                 340                 345                 350

aaa gtt gaa gat ttt gaa aga aaa gcc agg gaa gtg tgt gat aac ttg     1344
Lys Val Glu Asp Phe Glu Arg Lys Ala Arg Glu Val Cys Asp Asn Leu
                355                 360                 365

gaa aac ttc acc tca ggc agt cct ttc ctg tgc atg gat ctc agc tac     1392
Glu Asn Phe Thr Ser Gly Ser Pro Phe Leu Cys Met Asp Leu Ser Tyr
            370                 375                 380

atc aca gcc ctg tta aag gat ggc ttt ggc ttt gca gac agc aca gtc     1440
Ile Thr Ala Leu Leu Lys Asp Gly Phe Gly Phe Ala Asp Ser Thr Val
        385                 390                 395

tta cag ctc aca aag aaa gtg aac aac ata gag acg ggc tgg gcc ttg     1488
Leu Gln Leu Thr Lys Lys Val Asn Asn Ile Glu Thr Gly Trp Ala Leu
    400                 405                 410

ggg gcc acc ttt cac ctg ttg cag tct ctg ggc atc tcc cat             1530
Gly Ala Thr Phe His Leu Leu Gln Ser Leu Gly Ile Ser His
415                 420                 425

tgaggccacg tacttccttg gagacctgca tttgccaaca ccttttaag gggaggagag   1590

agcacttagt ttctgaacta gtctgggaca tcctggactt gagcctagag atttaggttt   1650

aattaatttt acacatctaa tgtgaactgc tgcctaacca ctcaagagta cacagctggc   1710

accagagcat cacagagagc cctgtgagcc aaaaagtata gttttggaac ttaaccttgg   1770

agtgagagcc cagggacagg tccctggaaa ccaaagaaaa atcgcatttc aacccttga    1830

gtgcctcatt ccactgaata tttaaatttt cctcttaaat ggtaaactga cttattgcaa   1890

tcccaagacc catcaatatc agtatttttt tcctccctat acagtgccct gcccaccctt   1950

atctgcaccc acctcccctg aaaaagagag aaaaaaaaaa aaaaaaaa                1998
```

<210> SEQ ID NO 6
<211> LENGTH: 428
<212> TYPE: PRT
<213> ORGANISM: Homo sapiens -continued

<400> SEQUENCE: 6

```
Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr Gly Thr Arg Ile His Val
    50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400

Leu Thr Lys Lys Val Asn Asn Ile Glu Thr Gly Trp Ala Leu Gly Ala
                405                 410                 415
```

-continued

```
Thr Phe His Leu Leu Gln Ser Leu Gly Ile Ser His
            420                 425


<210> SEQ ID NO 7
<211> LENGTH: 2119
<212> TYPE: DNA
<213> ORGANISM: Mus musculus
<220> FEATURE:
<221> NAME/KEY: CDS
<222> LOCATION: (205)..(1599)
<223> OTHER INFORMATION:

<400> SEQUENCE: 7

acgttgacac aggaatgaag agtgtattgg ctgaatcttc aagcagaggc gatattgacc      60

atgtgctttt taaattggcc tgcgtgaccc gcccacttgg tgtaaaagaa gaaccggcca     120

aagggagggc ctgaaggacc tccacaggag tgtgagcagc actgcttcag caacaaagcc     180

tcaggtccac atcttgggaa gaat atg gcc act tcc tgg ggg gct gtc ttc       231
                           Met Ala Thr Ser Trp Gly Ala Val Phe
                           1               5

atg ctg atc ata gcc tgc gtt ggc agc act gtc ttc tac aga gaa cag       279
Met Leu Ile Ile Ala Cys Val Gly Ser Thr Val Phe Tyr Arg Glu Gln
10                  15                  20                  25

cag acc tgg ttt gaa ggt gtc ttc ttg tct tcc atg tgc ccc att aat       327
Gln Thr Trp Phe Glu Gly Val Phe Leu Ser Ser Met Cys Pro Ile Asn
                30                  35                  40

gtc agt gcc ggc acc ttt tat gga att atg ttt gat gcg ggc agc act       375
Val Ser Ala Gly Thr Phe Tyr Gly Ile Met Phe Asp Ala Gly Ser Thr
            45                  50                  55

gga gct cgg att cat gtt tac act ttt gtg cag aaa aca gca gga cag       423
Gly Ala Arg Ile His Val Tyr Thr Phe Val Gln Lys Thr Ala Gly Gln
        60                  65                  70

ctc ccc ttt ctg gaa ggt gaa att ttt gat tct gtg aag ccg gga ctt       471
Leu Pro Phe Leu Glu Gly Glu Ile Phe Asp Ser Val Lys Pro Gly Leu
    75                  80                  85

tct gct ttt gtg gat cag ccc aaa cag ggt gct gag act gtc cag gag       519
Ser Ala Phe Val Asp Gln Pro Lys Gln Gly Ala Glu Thr Val Gln Glu
90                  95                  100                 105

ctc ttg gag gtg gcc aaa gac tcg atc ccc aga agc cac tgg gaa agg       567
Leu Leu Glu Val Ala Lys Asp Ser Ile Pro Arg Ser His Trp Glu Arg
                110                 115                 120

acc ccg gtg gtt ctg aaa gca acg gcc gga ctc cgt ttg ctg cct gag       615
Thr Pro Val Val Leu Lys Ala Thr Ala Gly Leu Arg Leu Leu Pro Glu
            125                 130                 135

cag aaa gcc cag gct ctg ctc ttg gag gta gag gag atc ttc aag aat       663
Gln Lys Ala Gln Ala Leu Leu Leu Glu Val Glu Glu Ile Phe Lys Asn
        140                 145                 150

tca cct ttc ctg gtc cca gat ggc agc gtt agc atc atg gat ggg tcc       711
Ser Pro Phe Leu Val Pro Asp Gly Ser Val Ser Ile Met Asp Gly Ser
    155                 160                 165

tat gaa ggc ata cta gcc tgg gtt acc gtg aac ttt cta aca ggt cag       759
Tyr Glu Gly Ile Leu Ala Trp Val Thr Val Asn Phe Leu Thr Gly Gln
170                 175                 180                 185

ctg cat ggt cgt ggc cag gag act gtg ggg acc ctt gac ctg ggg ggt       807
Leu His Gly Arg Gly Gln Glu Thr Val Gly Thr Leu Asp Leu Gly Gly
                190                 195                 200

gcc tcc acc caa atc acg ttt cta ccc cag ttt gag aaa acc ctg gaa       855
Ala Ser Thr Gln Ile Thr Phe Leu Pro Gln Phe Glu Lys Thr Leu Glu
            205                 210                 215

caa aca cct agg ggc tac ctc act tcc ttt gag atg ttt aac agc act       903
```

-continued

```
Gln Thr Pro Arg Gly Tyr Leu Thr Ser Phe Glu Met Phe Asn Ser Thr
        220                 225                 230

ttt aag ctc tat aca cat agt tac ttg gga ttt gga ctg aaa gct gca      951
Phe Lys Leu Tyr Thr His Ser Tyr Leu Gly Phe Gly Leu Lys Ala Ala
    235                 240                 245

aga ctg gca act ctg gga gcc ctg gaa gca aaa ggg act gat gga cat      999
Arg Leu Ala Thr Leu Gly Ala Leu Glu Ala Lys Gly Thr Asp Gly His
250                 255                 260                 265

acg ttt cga agt gcc tgt tta cca aga tgg ttg gaa gca gag tgg atc     1047
Thr Phe Arg Ser Ala Cys Leu Pro Arg Trp Leu Glu Ala Glu Trp Ile
                270                 275                 280

ttt ggg ggt gtg aaa tac cag tat ggt ggt aac caa gaa ggg gag atg     1095
Phe Gly Gly Val Lys Tyr Gln Tyr Gly Gly Asn Gln Glu Gly Glu Met
            285                 290                 295

ggc ttt gaa ccc tgc tat gcg gaa gtg ctg agg gta gta cag ggg aaa     1143
Gly Phe Glu Pro Cys Tyr Ala Glu Val Leu Arg Val Val Gln Gly Lys
        300                 305                 310

ctt cac cag cca gaa gaa gtc cga gga agc gcc ttc tac gct ttc tct     1191
Leu His Gln Pro Glu Glu Val Arg Gly Ser Ala Phe Tyr Ala Phe Ser
    315                 320                 325

tac tac tac gat cga gcc gct gac aca cac ttg atc gat tat gaa aag     1239
Tyr Tyr Tyr Asp Arg Ala Ala Asp Thr His Leu Ile Asp Tyr Glu Lys
330                 335                 340                 345

ggc ggg gtt tta aaa gtt gaa gat ttt gaa aga aaa gcc aga gaa gtg     1287
Gly Gly Val Leu Lys Val Glu Asp Phe Glu Arg Lys Ala Arg Glu Val
                350                 355                 360

tgt gac aac ttg ggg agc ttc tcc tcg ggc agt cct ttc ctc tgc atg     1335
Cys Asp Asn Leu Gly Ser Phe Ser Ser Gly Ser Pro Phe Leu Cys Met
            365                 370                 375

gac ctc act tac atc aca gcc ctg ttg aaa gat ggt ttg ggc ttt gcc     1383
Asp Leu Thr Tyr Ile Thr Ala Leu Leu Lys Asp Gly Leu Gly Phe Ala
        380                 385                 390

gaa cgg cac cct ctt aca gct cac aaa gaa agt gaa caa cat aga gac     1431
Glu Arg His Pro Leu Thr Ala His Lys Glu Ser Glu Gln His Arg Asp
    395                 400                 405

tgg ttg ggc ctt ggg ggc cac ctt tca cct gct cca gtc tct ggg cat     1479
Trp Leu Gly Leu Gly Gly His Leu Ser Pro Ala Pro Val Ser Gly His
410                 415                 420                 425

cac cag ctg agg cca agc tcc acc tct gaa gcc tgc att tct gaa cca     1527
His Gln Leu Arg Pro Ser Ser Thr Ser Glu Ala Cys Ile Ser Glu Pro
                430                 435                 440

gtt ttc tca cag gaa ggc gtg gac tca gag aca ttt tct gac ctc tct     1575
Val Phe Ser Gln Glu Gly Val Asp Ser Glu Thr Phe Ser Asp Leu Ser
            445                 450                 455

gga aaa gcc tgg ccc gaa acc cgt taactggttt tataaggagg gaggggtttt    1629
Gly Lys Ala Trp Pro Glu Thr Arg
        460                 465

tagatgagtc ttgctcttga gcctagtgat ttgggcttca atgatttgca catctaatgt   1689

gaatagctcc taaccacttg gtgggtgcat ggctggcacc agactgtaaa tcttttggga   1749

ttctttgtac agagtcctgc aaaggaaaaa agagaaaagg tttggaactc catgctagat   1809

tgcgagttca gagacaggtc cctggggacc aaagaacaat ctcgtttcaa cccttggatg   1869

cctcattgct ttgaatggat tcatttttgc ttataagctg atttactgaa atcccataac   1929

ccatcaatgc tgttaatttt tttcttccta cccttattac attccctacc ctaaaagcct   1989

gggggaaata cctggttttg cttcccatct ataattgaga aagagggggg aaaagatact   2049

gtattagaat ttgtgtgatc ctgtggcaca atagatcaac caacccattt aaagcttaaa   2109
```

-continued

```
aaaaaaaaaa                                                        2119


<210> SEQ ID NO 8
<211> LENGTH: 465
<212> TYPE: PRT
<213> ORGANISM: Mus musculus

<400> SEQUENCE: 8

Met Ala Thr Ser Trp Gly Ala Val Phe Met Leu Ile Ile Ala Cys Val
1               5                   10                  15

Gly Ser Thr Val Phe Tyr Arg Glu Gln Gln Thr Trp Phe Glu Gly Val
            20                  25                  30

Phe Leu Ser Ser Met Cys Pro Ile Asn Val Ser Ala Gly Thr Phe Tyr
        35                  40                  45

Gly Ile Met Phe Asp Ala Gly Ser Thr Gly Ala Arg Ile His Val Tyr
    50                  55                  60

Thr Phe Val Gln Lys Thr Ala Gly Gln Leu Pro Phe Leu Glu Gly Glu
65                  70                  75                  80

Ile Phe Asp Ser Val Lys Pro Gly Leu Ser Ala Phe Val Asp Gln Pro
                85                  90                  95

Lys Gln Gly Ala Glu Thr Val Gln Glu Leu Leu Glu Val Ala Lys Asp
            100                 105                 110

Ser Ile Pro Arg Ser His Trp Glu Arg Thr Pro Val Val Leu Lys Ala
        115                 120                 125

Thr Ala Gly Leu Arg Leu Leu Pro Glu Gln Lys Ala Gln Ala Leu Leu
    130                 135                 140

Leu Glu Val Glu Glu Ile Phe Lys Asn Ser Pro Phe Leu Val Pro Asp
145                 150                 155                 160

Gly Ser Val Ser Ile Met Asp Gly Ser Tyr Glu Gly Ile Leu Ala Trp
                165                 170                 175

Val Thr Val Asn Phe Leu Thr Gly Gln Leu His Gly Arg Gly Gln Glu
            180                 185                 190

Thr Val Gly Thr Leu Asp Leu Gly Gly Ala Ser Thr Gln Ile Thr Phe
        195                 200                 205

Leu Pro Gln Phe Glu Lys Thr Leu Glu Gln Thr Pro Arg Gly Tyr Leu
    210                 215                 220

Thr Ser Phe Glu Met Phe Asn Ser Thr Phe Lys Leu Tyr Thr His Ser
225                 230                 235                 240

Tyr Leu Gly Phe Gly Leu Lys Ala Ala Arg Leu Ala Thr Leu Gly Ala
                245                 250                 255

Leu Glu Ala Lys Gly Thr Asp Gly His Thr Phe Arg Ser Ala Cys Leu
            260                 265                 270

Pro Arg Trp Leu Glu Ala Glu Trp Ile Phe Gly Gly Val Lys Tyr Gln
        275                 280                 285

Tyr Gly Gly Asn Gln Glu Gly Glu Met Gly Phe Glu Pro Cys Tyr Ala
    290                 295                 300

Glu Val Leu Arg Val Val Gln Gly Lys Leu His Gln Pro Glu Glu Val
305                 310                 315                 320

Arg Gly Ser Ala Phe Tyr Ala Phe Ser Tyr Tyr Tyr Asp Arg Ala Ala
                325                 330                 335

Asp Thr His Leu Ile Asp Tyr Glu Lys Gly Gly Val Leu Lys Val Glu
            340                 345                 350

Asp Phe Glu Arg Lys Ala Arg Glu Val Cys Asp Asn Leu Gly Ser Phe
        355                 360                 365
```

-continued

```
Ser Ser Gly Ser Pro Phe Leu Cys Met Asp Leu Thr Tyr Ile Thr Ala
    370                 375                 380

Leu Leu Lys Asp Gly Leu Gly Phe Ala Glu Arg His Pro Leu Thr Ala
385                 390                 395                 400

His Lys Glu Ser Glu Gln His Arg Asp Trp Leu Gly Leu Gly Gly His
                405                 410                 415

Leu Ser Pro Ala Pro Val Ser Gly His His Gln Leu Arg Pro Ser Ser
            420                 425                 430

Thr Ser Glu Ala Cys Ile Ser Glu Pro Val Phe Ser Gln Glu Gly Val
        435                 440                 445

Asp Ser Glu Thr Phe Ser Asp Leu Ser Gly Lys Ala Trp Pro Glu Thr
    450                 455                 460

Arg
465


<210> SEQ ID NO 9
<211> LENGTH: 428
<212> TYPE: PRT
<213> ORGANISM: Homo sapiens

<400> SEQUENCE: 9

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr Gly Thr Arg Ile His Val
    50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270
```

-continued

```
Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400

Leu Thr Lys Lys Val Asn Asn Ile Glu Thr Gly Trp Ala Leu Gly Ala
                405                 410                 415

Thr Phe His Leu Leu Gln Ser Leu Gly Ile Ser His
            420                 425


<210> SEQ ID NO 10
<211> LENGTH: 455
<212> TYPE: PRT
<213> ORGANISM: P. sativum

<400> SEQUENCE: 10

Met Glu Leu Leu Ile Lys Leu Ile Thr Phe Leu Leu Phe Ser Met Pro
1               5                   10                  15

Ala Ile Thr Ser Ser Gln Tyr Leu Gly Asn Asn Leu Leu Thr Ser Arg
            20                  25                  30

Lys Ile Phe Leu Lys Gln Glu Glu Ile Ser Ser Tyr Ala Val Val Phe
        35                  40                  45

Asp Ala Gly Ser Thr Gly Ser Arg Ile His Val Tyr His Phe Asn Gln
    50                  55                  60

Asn Leu Asp Leu Leu His Ile Gly Lys Gly Val Glu Tyr Tyr Asn Lys
65                  70                  75                  80

Ile Thr Pro Gly Leu Ser Ser Tyr Ala Asn Asn Pro Glu Gln Ala Ala
                85                  90                  95

Lys Ser Leu Ile Pro Leu Leu Glu Gln Ala Glu Asp Val Val Pro Asp
            100                 105                 110

Asp Leu Gln Pro Lys Thr Pro Val Arg Leu Gly Ala Thr Ala Gly Leu
        115                 120                 125

Arg Leu Leu Asn Gly Asp Ala Ser Glu Lys Ile Leu Gln Ser Val Arg
    130                 135                 140

Asp Met Leu Ser Asn Arg Ser Thr Phe Asn Val Gln Pro Asp Ala Val
145                 150                 155                 160

Ser Ile Ile Asp Gly Thr Gln Glu Gly Ser Tyr Leu Trp Val Thr Val
                165                 170                 175

Asn Tyr Ala Leu Gly Asn Leu Gly Lys Lys Tyr Thr Lys Thr Val Gly
            180                 185                 190

Val Ile Asp Leu Gly Gly Gly Ser Val Gln Met Ala Tyr Ala Val Ser
        195                 200                 205

Lys Lys Thr Ala Lys Asn Ala Pro Lys Val Ala Asp Gly Asp Asp Pro
```

-continued

```
    210                 215                 220

Tyr Ile Lys Lys Val Val Leu Lys Gly Ile Pro Tyr Asp Leu Tyr Val
225                 230                 235                 240

His Ser Tyr Leu His Phe Gly Arg Glu Ala Ser Arg Ala Glu Ile Leu
                245                 250                 255

Lys Leu Thr Pro Arg Ser Pro Asn Pro Cys Leu Leu Ala Gly Phe Asn
            260                 265                 270

Gly Ile Tyr Thr Tyr Ser Gly Glu Glu Phe Lys Ala Thr Ala Tyr Thr
        275                 280                 285

Ser Gly Ala Asn Phe Asn Lys Cys Lys Asn Thr Ile Arg Lys Ala Leu
    290                 295                 300

Lys Leu Asn Tyr Pro Cys Pro Tyr Gln Asn Cys Thr Phe Gly Gly Ile
305                 310                 315                 320

Trp Asn Gly Gly Gly Gly Asn Gly Gln Lys Asn Leu Phe Ala Ser Ser
                325                 330                 335

Ser Phe Phe Tyr Leu Pro Glu Asp Thr Gly Met Val Asp Ala Ser Thr
            340                 345                 350

Pro Asn Phe Ile Leu Arg Pro Val Asp Ile Glu Thr Lys Ala Lys Glu
        355                 360                 365

Ala Cys Ala Leu Asn Phe Glu Asp Ala Lys Ser Thr Tyr Pro Phe Leu
    370                 375                 380

Asp Lys Lys Asn Val Ala Ser Tyr Val Cys Met Asp Leu Ile Tyr Gln
385                 390                 395                 400

Tyr Val Leu Leu Val Asp Gly Phe Gly Leu Asp Pro Leu Gln Lys Ile
                405                 410                 415

Thr Ser Gly Lys Glu Ile Glu Tyr Gln Asp Ala Ile Val Glu Ala Ala
            420                 425                 430

Trp Pro Leu Gly Asn Ala Val Glu Ala Ile Ser Ala Leu Pro Lys Phe
        435                 440                 445

Glu Arg Leu Met Tyr Phe Val
    450                 455


<210> SEQ ID NO 11
<211> LENGTH: 454
<212> TYPE: PRT
<213> ORGANISM: Solanum tuberosum

<400> SEQUENCE: 11

Met Leu Asn Gln Asn Ser His Phe Ile Phe Ile Ile Leu Ala Ile Phe
1               5                   10                  15

Leu Val Leu Pro Leu Ser Leu Leu Ser Lys Asn Val Asn Ala Gln Ile
            20                  25                  30

Pro Leu Arg Arg His Leu Leu Ser His Glu Ser Glu His Tyr Ala Val
        35                  40                  45

Ile Phe Asp Ala Gly Ser Thr Gly Ser Arg Val His Val Phe Arg Phe
    50                  55                  60

Asp Glu Lys Leu Gly Leu Leu Pro Ile Gly Asn Asn Ile Glu Tyr Phe
65                  70                  75                  80

Met Ala Thr Glu Pro Gly Leu Ser Ser Tyr Ala Glu Asp Pro Lys Ala
                85                  90                  95

Ala Ala Asn Ser Leu Glu Pro Leu Leu Asp Gly Ala Glu Gly Val Val
            100                 105                 110

Pro Gln Glu Leu Gln Ser Glu Thr Pro Leu Glu Leu Gly Ala Thr Ala
        115                 120                 125
```

-continued

```
Gly Leu Arg Met Leu Lys Gly Asp Ala Ala Glu Lys Ile Leu Gln Ala
    130                 135                 140

Val Arg Asn Leu Val Lys Asn Gln Ser Thr Phe His Ser Lys Asp Gln
145                 150                 155                 160

Trp Val Thr Ile Leu Asp Gly Thr Gln Glu Gly Ser Tyr Met Trp Ala
                165                 170                 175

Ala Ile Asn Tyr Leu Leu Gly Asn Leu Gly Lys Asp Tyr Lys Ser Thr
            180                 185                 190

Thr Ala Thr Ile Asp Leu Gly Gly Gly Ser Val Gln Met Ala Tyr Ala
        195                 200                 205

Ile Ser Asn Glu Gln Phe Ala Lys Ala Pro Gln Asn Glu Asp Gly Glu
    210                 215                 220

Pro Tyr Val Gln Gln Lys His Leu Met Ser Lys Asp Tyr Asn Leu Tyr
225                 230                 235                 240

Val His Ser Tyr Leu Asn Tyr Gly Gln Leu Ala Gly Arg Ala Glu Ile
                245                 250                 255

Phe Lys Ala Ser Arg Asn Glu Ser Asn Pro Cys Ala Leu Glu Gly Cys
            260                 265                 270

Asp Gly Tyr Tyr Ser Tyr Gly Gly Val Asp Tyr Lys Val Lys Ala Pro
        275                 280                 285

Lys Lys Gly Ser Ser Trp Lys Arg Cys Arg Arg Leu Thr Arg His Ala
    290                 295                 300

Leu Lys Ile Asn Ala Lys Cys Asn Ile Glu Glu Cys Thr Phe Asn Gly
305                 310                 315                 320

Val Trp Asn Gly Gly Gly Gly Asp Gly Gln Lys Asn Ile His Ala Ser
                325                 330                 335

Ser Phe Phe Tyr Asp Ile Gly Ala Gln Val Gly Ile Val Asp Thr Lys
            340                 345                 350

Phe Pro Ser Ala Leu Ala Lys Pro Ile Gln Tyr Leu Asn Ala Ala Lys
        355                 360                 365

Val Ala Cys Gln Thr Asn Val Ala Asp Ile Lys Ser Ile Phe Pro Lys
    370                 375                 380

Thr Gln Asp Arg Asn Ile Pro Tyr Leu Cys Met Asp Leu Ile Tyr Glu
385                 390                 395                 400

Tyr Thr Leu Leu Val Asp Gly Phe Gly Leu Asn Pro His Lys Glu Ile
                405                 410                 415

Thr Val Ile His Asp Val Gln Tyr Lys Asn Tyr Leu Val Gly Ala Ala
            420                 425                 430

Trp Pro Leu Gly Cys Ala Ile Asp Leu Val Ser Ser Thr Thr Asn Lys
        435                 440                 445

Ile Arg Val Ala Ser Ser
    450


<210> SEQ ID NO 12
<211> LENGTH: 473
<212> TYPE: PRT
<213> ORGANISM: Saccharomyces cerevisiae

<400> SEQUENCE: 12

Lys Thr Pro Glu Asp Ile Ser Ile Ile Pro Val Asn Asp Glu Pro Gly
1               5                   10                  15

Tyr Leu Gln Asp Ser Lys Thr Glu Gln Asn Tyr Pro Glu Leu Ala Asp
            20                  25                  30

Ala Val Lys Ser Gln Thr Ser Gln Thr Cys Ser Glu Glu His Lys Tyr
        35                  40                  45
```

-continued

```
Val Ile Met Ile Asp Ala Gly Ser Thr Gly Ser Arg Val His Ile Tyr
    50                  55                  60

Lys Phe Asp Val Cys Thr Ser Pro Pro Thr Leu Leu Asp Glu Lys Phe
65                  70                  75                  80

Asp Met Leu Glu Pro Gly Leu Ser Ser Phe Asp Thr Asp Ser Val Gly
                85                  90                  95

Ala Ala Asn Ser Leu Asp Pro Leu Leu Lys Val Ala Met Asn Tyr Val
            100                 105                 110

Pro Ile Lys Ala Arg Ser Cys Thr Pro Val Ala Val Lys Ala Thr Ala
        115                 120                 125

Gly Leu Arg Leu Leu Gly Asp Ala Lys Ser Ser Lys Ile Leu Ser Ala
    130                 135                 140

Val Arg Asp His Leu Glu Lys Asp Tyr Pro Phe Pro Val Val Glu Gly
145                 150                 155                 160

Asp Gly Val Ser Ile Met Gly Gly Asp Glu Glu Gly Val Phe Ala Trp
                165                 170                 175

Ile Thr Thr Asn Tyr Leu Leu Gly Asn Ile Gly Ala Asn Gly Pro Lys
            180                 185                 190

Leu Pro Thr Ala Ala Val Phe Asp Leu Gly Gly Gly Ser Thr Gln Ile
        195                 200                 205

Val Glu Glu Pro Thr Phe Pro Ile Asn Glu Lys Met Val Asp Gly Glu
    210                 215                 220

His Lys Phe Asp Leu Lys Phe Gly Asp Glu Asn Tyr Thr Leu Tyr Gln
225                 230                 235                 240

Phe Ser His Leu Gly Tyr Gly Leu Lys Glu Gly Arg Asn Lys Val Asn
                245                 250                 255

Ser Val Leu Val Glu Asn Ala Leu Lys Asp Lys Ile Leu Lys Gly Cys
            260                 265                 270

Asn Thr Lys Thr His Cys Leu Ser Ser Pro Cys Leu Pro Pro Lys Val
        275                 280                 285

Asn Ala Thr Asn Glu Lys Val Thr Leu Glu Ser Lys Glu Thr Tyr Thr
    290                 295                 300

Ile Asp Phe Ile Gly Pro Asp Glu Pro Ser Gly Ala Gln Cys Arg Phe
305                 310                 315                 320

Leu Thr Asp Glu Ile Leu Asn Lys Asp Ala Gln Cys Gln Ser Pro Pro
                325                 330                 335

Cys Ser Phe Asn Gly Val His Gln Pro Ser Leu Val Arg Thr Phe Lys
            340                 345                 350

Glu Ser Asn Asp Ile Tyr Ile Phe Ser Tyr Phe Tyr Asp Arg Thr Thr
        355                 360                 365

Arg Pro Leu Gly Met Pro Leu Ser Phe Thr Leu Asn Glu Leu Asn Asp
    370                 375                 380

Leu Ala Arg Ile Val Cys Lys Gly Glu Glu Thr Trp Asn Ser Val Phe
385                 390                 395                 400

Ser Gly Ile Ala Gly Ser Leu Asp Glu Leu Glu Ser Asp Ser His Phe
                405                 410                 415

Cys Leu Asp Leu Ser Phe Gln Val Ser Leu Leu His Thr Gly Tyr Asp
            420                 425                 430

Ile Pro Leu Gln Arg Glu Leu Arg Thr Gly Lys Lys Ile Ala Asn Lys
        435                 440                 445

Glu Ile Gly Trp Cys Leu Gly Ala Ser Leu Pro Leu Leu Lys Ala Asp
    450                 455                 460
```

-continued

```
Asn Trp Lys Cys Lys Ile Gln Ser Ala
465                 470


<210> SEQ ID NO 13
<211> LENGTH: 153
<212> TYPE: PRT
<213> ORGANISM: Homo sapiens

<400> SEQUENCE: 13

Lys Tyr Gly Ile Val Leu Asp Ala Gly Ser Ser His Thr Ser Leu Tyr
1               5                   10                  15

Ile Tyr Lys Trp Pro Ala Glu Lys Glu Asn Asp Thr Gly Val Val His
            20                  25                  30

Gln Val Glu Glu Cys Arg Val Lys Gly Pro Gly Ile Ser Lys Phe Val
        35                  40                  45

Gln Lys Val Asn Glu Ile Gly Ile Tyr Leu Thr Asp Cys Met Glu Arg
    50                  55                  60

Ala Arg Glu Val Ile Pro Arg Ser Gln His Gln Glu Thr Pro Val Tyr
65                  70                  75                  80

Leu Gly Ala Thr Ala Gly Met Arg Leu Leu Arg Met Glu Ser Glu Glu
                85                  90                  95

Leu Ala Asp Arg Val Leu Asp Val Val Glu Arg Ser Leu Ser Asn Tyr
            100                 105                 110

Pro Phe Asp Phe Gln Gly Ala Arg Ile Ile Thr Gly Gln Glu Glu Gly
        115                 120                 125

Ala Tyr Gly Trp Ile Thr Ile Asn Tyr Leu Leu Gly Lys Phe Ser Gln
    130                 135                 140

Lys Thr Arg Trp Phe Ser Ile Val Pro
145                 150


<210> SEQ ID NO 14
<211> LENGTH: 154
<212> TYPE: PRT
<213> ORGANISM: Rattus norvegicus

<400> SEQUENCE: 14

Val Lys Tyr Gly Ile Val Leu Asp Ala Gly Ser Ser His Thr Asn Leu
1               5                   10                  15

Tyr Ile Tyr Lys Trp Pro Ala Glu Lys Glu Asn Asp Thr Gly Val Val
            20                  25                  30

Gln Leu Leu Glu Glu Cys Gln Val Lys Gly Pro Gly Ile Ser Lys Tyr
        35                  40                  45

Ala Gln Lys Thr Asp Glu Ile Ala Ala Tyr Leu Ala Glu Cys Met Lys
    50                  55                  60

Met Ser Thr Glu Arg Ile Pro Ala Ser Lys Gln His Gln Thr Pro Val
65                  70                  75                  80

Tyr Leu Gly Ala Thr Ala Gly Met Arg Leu Leu Arg Met Glu Ser Lys
                85                  90                  95

Gln Ser Ala Asp Glu Val Leu Ala Ala Val Ser Arg Ser Leu Lys Ser
            100                 105                 110

Tyr Pro Phe Asp Phe Gln Gly Ala Lys Ile Ile Thr Gly Gln Glu Glu
        115                 120                 125

Gly Ala Tyr Gly Trp Ile Thr Ile Asn Tyr Leu Leu Gly Arg Phe Thr
    130                 135                 140

Gln Glu Gln Ser Trp Leu Asn Phe Ile Ser
145                 150
```

-continued

<210> SEQ ID NO 15
<211> LENGTH: 153
<212> TYPE: PRT
<213> ORGANISM: Homo sapiens

<400> SEQUENCE: 15

```
Lys Tyr Gly Ile Val Leu Asp Ala Gly Ser Ser His Thr Ser Met Phe
1               5                   10                  15

Ile Tyr Lys Trp Pro Ala Asp Lys Glu Asn Asp Thr Gly Ile Val Gly
            20                  25                  30

Gln His Ser Ser Cys Asp Val Pro Gly Gly Gly Ile Ser Ser Tyr Ala
        35                  40                  45

Asp Asn Pro Ser Gly Ala Ser Gln Ser Leu Val Gly Cys Leu Glu Gln
    50                  55                  60

Ala Leu Gln Asp Val Pro Lys Glu Arg His Ala Gly Thr Pro Leu Tyr
65                  70                  75                  80

Leu Gly Ala Thr Ala Gly Met Arg Leu Leu Asn Leu Thr Asn Pro Glu
                85                  90                  95

Ala Ser Thr Ser Val Leu Met Ala Val Thr His Thr Leu Thr Gln Tyr
            100                 105                 110

Pro Phe Asp Phe Arg Gly Ala Arg Ile Leu Ser Gly Gln Glu Glu Gly
        115                 120                 125

Val Phe Gly Trp Val Thr Ala Asn Tyr Leu Leu Glu Asn Phe Ile Lys
    130                 135                 140

Tyr Gly Trp Val Gly Arg Trp Phe Arg
145                 150
```

<210> SEQ ID NO 16
<211> LENGTH: 150
<212> TYPE: PRT
<213> ORGANISM: Gallus gallus

<400> SEQUENCE: 16

```
Phe Lys Tyr Gly Ile Val Leu Asp Ala Gly Ser Ser His Thr Ala Val
1               5                   10                  15

Phe Ile Tyr Lys Trp Pro Ala Asp Lys Glu Asn Asp Thr Gly Val Val
            20                  25                  30

Ser Glu His Ser Met Cys Asp Val Glu Gly Pro Gly Ile Ser Ser Tyr
        35                  40                  45

Ser Ser Lys Pro Pro Ala Ala Gly Lys Ser Leu Glu His Cys Leu Ser
    50                  55                  60

Gln Ala Met Arg Asp Val Pro Lys Glu Lys His Ala Asp Thr Pro Leu
65                  70                  75                  80

Tyr Leu Gly Ala Thr Ala Gly Met Arg Leu Leu Thr Ile Ala Asp Pro
                85                  90                  95

Pro Ser Gln Thr Cys Leu Ser Ala Val Met Ala Thr Leu Lys Ser Tyr
            100                 105                 110

Pro Phe Asp Phe Gly Gly Ala Lys Ile Leu Ser Gly Glu Glu Glu Gly
        115                 120                 125

Val Phe Gly Trp Ile Thr Ala Asn Tyr Leu Leu Glu Asn Phe Ile Lys
    130                 135                 140

Arg Gly Trp Leu Gly Glu
145                 150
```

<210> SEQ ID NO 17
<211> LENGTH: 148

-continued

<212> TYPE: PRT
<213> ORGANISM: Caenorhabditis elegans

<400> SEQUENCE: 17

```
Ile Lys Tyr Gly Val Ile Cys Asp Ala Gly Ser Ser Gly Thr Arg Leu
1               5                   10                  15

Phe Val Tyr Thr Leu Lys Pro Leu Ser Gly Gly Leu Thr Asn Ile Asp
            20                  25                  30

Thr Leu Ile His Glu Ser Glu Pro Val Val Lys Lys Val Thr Pro Gly
        35                  40                  45

Leu Ser Ser Phe Gly Asp Lys Pro Glu Gln Val Val Glu Tyr Leu Thr
    50                  55                  60

Pro Leu Leu Arg Phe Ala Glu Glu His Ile Pro Tyr Glu Gln Leu Gly
65                  70                  75                  80

Glu Thr Asp Leu Leu Ile Phe Ala Thr Ala Gly Met Arg Leu Leu Pro
                85                  90                  95

Glu Ala Gln Lys Asp Ala Ile Ile Lys Asn Leu Gln Asn Gly Leu Lys
            100                 105                 110

Ser Val Thr Ala Leu Arg Val Ser Asp Ser Asn Ile Arg Ile Ile Asp
        115                 120                 125

Gly Ala Trp Glu Gly Ile Tyr Ser Trp Ile Ala Val Asn Tyr Ile Leu
    130                 135                 140

Gly Arg Phe Asp
145
```

<210> SEQ ID NO 18
<211> LENGTH: 10
<212> TYPE: RNA
<213> ORGANISM: Mus musculus

<400> SEQUENCE: 18
aagaauaugg 10

<210> SEQ ID NO 19
<211> LENGTH: 10
<212> TYPE: RNA
<213> ORGANISM: Vertebrate

<400> SEQUENCE: 19
gccgccaugg 10

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ccagactgta aatcttttgg 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agggaatgta ataagggtag 20

-continued

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ctgcttgagt gacgtctctg 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cacatgaggt tcagctcgtg 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gtgaagtggc tgccttcagg 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cctttgactc gggactccag 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gaactgctgc ctaaccactc 20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
attgatgggt cttgggattg c 21

<210> SEQ ID NO 28
<211> LENGTH: 10
<212> TYPE: RNA
<213> ORGANISM: Homo sapiens

<400> SEQUENCE: 28

-continued

```
augugaauga                                                              10


<210> SEQ ID NO 29
<211> LENGTH: 10
<212> TYPE: RNA
<213> ORGANISM: Homo sapiens

<400> SEQUENCE: 29

acaaggauga                                                              10


<210> SEQ ID NO 30
<211> LENGTH: 6
<212> TYPE: RNA
<213> ORGANISM: Homo sapiens

<400> SEQUENCE: 30

aauaaa                                                                   6


<210> SEQ ID NO 31
<211> LENGTH: 20
<212> TYPE: DNA
<213> ORGANISM: Homo sapiens

<400> SEQUENCE: 31

caggtcactt atggagcctg                                                   20


<210> SEQ ID NO 32
<211> LENGTH: 18
<212> TYPE: DNA
<213> ORGANISM: Homo sapiens

<400> SEQUENCE: 32

ccatggacaa aataggac                                                     18
```

METHODS AND COMPOSITIONS RELATING TO CD39-LIKE POLYPEPTIDES AND NUCLEIC ACIDS

This application is a continuation application of U.S. application Ser. No. 09/240,639, now U.S. Pat. No. 6,350,447, filed on Jan. 29, 1999, entitled "Methods and Compositions Relating to CD-39-like Polypeptides and Nucleic Acids," which is herein incorporated by reference in its entirety.

1. FIELD OF THE INVENTION

The present invention provides novel polynucleotides and proteins encoded by such polynucleotides, along with therapeutic, diagnostic and research utilities for these polynucleotides and proteins.

2. BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). In addition, more recently, "indirect" cloning techniques have been utilized, such as signal sequence cloning, which isolates DNA sequences based on the presence of a now well-recognized secretory leader sequence motif, as well as various PCR-based or low stringency hybridization cloning techniques, coupled in certain instances with database searching, have advanced the state of the art by making available large numbers of DNA/amino acid sequences for proteins that are known to have biological activity by virtue of their secreted nature in the case of leader sequence cloning, by virtue of the cell or tissue source in the case of PCR-based techniques and/or by virtue of their sequence similarity via database searches. It is to these proteins and the polynucleotides encoding them that the present invention is directed.

3. SUMMARY OF THE INVENTION

The compositions of the present invention include novel isolated polypeptides, in particular, novel CD-39-like polypeptides, isolated polynucleotides encoding such polypeptides, including recombinant DNA molecules, cloned genes or degenerate variants thereof, especially naturally occurring variants such as allelic variants, and antibodies that specifically recognize one or more epitopes present on such polypeptides.

The compositions of the present invention additionally include vectors, including expression vectors, containing the polynucleotides of the invention, cells genetically engineered to contain such polynucleotides and cells genetically engineered to express such polynucleotides.

The isolated polynucleotides of the invention include, but are not limited to, a polynucleotide encoding a polypeptide comprising the amino acid sequence of SEQ ID NO:2 (also referred to herein as "CD39L2"); or a polynucleotide encoding a polypeptide comprising amino acid residues 72–93, 147–162, 191–211 OR 217–238 of SEQ ID NO:2.

In selected embodiments, such isolated polynucleotides of the invention represents a polynucleotide comprising the nucleotide sequence of SEQ ID NO:1; or a polynucleotide comprising nucleotides 232–1599, 445–510, 670–717, 802–864 or 880–945 of the nucleotide sequence of SEQ ID NO:1.

The polynucleotides of the present invention also include, but are not limited to, a polynucleotide that hybridizes to the complement of the nucleotide sequence of SEQ ID NO:1 under highly stringent hybridization conditions; a polynucleotide that hybridizes to the complement of the nucleotide sequence of SEQ ID NO:1 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:2.

The isolated polynucleotides of the invention still further include, but are not limited to, a polynucleotide encoding a polypeptide comprising the amino acid sequence of SEQ ID NO:4 (also referred to herein as "CD39L3"); or a polynucleotide encoding a polypeptide comprising amino acid residues 55–76, 132–150, 177–199 or 213–234 of SEQ ID NO:4.

In selected embodiments, such isolated polynucleotides of the invention represents a polynucleotide comprising the nucleotide sequence of SEQ ID NO:3; or a polynucleotide comprising nucleotides 83–1669, 245–310, 476–532, 611–679 or 719–784 of the nucleotide sequence of SEQ ID NO:3.

The polynucleotides of the present invention also include, but are not limited to, a polynucleotide that hybridizes to the complement of the nucleotide sequence of SEQ ID NO:3 under highly stringent hybridization conditions; a polynucleotide that hybridizes to the complement of the 1nucleotide sequence of SEQ ID NO:3 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:4.

The isolated polynucleotides of the invention still further include, but are not limited to, a polynucleotide encoding a polypeptide comprising the amino acid sequence of SEQ ID NO:6 (also referred to herein as "CD39L4"); or a polynucleotide encoding a polypeptide comprising amino acid residues 47–68, 123–138, 167–187 or 193–214 of SEQ ID NO:6; or a polynucleotide encoding a polypeptide comprising the amino acid sequence of SEQ ID NO:9 (also referred to herein as dCD39L4"); or a polynucleotide encoding amino acid residues 77–98, 153–167, 197–217 or 223–242 of SEQ ID NO:9.

In one embodiment, such isolated polynucleotides of the invention represents a polynucleotide comprising the nucleotide sequence of SEQ ID NO:5; or a polynucleotide comprising nucleotides 247–1530, 385–450, 613–660, 745–807 or 823–888 of the nucleotide sequence of SEQ ID NO:5.

The polynucleotides of the present invention also include, but are not limited to, a polynucleotide that hybridizes to the complement of the nucleotide sequence of SEQ ID NO:5 under highly stringent hybridization conditions; a polynucleotide that hybridizes to the complement of the nucleotide sequence of SEQ ID NO:5 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:6.

The isolated polynucleotides of the invention further include, but are not limited to, a polynucleotide encoding a polypeptide comprising the amino acid sequence of SEQ ID NO:8 (also referred to herein as "mCD39L4" or "mNTPase"); or a polynucleotide encoding amino acid residues 46–67, 122–140, 166–187 or 194–213 of SEQ ID NO:8.

In selected embodiments, such isolated polynucleotides of the invention represents a polynucleotide comprising the nucleotide sequence of SEQ ID NO:7; or a polynucleotide comprising nucleotides 205–1599, 340–395, 568–624, 700–765 or 784–843 of the nucleotide sequence of SEQ ID NO:7.

The polynucleotides of the present invention also include, but are not limited to, a polynucleotide that hybridizes to the complement of the nucleotide sequence of SEQ ID NO:7 under highly stringent hybridization conditions; a polynucleotide that hybridizes to the complement of the nucleotide sequence of SEQ ID NO:7 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:8.

The polynucleotides of the invention additionally include the complement of any of the polynucleotides recited above.

The isolated polypeptides of the invention further include, but are not limited to, a polypeptide comprising the amino acid sequence of SEQ ID NO:2; or a polypeptide comprising amino acid residues 72–93, 147–162, 191–211 OR 217–238 of SEQ ID NO:2.

The isolated polypeptides of the invention still further include, but are not limited to, a polypeptide comprising the amino acid sequence of SEQ ID NO:4; or a polypeptide comprising amino acid residues 55–76, 132–150, 179–199 or 213–234 of SEQ ID NO:4.

The isolated polypeptides of the invention include, but are not limited to, a polypeptide comprising the amino acid sequence of SEQ ID NO:6; or a polypeptide comprising amino acid residues 47–68, 123–138, 167–187 or 193–214 of SEQ ID NO:6.

The isolated polypeptides of the invention include, but are not limited to, a polypeptide comprising the amino acid sequence of SEQ ID NO:8; or a polypeptide comprising amino acid residues 46–67, 122–140, 166–187 or 194–213 of SEQ ID NO:8.

The isolated polypeptides of the invention include, but are not limited to, a polypeptide comprising the amino acid sequence of SEQ ID NO:9; or a polypeptide comprising amino acid residues 77–98, 153–167, 197–217 or 223–242 of SEQ ID NO:9.

Preferred embodiments include polypeptides that represent is mature forms of the polypeptides of the invention.

Polypeptide compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture or from an extract of the cells.

Polynucleotides according to the invention have numerous applications in a variety of techniques known to those skilled in the art of molecular biology. These techniques include use as hybridization probes, use as primers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, the polypeptides of the invention can be used as molecular weight markers, and as a food supplement. In addition, a polypeptide of the invention can be used to generate an antibody that specifically binds the polypeptide.

Methods are also provided for preventing, treating or ameliorating a medical condition which comprises administering to a mammalian subject a therapeutically effective amount of a composition comprising a protein of the present invention and a pharmaceutically acceptable carrier.

The polypeptides and polynucleotides of the invention can be utilized, for example, as part of methods for modulating ecto-ATPase activity and for identifying compounds that can be utilized as part of methods for modulating ecto-ATPase activity. Among the processes that can be modulated via such methods are processes involved in cell adhesion, apoptosis, vesicular transport, signalling, including purinergic, synaptic and neurotransmitter signalling, and purine recycling. The polypeptides of the invention having ADPase activity are also useful as anticoagulants and for inhibiting platelet aggregation. The polypeptides of the invention can further be utilized as anti-thrombotic agents, anti-tissue graft rejection agents, and/or as part of methods for regulating neurotransmission by ATP in smooth muscle, peripheral ganglia or the brain.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The invention also provides methods for the identification of compounds that modulate the expression of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention.

The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

4. BRIEF DESCRIPTION OF THE FIGURES

FIGS. 1A, 1B, 1C, 1D, 1E, and 1F. Top line: Nucleotide sequence of SEQ ID NO: 7, referred to herein as mNTPase or mCD39L4; bottom line: amino acid sequence of SEQ ID NO: 8, referred to herein as mNTPase or mCD39L4.

FIGS. 2A, 2B, and 2C. Amino acid alignments of the full mNTPase (mCD39L4) amino acid sequence (SEQ ID NO:8) and the most closely related other NTPase proteins: garden pea NTpase (SEQ ID NO:10), potato apyrase (SEQ ID NO:11), yeast GDPase (SEQ ID NO:12). Identical residues are indicated by double underlining, while conserved residues are indicated by single underlining. Alignments were made with pileup and boxshade from the Wisconsin Package Version 9.0, Genetics Computer Group (GCG), Madison Wis.

FIGS. 3A, 3B, 3C, and 3D. Alignment of 12 members of the NTPase (or CD39-like) gene family indicating the conserved apryase regions I–IV. CD39=human (from Accession No. S73813; SEQ ID NO:13), ratCD39=rat (from Accession No. gi11754710; SEQ ID NO: 14), CD39L1=human (Accession No. U91510; SEQ ID NO:15), ChiATPase=chicken (from Accession No. U74467; SEQ ID NO:16), peaNTPase=garden pea (from Accession No. P52914; SEQ ID NO:10), potRROP1=potato RROP1 gene (from Accession No. gi11381633; SEQ ID NO:11), yGDA1+y71 KD=yeast genes (from Accession Nos. sp1P32621+sp1P40009; SEQ ID NO: 12), hCD39L2=CD39L2, celegans=*C. Elegans* gene (from Accession No. gi11086594; SEQ ID NO:17). Identical residues are indicated by double underlining, conserved residues are indicated by single underlining. Alignments were made with pileup and boxshade from the Wisconsin Package 9.0, Genetics Computer Group (GCG), Madison, Wis. Conserved portions of ACRs I–IV are boxed.

FIGS. 4A, 4B, 4C, 4D, 4E, 4F, 4G, and 4H. Top line: Nucleotide sequence of SEQ ID NO:1, referred to herein as CD39L2; bottom line: amino acid sequence of SEQ ID NO:2, referred to herein as CD39L2.

FIGS. 5A, 5B, 5C, 5D, and 5E. Comparison of the hydrophobicity predictions for the amino acid sequences of members of the human CD39-like gene family. Predictions were made using the Topred-II 1.1 program (Claros, M. G. & Von Hejine, G., 1994, Comput. Appl. Biosci. 10:685–686; putative setting=0.5; certain setting=1.0).

FIGS. 6A, 6B, 6C, 6D, 6E, 6F, 6G, and 6H. Top line: Nucleotide sequence of SEQ ID NO:3, referred to herein as CD39L3; bottom line: amino acid sequence of SEQ ID NO:4, referred to herein as CD39L3.

FIGS. 7A, 7B, 7C, 7D, 7E, and 7F. Top line: Nucleotide sequence of SEQ ID NO:5, referred to herein as CD39L4; bottom line: amino acid sequence of SEQ ID NO:6, referred to herein as CD39L4.

FIGS. 8A, 8B, 8C, and 8D. Amino acid alignments of the full-length protein sequences for human members of the CD39-like gene family. CD39 (from Accession No. S73813; SEQ ID NO:13), CD39L1 (from Accession No. U91510; SEQ ID NO: 15), CD39L2 (it is noted that the CD39L2 polypeptide illustrated here depicts a derived amino acid sequence that is encoded from the ATG codon beginning at nucleotide 148 (see FIG. 4A) and, therefore, includes an additional 28 amino acid residues N-terminal to those depicted in FIG. 4A; this form of CD39L2 is also intended to be included within the scope of the present invention), CD39L3, CD39L4.

Identical residues are indicated by double underlining and conserved residues are indicated by single underlining. Spaces in the sequences are indicated by a dash. Apyrase regions (ACRs) are indicated by arrows, with conserved portions of ACRs I–IV are highlighted by the boxed sections. Alignments were made using pileup and boxshade from the Wisconsin Package Version 9.0 Genetics Computer Group (GCG), Madison, Wis.

FIGS. 9A, 9B, 9C, 9D, and 9E. Amino acid sequence of dCD39L4("dNTPase"; SEQ ID NO:9) and alignment of the amino acid sequence with the most closely related members of the CD39-like gene family. peaGDP, garden pea NTPase (from Accession No. P52194; SEQ ID NO:10); ptoapyrase, potato RROP1 gene (from Accession No. gi11381633; SEQ ID NO:11); CD39L2; CD39L4, and yGDPase, yeast yGDA1 gene (from Accession No. sp1P32621; SEQ ID NO:12). Apyrase regions (ACRs) are indicated by arrows, with conserved portions of ACRs I–IV are highlighted by the boxed sections.

5. DETAILED DESCRIPTION OF THE INVENTION

5.1. Definitions

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. In alternate embodiments, a nucleotide sequence, polynucleotide or nucleic acid can correspond to a genomic sequence (e , can contain intron as well as exon sequence) or cDNA sequences (that is, contains no intron sequence).

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold spring Harbor Laboratory, NY; or Ausubel, F. M. et al., 1989, Current Protocols in Molecular Biology, John Wiley & Sons, New York N.Y., both of which are incorporated herein by reference in their entirety.

The "oligonucleotide fragment," "polynucleotide fragment," "portion," "segment,", "oligonucleotide" or "nucleic acid probe" is at least about 15, and preferably at least about 50, 100, 200, 300, 400, 500, 600, 700 or 800 nucleotides in length.

The term "stringent" is used to refer to conditions that are commonly understood in the art as stringent. Stringent conditions can include highly stringent conditions (i.e., hybridization to filter-bound DNA under in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.).

In instances wherein hybridization of deoxyoligonucleotides is concerned, additional exemplary highly stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation-and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endoqenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMP. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biological and/or immunological activities of any naturally occurring polypeptide.

The term "biologically active" refers to the biological activity of a naturally occurring polypeptide as well as to the ability of the polypeptide to exhibit an immunological activity. A polypeptide exhibits an "immunological activity" when antibodies can be generated that are directed against the polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "mature" refers to a polypeptide that has been postranslationally modified or that corresponds in primary amino acid sequence to a polypeptide that has been postranslationally modified. A mature polypeptide includes, but is not limited to, a polypeptide which comprises a primary amino acid sequence that has been processed from a "dpre-," "pro-," or "pre-pro" amino acid sequence; a polypeptide which comprises a primary amino acid sequence corresponding to that of a polypeptide that has been processed from a "pre-," "pro-," or "pre-pro" amino acid sequence; a polypeptide that has been post-translationally modified via such modifications as, for example, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a epolypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20%, i.e., the number of individual residue substitutions, additions, and/or deletions in a substantially equivalent sequence, as compared to the corresponding reference sequence, divided by the total number of residues in the substantially equivalent sequence is about 0.2 or less. Such a sequence is said to have 80% sequence identity to the listed sequence. Such a substantially equivalent sequence can be routinely identified by applying the foregoing algorithm.

In one embodiment, a substantially equivalent, e.g., mutant, sequence of the invention varies from a listed sequence by no more than 10%, i.e., the number of individual residue substitutions, additions, and/or deletions in a substantially equivalent sequence, as compared to the corresponding reference sequence, divided by the total number of residues in the substantially equivalent sequence is about 0.1 or less. Such a sequence is said to have 90% sequence identity to the listed sequence. Such a substantially equivalent sequence can be routinely identified by applying the foregoing algorithm.

In an alternate embodiment a substantially equivalent sequence of the invention varies from a listed sequence by no more than by no more than 5%, i.e., the number of individual residue substitutions, additions, and/or deletions in a substantially equivalent sequence, as compared to the corresponding reference sequence, divided by the total number of residues in the substantially equivalent sequence is about 0.05 or less. Such a sequence is said to have 95% sequence identity to the listed sequence. Such a substantially equivalent sequence can be routinely identified by applying the foregoing algorithm.

In yet another alternate embodiment, a substantially equivalent sequence of the invention varies from a listed sequences by no more than 2%, i.e., the number of individual residue substitutions, additions, and/or deletions in a substantially equivalent sequence, as compared to the corresponding reference sequence, divided by the total number of residues in the substantially equivalent sequence is about 0.02 or less. Such a sequence is said to have 98% sequence identity to the listed sequence. Such a substantially equivalent sequence can be routinely identified by applying the foregoing algorithm.

Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. In a preferred embodiment, for the purposes of determining equivalence, truncation of the mature sequence (e.g., via a mutation which creates a spurious stop codon) are disregarded.

Nucleic acid sequences encoding such substantially equivalent sequences, e.g., sequences of the recited percent identities, can also routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids or about at least about 9 to 13 amino acids, and, in various embodiments, at least about 17, 25, 50, 75, 100, 150, 200, 300, 400 or more amino acids. To be "active," any polypeptide must have sufficient length to display biologic and/or immunologic activity.

Recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate. Such variant nucleic acids and polypeptides are to be considered part of the present invention.

The term "activated" cells as used herein refers to those cells that are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between about 5 and about 1000 bases in length. In various embodiments, such nucleic acids are between about 10 and about 40 bp in length, or at least about 100, 200, 300, 400, 20 500, 600, 700, 800 or 900 bp in length.

The term "secreted" protein refers to a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors, including seven-transmembrane receptors) from the cell in which they are expressed. "Secreted" proteins also include without limitation proteins which are transported across the membrane of the endoplasmic reticulum. Each of the above terms is meant to encompasses all that is described for each, unless the context dictates otherwise.

Polynucleotides and Nucleic Acids of the Invention

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length forms of the polypeptides of the invention are identified in the figures and the sequence listing by translation of the nucleotide sequence of each nucleic acid molecule. Mature forms of the polypeptides of the invention can routinely be obtained by expression of the disclosed nucleotides encoding the full-length polypeptides in a suitable mammalian cell or other host cell. The sequence of the mature forms of the polypeptides can also routinely be determined from the amino acid sequence of the full-length polypeptides.

The present invention also provides genes corresponding to cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Species homologs of the disclosed polynucleotides and proteins are also provided by the present invention. Species homologs may be isolated and identified by making suitable probes or primers from the sequences provided herein and screening a suitable nucleic acid source from the desired species. Species homologs can include, but are not limited to human, murine, rat or Drosophila species homologs.

The invention also encompasses allelic variants of the disclosed polynucleotides or proteins; that is, naturally-occurring alternative forms of the isolated polynucleotide which also encode proteins which are identical, homologous or related to that encoded by the polynucleotides. Sequences and allelic variant sequences of the invention can include, but are not limited to human, murine, rat and Drosophila sequences.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

5.2. Nucleic Acids of the Invention

The isolated polynucleotides of the invention include, but are not limited to, a polynucleotide encoding a polypeptide comprising the amino acid sequence of SEQ ID NO:2 (also referred to herein as "CD39L2"); or a polynucleotide encoding a polypeptide comprising amino acid residues 72–93, 147–162, 191–211 OR 217–238 of SEQ ID NO:2.

In selected embodiments, such isolated polynucleotides of the invention represents a polynucleotide comprising the nucleotide sequence of SEQ ID NO:1; or a polynucleotide comprising nucleotides 232–1599, 445–510, 670–717, 802–864 or 880–945 of the nucleotide sequence of SEQ ID NO:1.

The polynucleotides of the present invention also include, but are not limited to, a polynucleotide that hybridizes to the complement of the nucleotide sequence of SEQ ID NO:1 under highly stringent hybridization conditions; a polynucleotide that hybridizes to the complement of the nucleotide sequence of SEQ ID NO:1 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:2. Such polynucleotides hybridize under the above conditions to the complement of SEQ ID NO:1 or to a fragment of SEQ ID NO:1, wherein the fragment is greater than at least about 10 bp, and, in alternate embodiments, is about 20 to about 50 bp, or is greater than about 100 bp, 200 bp, 300 bp, 400 bp, 500 bp, 600 bp, 700 bp, or 800 bp.

The isolated polynucleotides of the invention still further include, but are not limited to, a polynucleotide encoding a polypeptide comprising the amino acid sequence of SEQ ID NO:4 (also referred to herein as "CD39L3"); or a polynucleotide encoding a polypeptide comprising amino acid residues 55–76, 132–150, 179–199 or 213–234 of SEQ ID NO:4.

In selected embodiments, such isolated polynucleotides of the invention represents a polynucleotide comprising the nucleotide sequence of SEQ ID NO:3; or a polynucleotide comprising nucleotides 83–1669, 245–310, 476–532, 611–679 or 719–784 of the nucleotide sequence of SEQ ID NO:3.

The polynucleotides of the present invention also include, but are not limited to, a polynucleotide that hybridizes to the complement of the nucleotide sequence of SEQ ID NO:3 under highly stringent hybridization conditions; a polynucleotide that hybridizes to the complement of the nucleotide sequence of SEQ ID NO:3 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:4. Such polynucleotides hybridize under the above conditions to the complement of SEQ ID NO:3 or to a fragment of SEQ ID NO:3, wherein the fragment is greater than at least about 10 bp, and, in alternate embodiments, is about 20 to about 50 bp, or is greater than about 100 bp, 200 bp, 300 bp, 400 bp, 500 bp, 600 bp, 700 bp, or 800 bp.

The isolated polynucleotides of the invention still further include, but are not limited to, a polynucleotide encoding a polypeptide comprising the amino acid sequence of SEQ ID NO:6 (also referred to herein as "CD39L4"); or a polynucleotide encoding a polypeptide comprising amino acid residues 47–68, 123–138, 167–187 or 193–214 of SEQ ID NO:6; or a polynucleotide encoding a polypeptide comprising the amino acid sequence of SEQ ID NO:9 (also referred to herein as dCD39L4"); or a polynucleotide encoding amino acid residues 77–98, 153–167, 197–217 or 223–242 of SEQ ID NO:9.

In one embodiment, such isolated polynucleotides of the invention represents a polynucleotide comprising the nucleotide sequence of SEQ ID NO:5; or a polynucleotide comprising nucleotides 247–1530, 385–450, 613–660, 745–807 or 823–888 of the nucleotide sequence of SEQ ID NO:5.

The polynucleotides of the present invention also include, but are not limited to, a polynucleotide that hybridizes to the complement of the nucleotide sequence of SEQ ID NO:5 under highly stringent hybridization conditions; a polynucleotide that hybridizes to the complement of the nucleotide sequence of SEQ ID NO:5 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ IP NO:6. Such polynucleotides hybridize under the above conditions to the complement of SEQ ID NO:5 or to a fragment of SEQ ID NO:5, wherein the fragment is greater than at least about 10 bp, and, In alternate embodiments, is about 20 to about 50 bp, or is greater than about 100 bp, 200 bp, 300 bp, 400 bp, 500 bp, 600 bp, 700 bp or 800 bp.

The isolated polynucleotides of the invention further include, but are not limited to, a polynucleotide encoding a polypeptide comprising the amino acid sequence of SEQ ID NO:8 (also referred to herein as "mCD39L4" or "mNTPase"); or a polynucleotide encoding amino acid residues 46–67, 122–140, 166–187 or 194–213 of SEQ ID NO:8.

In selected embodiments, such isolated polynucleotides of the invention represents a polynucleotide comprising the nucleotide sequence of SEQ ID NO:7; or a polynucleotide comprising nucleotides 205–1599, 340–395, 568–624, 700–765 or 784–843 of the nucleotide sequence of SEQ ID NO:7.

The polynucleotides of the present invention also include, but are not limited to, a polynucleotide that hybridizes to the complement of the nucleotide sequence of SEQ ID NO:7 under highly stringent hybridization conditions; a polynucleotide that hybridizes to the complement of the nucleotide sequence of SEQ ID NO:7 under moderately stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO:8. Such polynucleotides hybridize under the above conditions to the complement of SEQ ID NO:7 or to a fragment of SEQ ID NO:7, wherein the fragment is greater than at least about 10 bp, and, in alternate embodiments, is about 20 to about 50 bp, or is greater than about 100 bp, 200 bp, 300 bp, 400 bp, 500 bp, 600 bp, 700 bp or 800 bp.

The polynucleotides of the invention additionally include the complement of any of the polynucleotides recited above.

The polynucleotides of the invention also provide polynucleotides that are substantially equivalent to the polynucleotides recited above. Typically, such a substantially equivalent sequence varies from one of those listed herein by no more than about 20%, i.e., the number of individual nucleotide substitutions, additions, and/or deletions in a substantially equivalent sequence, as compared to the corresponding reference sequence, divided by the total number of nucleotides in the substantially equivalent sequence is about 0.2 or less. Such a sequence is said to have 80% sequence identity to the listed sequence. Such a substantially equivalent sequence can be routinely identified by applying the foregoing algorithm.

In one embodiment, a substantially equivalent polynucleotide sequence of the invention varies from a listed sequence by no more than 10%, i.e., the number of individual nucleotide substitutions, additions, and/or deletions in a substantially equivalent sequence, as compared to the corresponding reference sequence, divided by the total number of nucleotides in the substantially equivalent sequence is about 0.1 or less. Such a sequence is said to have 90% sequence identity to the listed sequence. Such a substantially equivalent sequence can be routinely identified by applying the foregoing algorithm.

In an alternate embodiment a substantially equivalent sequence of the invention varies from a listed sequence by no more than by no more than 5%, i.e., the number of individual nucleotide substitutions, additions, and/or deletions in a substantially equivalent sequence, as compared to the corresponding reference sequence, divided by the total number of nucleotides in the substantially equivalent sequence is about 0.05 or less. Such a sequence is said to have 95% sequence identity to the listed sequence. Such a substantially equivalent sequence can be routinely identified by applying the foregoing algorithm.

In yet another alternate embodiment, a substantially equivalent sequence of the invention varies from a listed sequences by no more than 2%, i.e., the number of individual nucleotide substitutions, additions, and/or deletions in a substantially equivalent sequence, as compared to the corresponding reference sequence, divided by the total number of nucleotides in the substantially equivalent sequence is about 0.02 or less. Such a sequence is said to have 98% sequence identity to the listed sequence. Such a substantially equivalent sequence can be routinely identified.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NO:1, SEQ ID NO:3, SEQ ID NO:5 or SEQ ID NO:7, a representative intermediate fragment thereof, or a nucleotide sequence at least 99.9% identical to SEQ ID NO:1, SEQ ID NO:3, SEQ ID NO:5 or SEQ ID NO:7 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

It is to be understood that nucleic acid molecules consisting of the following nucleotide sequences are not considered part of the present invention: the nucleotide sequence or, where appropriate, the nucleotide sequence that encodes the depicted amino acid sequence, of Genbank™ accession number S73813, gi11754710, U91510, U91511, AA116990, AA120757, H08436, AA378537, AA336644, AA338117, AA337885, N72742, AA256016, AA611283, AA647051, AA638277, AA271520, W46136, AA391695, AA390461, AA201196, AA246996, AA567512 or AC002032.

The present invention further provides recombinant constructs comprising a nucleic acid having the sequence of SEQ ID NO:1, SEQ ID NO:3, SEQ ID NO:5, or SEQ ID NO:7 or an intermediate fragment thereof, or another of the nucleic acid molecules of the invention. The recombinant constructs of the present invention comprise a vector, such as a plasmid or viral vector, into which a nucleic acid having the sequence of SEQ ID NO:1, SEQ ID NO:3, SEQ ID NO:5 or SEQ ID NO:7, or an intermediate fragment thereof, or another of the nucleic acid molecules of the invention, is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotides of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Pine Chemicals, Uppsala, Sweden) and GEM 1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res*. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., *Gene* 3:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Finally, it is to be understood that the nucleic acid molecules of the invention further include any nucleic acid molecule that encodes the polypeptides of the invention, as described in Section 5.4, below.

5.3. Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of the EDF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual*, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the, control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

5.4. Polyeptides of the Invention

The isolated polypeptides of the invention include, but are not limited to, a polypeptide comprising the amino acid sequence of SEQ ID NO:2; or a polypeptide comprising amino acid residues 72–93, 147–162, 191–211 OR 217–238 of SEQ ID NO:2.

The isolated polypeptides of the invention include, but are not limited to, a polypeptide comprising the amino acid sequence of SEQ ID NO:4; or a polypeptide comprising amino acid residues 55–76, 132–150, 179–199 or 213–234 of SEQ ID NO:4.

The isolated polypeptides of the invention include, but are not limited to, a polypeptide comprising the amino acid sequence of SEQ ID NO:6; or a polypeptide comprising amino acid residues 47–68, 123–138, 167–187 or 193–214 of SEQ ID NO:6.

The isolated polypeptides of the invention include, but are not limited to, a polypeptide comprising the amino acid sequence of SEQ ID NO:8; or a polypeptide comprising amino acid residues 46–67, 122–140, 166–187 or 194–213 of SEQ ID NO:8.

The isolated polypeptides of the invention include, but are not limited to, a polypeptide comprising the amino acid sequence of SEQ ID NO:9; or a polypeptide comprising amino acid residues 77–98, 153–167, 197–217 or 223–242 of SEQ ID NO:9.

The isolated polypeptides of the invention further include polypeptides that are substantially equivalent to the polypeptides of SEQ ID NO:2, SEQ ID NO:4, SEQ ID NO:6, SEQ ID NO:8 or SEQ ID NO:9 or to specific domains thereof. Typically, sucha substantially equivalent sequence varies from one of those listed herein by no more than about 20%, i.e., the number of individual amino acid residue substitutions, additions, and/or deletions in a substantially equivalent sequence, as compared to the corresponding reference sequence, divided by the total number of amino acid residues in the substantially equivalent sequence is about 0.2 or less. Such a sequence is said to have 80% sequence identity to the listed sequence. Such a substantially equivalent sequence can be routinely identified by applying the foregoing algorithm.

In one embodiment, a substantially equivalent polypeptide sequence of the invention varies from a listed sequence by no more than 10%, i.e., the number of individual amino acid substitutions, additions, and/or deletions in a substantially equivalent sequence, as compared to the corresponding reference sequence, divided by the total number of amino acid residues in the substantially equivalent sequence is about 0.1 or less. Such a sequence is said to have 90% sequence identity to the listed sequence. Such a substantially equivalent sequence can be routinely identified by applying the foregoing algorithm.

In an alternate embodiment a substantially equivalent sequence of the invention varies from a listed sequence by no more than by no more than 5%, i.e., the number of individual amino acid substitutions, additions, and/or deletions in a substantially equivalent sequence, as compared to the corresponding reference sequence, divided by the total number of amino acid residues in the substantially equivalent sequence is about 0.05 or less. Such a sequence is said to have 95% sequence identity to the listed sequence. Such a substantially equivalent sequence can be routinely identified by applying the foregoing algorithm.

In yet another alternate embodiment, a substantially equivalent sequence of the invention varies from a listed sequences by no more than 2%, i.e., the number of individual amino acid residue substitutions, additions, and/or deletions in a substantially equivalent sequence, as compared to the corresponding reference sequence, divided by the total number of amino acid residues in the substantially equivalent sequence is about 0.02 or less. Such a sequence is said to have 98% sequence identity to the listed sequence. Such a substantially equivalent sequence can be routinely identified.

Preferred embodiments include those in which the protein produced by such process is a mature form of the protein.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., scopes, *Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to the tumor or other cell by the specificity of the binding molecule for SEQ ID NO:2, SEQ ID NO:4 SEQ ID NO:6, SEQ ID NO:8 or SEQ ID NO:9, or another of the polypeptide of the invention.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat.RTH. kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl.RTM. or Cibacrom blue 3GA Sepharose.RTM.; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-s-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

It is to be understood that polypeptides consisting of the following amino acid sequence are not considered part of the present invention: the amino acid sequence of, or, where appropriate, reported to be encoded by the nucleotide sequence of Genbank™ accession No: S73813, gi11754710, U91510, U91511, AA116990, AA120757, H08436, AA378537, AA336644, AA338117, AA337885, N72742, AA256016, AA611283, AA647051, AA638277, AA271520, W46136, AA391695, AA390461, AA201196, AA246996 or AA567512.

5.5. Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

5.5.1. Research Uses and Utilities

The polynucleotides provided by the present invention can be used by the research community for various purposes.

The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

5.5.2. Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

5.5.3. Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMX.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan ads. Vol 1 pp. 6.13.1, John Wiley and Sons, Toronto. 1991.

Assays for T-cell clone responses to antigens (which will Identify, among others, proteins that affect APC-T cell interactions as well as direct T-cell effects by measuring proliferation and cytokine production) include, without limitation, those described in Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411. 1981; Takai et al., J. Immunol. 137:3494–3500, 1986; Takai et al., J. Immunol. 140:508–512, 1988.

5.5.4. Immune Stimulating or Suppressing Activity

A protein of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/1pr/1pr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-vital immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I a .alpha. chain protein and beta.sub.2 microglobulin protein or an MHC class II alpha. chain protein and an MHC class II .beta. chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et-al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowmanet al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorozyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

5.5.5. Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of bematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoiatic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

5.5.6. Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

5.5.7. Activin/Inhibin Activity

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin $\alpha$-family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-$\beta$ group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

5.5.8. Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

5.5.9. Hemostatic and Thrombolytic Activity

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

5.5.10. Recentor/Ligand Activity

A protein of the present invention may also demonstrate activity as receptors, receptor ligands or inhibitors or agonists of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

5.5.11. Anti-inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

5.5.12. Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, *Medicine*, 2d Ed., J.B. Lippincott Co., Philadelphia).

5.5.13. Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515);

increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.5.14. Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

5.6. Pharmaceutical Formulations and Routes of Administration

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the in invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

5.6.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

5.6.2. Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner in that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, orsynthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes; The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

5.6.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.6.4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

5.7. Antibodies

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., *Monoclonal Antibodies Technology: Laboratory Techniques in Biochemistry and Molecular Biology*, Elsevier Science Publishers, Amsterdam, The Netherlands (1984); St. Groth et al., *J. Immunol.* 35:1–21 (1990); Kohler and Milstein, Nature 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Research.* 175:109–124 (1988)). Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "*Handbook of Experimental Immunology*" 4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as for immuno-affinity purification of the proteins of the present invention.

5.8. Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. By providing the nucleotide sequence of SEQ ID NO:1 or a representative fragment thereof, or a nucleotide sequence at least 99.9% identical to SEQ ID NO:1in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

5.9. Triplex Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 15241:456 (1988); and Dervan et al., Science 251:1360 (1991)) or to the mRNA itself (antisense—Olmno, *J. Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

5.10. Diagnostic Assays and Kits

The present invention further provides methods to identify the presence or expression of one of the ORFs of the present invention, or homolog thereof, in a test sample, using a nucleic acid probe or antibodies of the present invention.

In general, methods for detecting a polynucleotide of the invention can comprise contacting a'sample with a compound that binds to and forms a complex with the polynucleotide for a period sufficient to form the complex, and detecting the complex, so that if a complex is detected, a polynucleotide of the invention is detected in the sample.

Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of immunoassays: Laboratory Techniques in Biochemistry and Molecular Biology*, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

5.11. Screening Assays

Using the isolated proteins and polynucleotides of the invention, the present invention further provides methods of obtaining and identifying agents which bind to a protein encoded by the ORF from a nucleic acid with a sequence of SEQ ID NO:1, to a specific domain of the polypeptide encoded by the nucleic acid, or to a nucleic acid with a sequence of SEQ ID NO:1. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," *In Synthetic Peptides, A User's Guide*, W.H. Freeman, NY (1992), pp. 289–307, and Kaspczak et al., *Biochemistry* 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, J. *Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

5.10. Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NO:1. Because the corresponding gene is only expressed in a limited number of tissues, especially adult tissues, a hybridization probe derived from SEQ ID NO:1 can be used as an indicator of the presence of RNA of cell type of such a tissue in a sample.

Any suitable hybridization technique can be employed, such as, for example, in situ hybridization. PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search. Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology that were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

6. EXAMPLE

Identification of Novel CD-39-like Nucleic Acid and Polynucleotide Molecules Described herein is the cloning and characterization of novel CD-39-like nucleotide-triphosphatase ("NTPase") gene and polypeptide sequences. These sequences are referred to below as "mNTPase", "mCD39L4" and "CD39L2."

First, a novel murine family member was cloned by low stringency screening of mouse cDNA libraries with a human CD39L1 cDNA clone (Chadwick, B. P. & Frischauf A.-M., 1997, Mamm. Genome 8:668672). A 1738 bp cDNA clone was isolated from an adult mouse testis cDNA library (Stratagene Ltd., Cambridge, UK) and sequenced. DNA sequence comparisons with the human CD39L1cDNA sequence showed moderate DNA homology of approximately 39% identity). An open reading frame (ORF) could be detected for the cNDA sequence, but indicated that the cDNA clone did not contain the initiation methionine codon and, therefore, did not extend to the 5' end. Database searches with the mouse cDNA sequence identified two mouse EST clones that extended the cDNA sequence at the 5' end (Accession Nos. AA116990 and AA120757). The EST clones were resequenced. The cloned and the resequenced nucleotide sequences were analyzed and were combined appropriately to yield the nucleotide sequence (SEQ ID NO:7) depicted in FIGS. 1A, 1B, 1C, 1D, 1E, and 1F, and referred to herein as mCD39L4 or mNTPase. The sequence revealed an ORF from nucleotides 205 to 1599 with the ATG at nucleotide 205 having a moderate match to the initiation start site for vertebrates (AAGAAUAUGG (SEO ID NO: 18) for mNTPase versus GCCGCCAUGG (SEQ ID NO: 19); Kozak, M., 1989, J. Biol. Chem. 108:229–241). The derived amino acid sequence is also shown in FIGS. 2A, 2B, and 2C (SEQ ID NO:8). No apparent polyadenylation signal existed, although the cDNA clone isolated contained a poly-A tail.

Hydropathy plots with Topred-II 1.1 (Claros, M. G. & Von Hejine, G., 1994, Comput. Appl. Biosci. 10:685–686) predict a single potential transmembrane segment close to the amino terminus of the protein, suggesting a single-pass transmembrane protein with a large extracellular domain. Two potential glycosylation sites can be found at amino acid positions 41 (NVSA) and at 231 (NSTF), suggesting that mNTPase is glycosylated.

Database searches with the derived amino acid sequence identified homology with other members of the NTPase family. FIGS. 2A, 2B, and 2C show an alignment of the full mNTPase (mCD39L4) protein sequence against three of the most homologous known NTPases, from garden pea, potato and *Saccharomyces cerevisiae*. The mNTPase protein shares approximately 30% amino acid identity with the three other NTPases.

The region of highest homology between all members of the NTPase family is at the amino terminus of the protein. Handa & Guidotti (Handa, M. & Guidotti, G., 1996, Biochem. Biophys. Res. Commun. 218:916–923) highlighted four regions of NTPases referred to as putative apyrase-conserved regions ("ACRs"). FIGS. 3A, 3B, 3C, and 3D show an alignment of ACRs I–IV. (See Section 3, Section 5, and its subsections, above, for a delineation of the amino acid residues that make up ACRs I–IV of the CD39-like polypeptides of the invention.) ACR conservation would indicate that these regions are essential for the functioning of the protein, while changes in the regions surrounding these domains can be tolerated. The presence of all four ACRs in the mNTPase (mCD39L2) indicates that mNTPase is a new member of the NTPase family.

BLAST searches with the DNA sequence of mNTPase (mCD39L4) revealed two overlapping human EST clones with 57% DNA sequence identity to portions of mNTPase (Accession Nos. H08436 and AA378537). Upon combination and analysis of the resulting sequence, an ORF was identified that showed homology to NTPases. The putative NTPase protein sequence, referred to herein as "CD39L2," is shown in FIGS. 3A, 3B, 3C, and 3D alongside the other NTPase protein sequences. The identification and characterization of the full-length CD39L2 polypeptide and nucleotide sequences is described in the Example presented in Section 7, below.

To map the murine mNTPase gene, a cosmid was isolated from a mouse cosmid library, and used for fluorescence in situ hybridization (FISH). For the FISH analysis, slides with mouse metaphase chromosomes were prepared from spleens as described in Monier et al. (Monier, K. et al., 1996, Cytogenet. Cell Genet. 72:200–204). 1 microgram of mouse cosmid containing the mNTPase gene was labeled with biotin 14-ATP and a Bionick Kit (GibcoBRL). DNA was purified by passage through a Sephadex G50 column and ethanol precipitated with 50 micrograms of sheared salmon sperm DNA and tRNA. 80 ng of probe was dried down with 3 micrograms of mouse Cot-1 DNA (GibcoBRL). Hybridization was carried out as described (Ragoussis, J. et al., 1992, Genomics 14:423–430). Confirmation of chromosomal location was achieved by rehybridizing the same slide with a mouse Chromosome 12-specific Starfish Paint (Cambio).

The FISH study revealed the presence of mNTPase on mouse Chr. 12 at chromosome band E. To confirm the location of the mNTPase gene on mouse Chr. 12, linkage analysis was carried out upon the European Collaborative Interspecific Backcross (EUCIB). PCR primers were designed to the 3 untranslated region of the mNTPase cDNA sequence and used for PCR by use of mouse genomic DNA from the two parental mouse strains, *Mus spretus* and C57BL/6. A polymorphism was detected between the two strains by SSCP analysis and was used for the mapping. (PCR conditions: 48° C. 20 sec., Primer 1: CCAGACTGTAAATCTTTTGG (SEO ID NO: 20); Primer 2: AGGGAATGTAATAAGGGTAG (SEQ ID NO: 21); conditions: 94° C. 2 minutes; 35 cycles of 94° C. 20 sec. 72° C. 20 sec., 72° C. 1 min; product size: 320 bp).

Linkage with a LOD score of 8.14 was obtained with the genetic marker D12Mit4, flanked by D12Mit149 and D12Mit238, between 31.7 cM and 36.1 cM from the top of the mouse Chr. 12 linkage group for the MIT $F_2$ Intercross. This region of mouse Chr. 12 has previously been shown to share synteny with human Chr. 14q (DeBry, R. W. & Seldin, M. F., 1996, Genomics 33:337–351).

7. EXAMPLE

Identification and Characterization of Additional Novel CD39-like Polypeptides and Nucleic Acid Molecules Described herein is the cloning and characterization of novel CD-39-like nucleotide-triphosphatase ("NTPase") gene and polypeptide sequences. These sequences are referred to below as "CD39L2," "CD39L3," "CD39L4" and "dCD39L4."

7.1. Materials and Methods

The nucleotide sequence of CD39 (Accession No. S73813), CD39L1 (Accession No. U91510), and mNTPase (see Section 6, above) were used in TBLASTX searches against entries in the expressed sequence tag (EST) database at EMBL/GenBank, using the Bork server through EMBL-Heidelberg. cDNA clones for homologous IMAGE EST entries were obtained from the Human Genome Mapping Project Resource Centre (HGMP, Hinxton, UK). DNA was prepared with QiaTip100 (Qiagen), and the cDNA was sequenced by primer walking with a fluorescence labeled dye-terminator cycle sequencing kit according to the manufacturer's instructions (PRISM Ready Dye-Deoxy Terminator Premix from Applied Biosystems Inc.) and electrophoresed on an ABI 373 (Perkin-Elmer). Overlapping EST clones were identified by searching with the nucleotide sequence against entries in the EST database using BLAST-N.

Additional IMAGE cDNA clones were ordered from HGMP if they extended the existing nucleotide sequence further 5'. cDNA clones corresponding to the most 5' extreme of each gene were identified by hybridization of radiolabeled inserts of IMAGE cDNA clones to a keratinocyte stem cell cDNA library, a human adult breast epithelial cDNA library constructed using Stratagene Lambda ZAP vector, and a Jurkat cell line cDNA library in pBluescript (Dunne, J. et al., 1995, Genomics 30:207–223).

Northern analysis of members of the CD39-like gene family. cDNA clone inserts were removed by restriction digestion and separated by gel electrophoresis. Insert DNA was gel-purified and radiolabeled (Sambrook et al., 1989, supra). Radiolabeled cDNA was prehybridized at 65° C. for 2 h with 20 μg of human Cot-1 DNA (GibcoBRL) and 100 μg of total human DNA (Sigma), before hybridization to Northern blots (Clontech, human multiple tissue Northern blots, Catalog No. 7760-1 and 7759-1) according to the manufacturer's instructions.

Members of the CD39-like gene family were mapped in the human genome by PCR screening of the GeneBridge-4 radiation hybrid mapping panel obtained from the HGMP Resource Centre (Hinxton, UK) (Gyapay, G. et al., 1996, Hum. Mol. Genet. 5:339–346). PCR-positive radiation hybrid clones were organized into the GeneBridge-4 HGMP-RC subset order using the HGMP radiation hybrid mapping World Wide Web (WWW) site and mapping data for each gene were obtained from the Whitehead server. The chromosomal location for each gene was confirmed by PCR screening of the monochromosomal hybrids obtained from the HGMP Resource Centre. PCR primers were designed for the 3' untranslated region (UTR) of each gene and titrated for a unique human-specific PCR product. PCR conditions: CD39L2, Primer 1, 5'-CTGCTTGAGTGACGTCTCTG-3' (SEQ ID NO: 22); Primer 2, 5'-CACATGAGGTTCAGCTCGTG-3' (SEQ ID NO: 23); 94° C. for 2 min; 38 cycles of 94° C. for 20 s, 54° C. for 20 s, 72° C. for 20 s; 72° C. for 2 min. Product size is 362 bp). CD39L3, Primer 1: 5'-GTGAAGTGGCTGCCTTCAGG-3' (SEQ ID NO: 24); Primer 2, 5'-CCTTTGACTCGGGACTCCAG-3' (SEQ ID NO: 25); 94° C. for 2 min; 38 cycles of 94° C. for 20 s, 56° C. for 20 s, 72° C. for 2 min. Product size is 281 bp). CD39L4. Primer 1, 5'-GAACTGCTGCCTAACCACTC-3' (SEQ ID NO: 26); Primer 2, 5'-ATTGATGGGTCTTGGGATTGC-3' (SEQ ID NO: 27); 94° C. 2 for min; 38 cycles of 94° C. for 20 s, 56° C. for 20 s; 72° C. for 20 s; 72° C. for 2 min. Product size is 234 bp. PCR products were analyzed by electrophoresis through 3.5% NuSieve agarose gels (Flowgen).

7.2. Results

Isolation and Sequence Characterization of CD39L2.

Identification of partial human CD39L2 sequence was described in the Example presented in Section 6, above. The CD39L2 insert was used to isolate additional clones from a human adult breast epithelial cDNA library (ZR75), a human T-leukemia cell line J6 cDNA library (Jurkat), and a human keratinocyte stem cell cDNA library (KER). Of 23 cDNA clones that were isolated and sequenced, all but one appeared to be alternatively spliced or unspliced. Within the 2762 bp cDNA that appeared to be neither unspliced or alternatively spliced, an ORF extending to nucleotide 1600 containing ACRs I–IV was identified. Two ATG codons with a poor match to the consensus translation initiation site were found at nucleotide positions 148 and 232 (AUGUGAAUGA (SEQ ID NO: 28) at 148 and ACAAGGAUGA (SEQ ID NO: 29) at 232 versus consensus GCCGCCAUGG (SEQ ID NO: 19); Kozak, M., 1989, J. Biol. Chem. 108:229–241). Based on homology to mNTPase, the ATG at nucleotide position 232 is the initiation codon. (See FIGS. 9A, 9B, 9C, 9D, and 9E for a depiction of the CD39L2 amino acid sequence that results from translation from the upstream, position 148, start codon; such a form of CD39L2 as well as nucleotide sequences that encode this form of the polypeptide are also intended to be included as part of the present invention.) A single polyadenylation signal of AAUAAA (SEQ ID NO: 30) was identified at nucleotide position 2700, 22 nucleotides 5' of the poly(A) tail of the human CD39L2 cDNA.

Figure 5C:
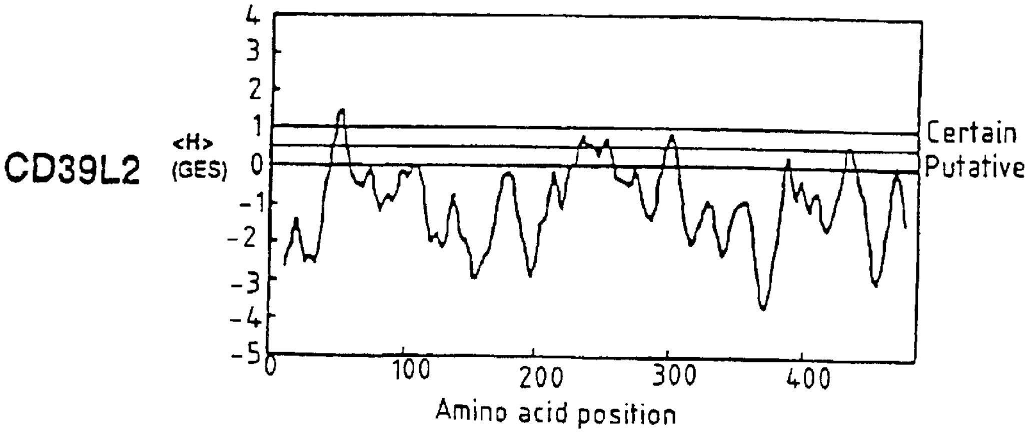

The nucleotide sequence (SEQ ID NO:1) and derived amino acid sequence (SEQ ID NO:2) of human CD39L2 is depicted in FIGS. 4A, 4B, 4C, 4D, 4E, 4F, 4G, and 4H. Hydrophobicity plots using Topred-II 1.1 (Claros, M. G. & Von Hejine, G., 1994, Comput. Appl. Biosci. 10:685–686) predicted a single transmembrane segment at the N-terminal extreme of the protein, suggesting that CD39L2 has a short putative cytoplasmic tail and a large extracellular C-terminal domain (FIG. 5C). There are two potential N-glycosylation sites in the predicted extracellular domain. A cAMP and cGMP-dependent protein kinase and a protein kinase-C phosphorylation site are found directly after the initiation methionine codon (nucleotide 232).

Isolation and Sequence Characterization of CD39L3. An additional novel gene and polypeptide CD39-like sequence, referred to herein as CD39L3, was also identified. BLASTN search of the NCBI EST database with the full cDNA sequence for human CD39 (Accession No. S73813) identified three EST entries for cDNA clones from an endometrial tumor library (Accession Nos. AA336644, AA338117, and AA337885), which led to the identification of an IMAGE library EST (Accession No. N72742) that was completely sequenced and had amino acid homology to CD39 and CD39L1. The insert of N72742 was used to screen the Jurkat, ZR75, and KER cDNA libraries, and a single cDNA clone was isolated from the KER library and sequenced.

Figure 5D:
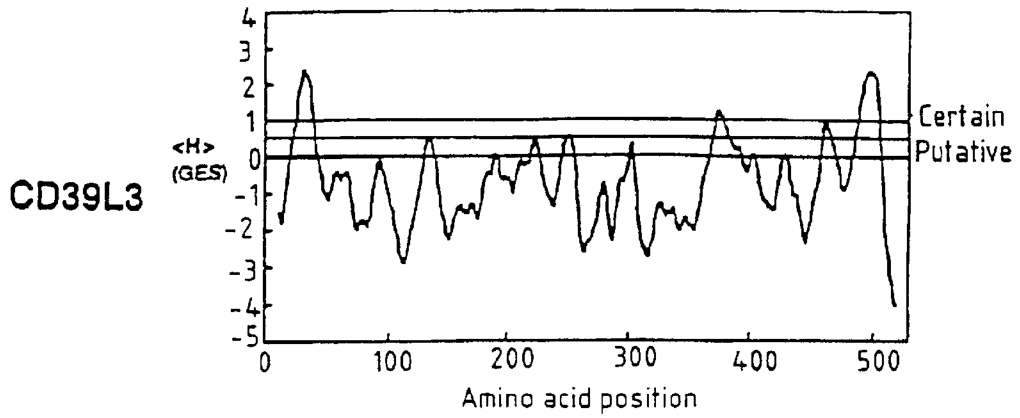

A 1669-bp ORF was identified within the cDNA insert. The nucleotide sequence (SEQ ID NO:3) and derived amino acid sequence (SEQ ID NO:4) of the cDNA insert, referred to herein as CD39L3, are shown in FIGS. 6A, 6B, 6C, 6D, 6E, 6F, 6G, and 6H. The amino acid sequence was revealed to contain ACRs I–IV, an ATG codon at position 83, and a single polyadenylation signal at position 2758. Hydrophobicity plots as described above predict two potential transmembrane segments at the N and C-terminal extremes of the protein (FIG. 5D). There are seven potential extracellular N-glycosylation sites. A cAMP- and cGMP-dependent protein kinase site and a protein kinase-C phosphorylation site are located at the C-terminal extreme of the protein.

An additional (CD39-like gene and polypeptile sequence, referred to herein as CD39L4, was also identified. A TBLASTX search of the NCBI EST database with the full cDNA sequence for the mNTPase was performed. A human EST clone was sequenced, and an ORF was identified extending to nucleotide 529 of 2260 nucleotides that contained ACR I only and an ATG codon at position 256. In the same reading frame, downstream of the stop codon at nucleotide 529, an ORF extending to nucleotide 1792 contained ACRs II, III, and IV. Further analysis of the nucleotide sequence revealed a putative intron with splice donor and acceptor sites that conform to the 5' gt . . . 3' ag rule (Breathnach and Chambon, 1981, Ann Rev. Biochem. 50:349–383; splice donor CAGgtcacttatggagcctg (SEQ ID NO: 31) at nucleotide position 470, acceptor ccatggacaaaatagGAC (SEQ ID NO: 32) at position 710, exon sequence underlined). Further analysis of the sequence revealed that removal of the 251-bp putative intron would result in a contiguous ORF containing ACRs I-IV. The hypothesis that this sequence does indeed constitute an intron was only confirmed by isolation and sequencing of three additional cDNA clones (CD39L4J1-3) from the Jurkat library, one of which contained the 251 bp.

Figure 5E:
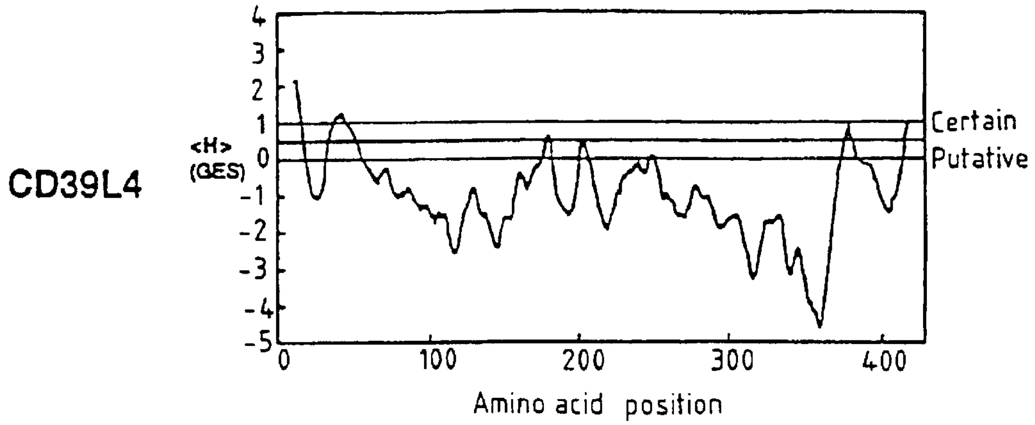
Figure 8B:
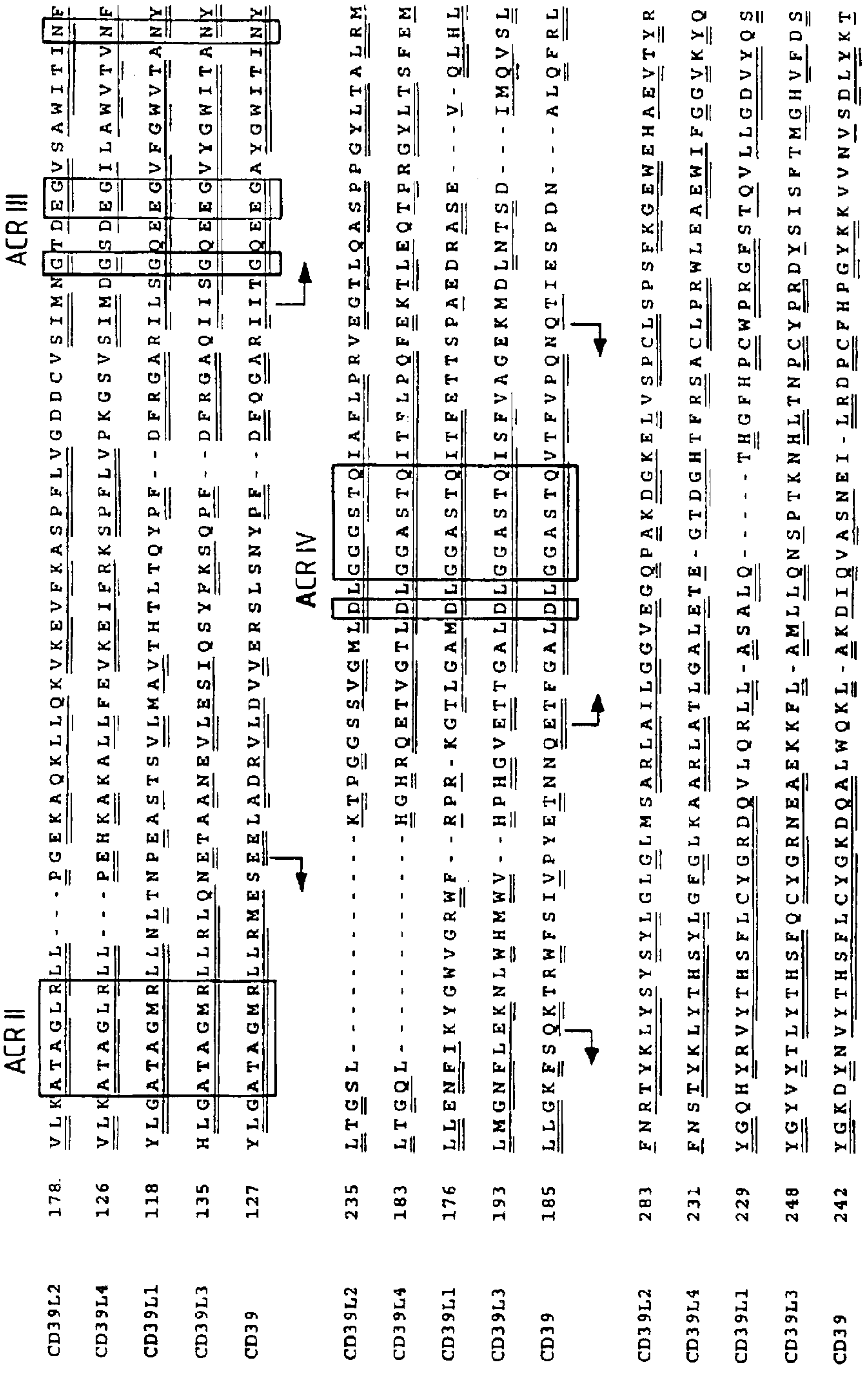
Figure 9B:
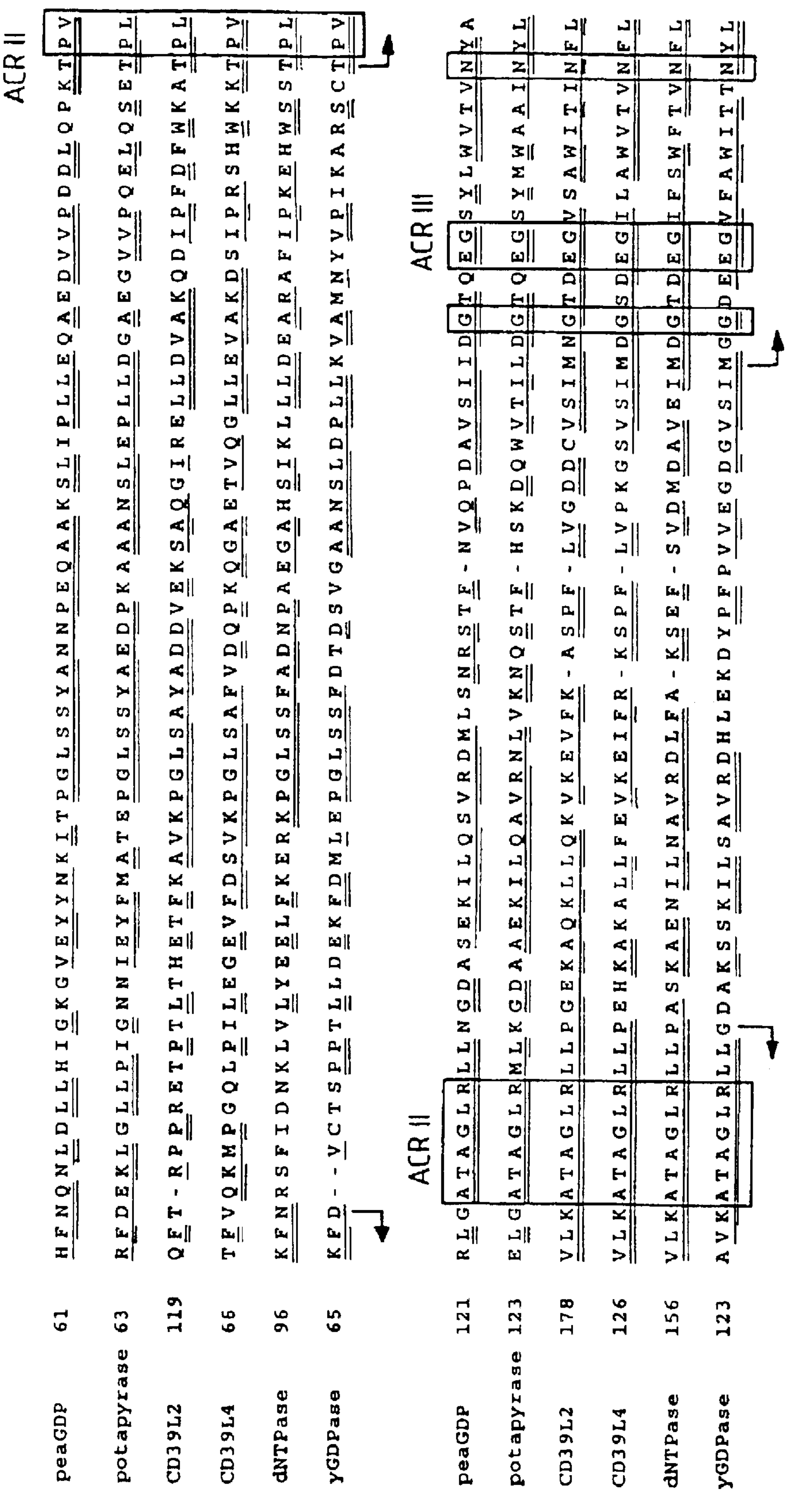

The nucleotide sequence (SEQ ID NO:5) and derived amino acid sequence (SEQ ID NO:6), referred to herein as CD39L4, is depicted in FIGS. 7A, 7B, 7C, 7D, 7E, and 7F. The sequence contained a poly(A)tail, but no consensus polyadenylation sequence (Proudfoot, 1991, New Biol. 3:851–854). This is also the case for mNTPase. Hydrophobicity plots as described above predicted a single transmembrane segment at the N-terminal extreme of the protein (FIG. 5E). This is similar to the predicted topology of CD39L2 and different from that of CD39, Cd39L1, and CD39L3. There are three potential extracellular N-glycosylation sites.

FIGS. 8A, 8B, 8C, and 8D depicts an alignment of each of the above-described sequences, along with other members of the NTPase CD-39-like gene family. The ACR domains are indicated by arrows.

Expression of the Human Members of the CD39-like Family.

Representative probes for each member of the CD39-like gene family were hybridized to human multiple tissue Northern blots. Results are presented below.

CD39L2. Hybridization of the CD39L2 cDNA insert to the multiple tissue Northern blots resulted in two prominent signals of 2.6 kb (major) and 4.4 kb (minor) in all tissues studied. This is most likely due to differential polyadenylation.

CD39L3. A PCR product covering the coding sequence of CD39L3 was used for the Northern hybridizations. A strong signal of approximately 3.0 kb could be seen in adult brain, pancreas, spleen, and prostate. Though moderate or low expression was seen in most other tissues, no signal was detected in adult liver and peripheral blood leukocytes. A weaker signal of approximately 1.8 kb was found in adult pancreas and may be the result of alternative splicing.

CD39L4. The CD39L4 cDNA was hybridized to the same Northern blots, and a prominent signal of approximately 4.8 kb was seen in adult liver, kidney, prostate, testis, and colon. Considerably weaker expression was seen for all other tissues examined. Several smaller bands were observed in tissues showing the strongest expression of CD39L4 and may be the result of differential polyadenylation or alternative splicing.

Mapping of Members of the CD39-like Family.

The CD39L2 gene was mapped with a lod score of >19 to human chromosome 20 by PCR typing of the GeneBridge 4 Radiation Hybrid Mapping Panel (Gyapay et al., 1996, Human Mol. Genet. 5:339–346). CD39L2 mapped 9.76 cR from D20S493 (typing data: 12012 02101 22000 00111 00110 01210 00110 01101 10121 00100 00120 11211 00011 11012 01001 01102 00000 00000 001). Using the closet flanking markers (D20S184 and D20S99) also represented on the consensus map, this placed CD39L2 at chromosome band 20q11.2. The location of CD39L2 on human chromosome 20 was confirmed by PCR analysis of monochromosomal mapping panels (Kelsell et al., 1995, Ann. Human Genet. 59:233–241). On the basis of synteny to human chromosome 20q11.2, the mouse homolog of CD39L2 was expected to map to mouse chromosome 2 (DeBry and Seldin, 1996, Genomics 3:337–351).

The CD39L3 gene was mapped as described above to human chromosome 3, 5.76 cR from D3S3390 (data: 12002 02010 22000 00011 20000 00110 01001 00000 02022 11000 10001 00200 21100 00212 01010 10002 00000 00011 001). Using the closest flanking markers as described above (D3S1561 and D3S3564), this placed CD39L3 at chromosome band 3p21.3. The location of CD39L3 on chromosome 3 was confirmed by PCR as for CD39L2. On the basis of synteny, the mouse homologue of Cd39L3 was expected to map to mouse chromosome 9 (DeBry and Seldin, 1996, Genomics 33:337–351).

The CD39L4 gene was mapped as described above to human chromosome 14, 1.92 cR from D14S71 (data: 02102 02102 22000 01010 11021 01000 01010 10110 02121 21000 00010 00211 01001 10102 02012 00002 12111 01100 002). This placed CD39L4 at chromosome band 14q24. The chromosomal location of CD39L4 was confirmed as described above.

Identification of a Drosophila Gene with high Nomolocv to CD39L2 and CD39L4. A *D. melanogaster* CD39-like gene was also identified. A TBLASTX search of the EST database using the human CD39L2 cDNA sequence, five Drosophila EST entries were identified (Accession No. AA391695, AA390461, AA201196, AA246996, and AA567512). A consensus sequence was generated and used for a BLASTN search against EMBL/GenBank entries. A single *D. melanogaster* genomic entry (Accession No. AC002032) was identified showing 100% sequence identity to three regions of the EST consensus sequence. Alignment of the EST consensus against the genomic sequence identified three exons that conform to the 5' gt . . . 3' ag rule (Breathnach & Chambon, 1981, Ann. Rev. Biochem. 50:349–383). Exon 4 was identified on the basis of reading frame homology to the CD39L2 and CD39L4 proteins. An ATG codon was identified in exon 1, a stop codon in exon 4.

The predicted amino acid sequence of the *D. melanogaster* CD39-like gene, referred to herein as dCD39L4, containing the ACRs-I–IV was shown in FIGS. 9A, 9B, 9C, 9D, and 9E, aligned against the gene family members with the highest homology. Three N-glycosylation consensus sites were found in the putative extracelluar domain, and two potential cAMP- and c-GMP-dependent protein kinase phosphorylation sites were found in the putative N-terminal cytoplasmic domain. Hydrophobicity plots as described above predicted a single transmembrane segment at the N-terminal extreme of the dCD39L4 protein. The topology of dCD39L4 is therefore most similar to the predicted topology of the CD39L2 and Cd39L4 proteins.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

What is claimed is:

1. An isolated antibody or antigen binding fragment thereof which specifically binds to a CD39L4 polypeptide comprising the amino acid sequence of SEQ ID NO: 6.

2. The isolated antibody or antigen binding fragment thereof of claim 1 wherein the antibody is a monoclonal antibody.

3. The isolated antibody or antigen binding fragment thereof of claim 1 wherein the antigen binding fragment which is an antigen binding fragment of a monoclonal antibody.

4. A hybridoma which produces the monoclonal antibody of claim 2.

5. The isolated antibody or antigen binding fragment thereof of claim 1 wherein the antibody is a polyclonal antibody.

6. The isolated antibody or antigen binding fragment thereof of claim 1 wherein the antigen binding fragment is an antigen binding fragment of a polyclonal antibody.

7. A labeled antibody, wherein the antibody of claim 1 comprises a detectable label.

8. The labeled antibody of claim 7 wherein the detectable label is a radioisotope, affinity label, enzymatic label, fluorescent label or paramagnetic moiety.

9. A kit comprising (a) the antibody or antigen binding fragment thereof of claim 1 and (b) a polypeptide comprising the amino acid sequence of SEQ ID NO: 6.

10. A kit comprising (a) the antibody or antigen binding fragment thereof of claim 1 and (b) a wash reagent or a reagent capable of detecting the presence of a bound antibody.

* * * * *